(12) United States Patent
Beauchamp et al.

(10) Patent No.: US 8,969,555 B2
(45) Date of Patent: Mar. 3, 2015

(54) BICYCLIC PYRIMIDINE COMPOUNDS

(71) Applicant: Eli Lilly and Company, Indianapolis, IN (US)

(72) Inventors: Thomas James Beauchamp, Fishers, IN (US); Yen Dao, Indianapolis, IN (US); Spencer Brian Jones, Fishers, IN (US); Bryan Hurst Norman, Indianapolis, IN (US); Lance Allen Pfeifer, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/148,775

(22) Filed: Jan. 7, 2014

(65) Prior Publication Data

US 2014/0200231 A1    Jul. 17, 2014

Related U.S. Application Data

(60) Provisional application No. 61/751,363, filed on Jan. 11, 2013, provisional application No. 61/777,201, filed on Mar. 12, 2013.

(51) Int. Cl.
*C07D 239/70* (2006.01)
*C07D 487/04* (2006.01)
*C07D 471/04* (2006.01)

(52) U.S. Cl.
CPC ............ *C07D 487/04* (2013.01); *C07D 471/04* (2013.01)
USPC ............................ 544/253; 544/262; 544/280

(58) Field of Classification Search
USPC .......................... 544/253, 262, 280
See application file for complete search history.

(56) References Cited

U.S. PATENT DOCUMENTS 7,524,852 B2    4/2009    Arai et al.

FOREIGN PATENT DOCUMENTS

| WO | 2006119504 | 11/2006 |
|---|---|---|
| WO | 2012/024620 | 2/2012 |
| WO | 2012085167 | 6/2012 |
| WO | 2013054185 | 4/2013 |

OTHER PUBLICATIONS

Unpublished co-pending, commonly assigned application PCT/US2014/020297.
Unpublished co-pending, commonly assigned application PCT/US2014/032946.

*Primary Examiner* — Jeffrey H Murray
*Assistant Examiner* — Oluwafemi Masha
(74) *Attorney, Agent, or Firm* — Macharri R. Vorndran-Jones

(57) ABSTRACT

The present invention provides compounds of the Formula I:

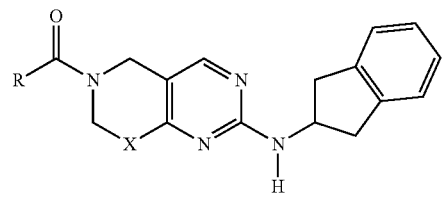

wherein X is a bond or $CH_2$;

R is selected from the group consisting of

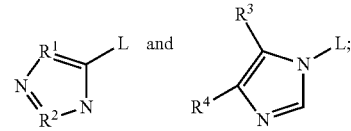

$R^1$ and $R^2$ are each independently selected from the group consisting of CH and N;

$R^3$ is H or $CH_3$;

$R^4$ is H or $CH_3$;

L is selected from the group consisting of $-O(CH_2)_3-$, $-C(O)NH(CH_2)_2-$, $-CH_2C(O)NH(CH_2)_2-$, $-(CH_2)_3N(C(O)CH_3)CH_2-$, $-(CH_2)_2N(C(O)CH_3)CH_2-$, $-(CH_2)_3NH-$, $(CH_2)_2OCH_2-$, $-(CH_2)_4-$, $-(CH_2)_2NHCH_2-$, $-(CH_2)_3O-$, and $-CH_2O(CH_2)_2-$;

or a pharmaceutically acceptable salt thereof.

Compounds of this invention are autotaxin inhibitors.

15 Claims, No Drawings

BICYCLIC PYRIMIDINE COMPOUNDS

This invention relates to bicyclic pyrimidine compounds, or pharmaceutically acceptable salts thereof, and therapeutic use thereof. Compounds of this invention are autotaxin inhibitors.

Autotaxin is an enzyme reported to be the source of lysophosphatidic acid (LPA) which up-regulates pain-related proteins through one if its cognate receptors, $LPA_1$. LPA is an intracellular lipid mediator which influences a multiplicity of biological and biochemical processes. Targeted inhibition of autotaxin-mediated LPA biosynthesis may provide a novel mechanism to prevent nerve injury-induced neuropathic pain. Compounds that inhibit autotaxin are desired to offer a potential treatment option for patients in need of treatment for pain.

Pain associated with osteoarthritis (OA) is reported to be the primary symptom leading to lower extremity disability in OA patients. Over 20 million Americans have been diagnosed with OA, the most common of the arthropathies. The currently approved treatments for OA pain may be invasive, lose efficacy with long term use, and may not be appropriate for treating all patients. Additional treatment options for patients suffering from pain associated with OA are desired. Compounds that inhibit autotaxin represent another possible treatment option for patients with pain associated with OA.

U.S. Pat. No. 7,524,852 ('852) discloses substituted bicyclic pyrimidine derivatives as anti-inflammatory agents.

PCT/US2011/048477 discloses indole compounds as autotoxin inhibitors.

There is a need for novel compounds that provide autotaxin inhibition. The present invention provides novel compounds which are autotaxin inhibitors. The present invention provides certain novel compounds that inhibit the production of LPA. Autotaxin inhibitor compounds are desired to provide treatments for autotaxin mediated conditions, such as pain and pain associated with OA.

The present invention provides compounds of the Formula I:

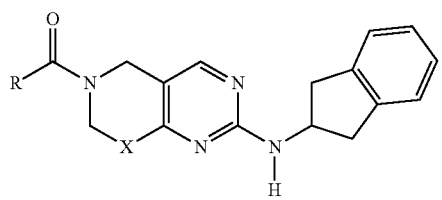

wherein X is a bond or $CH_2$;
R is selected from the group consisting of

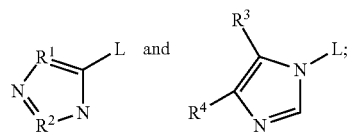

$R^1$ and $R^2$ are each independently selected from the group consisting of CH and N;
$R^3$ is H or $CH_3$;
$R^4$ is H or $CH_3$;
L is selected from the group consisting of $—O(CH_2)_3—$, $—C(O)NH(CH_2)_2—$, $—CH_2C(O)NH(CH_2)_2—$, $—(CH_2)_3N(C(O)CH_3)CH_2—$, $—(CH_2)_2N(C(O)CH_3)CH_2—$, $—(CH_2)_3NH—$, $—(CH_2)_2OCH_2—$, $—(CH_2)_4—$, $—(CH_2)_2NHCH_2—$, $—(CH_2)_3O—$, and $—CH_2O(CH_2)_2—$; or a pharmaceutically acceptable salt thereof.

The present invention also provides a method of treating pain in a patient, comprising administering to a patient in need of such treatment an effective amount of a compound of Formula I, or a pharmaceutically acceptable salt thereof. The present invention also provides a method of treating pain associated with osteoarthritis in a patient, comprising administering to a patient in need of such treatment, an effective amount of a compound of Formula I, or a pharmaceutically acceptable salt thereof.

This invention provides a compound of Formula I, or a pharmaceutically acceptable salt thereof, for use in therapy, in particular for the treatment of pain or for the treatment of pain associated with OA. Even furthermore, this invention provides the use of a compound of Formula I, or a pharmaceutically acceptable salt thereof, for the manufacture of a medicament for the treatment of pain. This invention also provides the use of a compound of Formula I, or a pharmaceutically acceptable salt thereof, for the manufacture of a medicament for the treatment of pain associated with OA.

The invention further provides a pharmaceutical composition, comprising a compound of Formula I, or a pharmaceutically acceptable salt thereof, in combination with one or more pharmaceutically acceptable carriers, diluents, or excipients. The invention also encompasses novel intermediates and processes for the synthesis of the compounds of Formula I.

The term "pharmaceutically-acceptable salt" refers a salt of the compound of the invention considered to be acceptable for clinical and/or veterinary use. Pharmaceutically acceptable salts and common methodology for preparing them are well known in the art.

See, e.g., P. Stahl, et al., Handbook of Pharmaceutical Salts: Properties, Selection and Use, (VCHA/Wiley-VCH, 2002); S. M. Berge, et al., "Pharmaceutical Salts," *Journal of Pharmaceutical Sciences*, Vol. 66, No. 1, January 1977.

The term "treating" (or "treat" or "treatment") as used herein refers to restraining, slowing, stopping, or reversing the progression or severity of an existing symptom, condition, or disorder. Symptoms, conditions, or disorders may present as "acute" or "chronic" events. In an acute event compound is administered at the onset of symptom, condition, or disorder and discontinued when the event disappears. A chronic event is treated during the course of the disorder or condition associated with the symptom or event, wherein the chronic treatment is not dependent on a particular manifestation of the symptom or event. The present invention contemplates both acute and chronic treatment.

Compounds of the present invention inhibit autotaxin, and may be useful for treating a disease or condition accompanied by an increase in autotaxin. Compounds of the present invention inhibit the production of LPA and may be useful for treating a disease or condition accompanied by an increase in LPA. Compounds of this invention may inhibit autotaxin mediated LPA biosynthesis when compared to other LPA lipid mediators. Compounds of this invention may be useful for treating a disease or condition accompanied by an increase in $LPA_1$ binding.

As used herein, "patient" refers to an animal in need of treatment, preferably not exclusively a mammal. A preferable embodiment is a patient that is a mammal, which is preferably a human. Another preferable embodiment is a patient that is a companion animal such as a dog, cat or a fowl.

As used herein, the term "effective amount" refers to the amount or dose of compound of the invention or a pharmaceutically acceptable salt thereof which upon single or multiple dose administration to the patient, provides the desired effect in the patient under diagnosis or treatment. It will be understood that the amount of active agent actually administered will be determined by a physician, in light of the relevant circumstances, including the condition to be treated, the chosen route of administration, the actual active agent administered, the age, weight, and response of the individual patient, and the severity of the patient's symptoms and other relevant circumstances.

A compound of the present invention is preferably formulated as pharmaceutical composition administered by any route which makes the compound bioavailable. Most preferably, such compositions are for oral administration. Such pharmaceutical compositions and processes for preparing same are well known in the art. See, e.g., *Remington: The Science and Practice of Pharmacy* (D. B. Troy, Editor, 21st Edition, Lippincott, Williams & Wilkins, 2006).

The artisan will appreciate that the structure

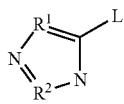

embraces all tautomeric forms. For avoidance of doubt, the structure embraces isomers that readily interconvert by a tautomerization. The structure embraces, for example, the tautomers

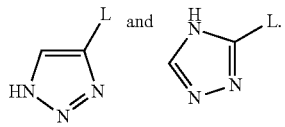

The compounds of Formula I are particularly useful in the treatment methods of the invention, but certain groups, substituents, and configurations are preferred for compounds of Formula I. The following paragraphs describe such preferred groups, substituents, and configurations. It will be understood that these preferences are applicable both to the treatment methods and to the new compounds of the invention.

It is preferred that R is

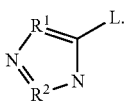

It is preferred that R1 is CH.
It is preferred that R2 is N.
It is preferred that when $R^1$ is CH and $R^2$ is N, L is $(CH_2)_2$ $OCH_2$ or $O(CH_2)_3$.
It is preferred that when R is

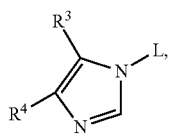

$R^3$ and $R^4$ are each H.
It is preferred that only one of $R^3$ and $R^4$ is $CH_3$.
It is preferred that X is a bond.

It is preferred that X is $CH_2$.
It is especially preferred that X is a bond and L is —$(CH_2)_3NH$—. It is preferred that X is a bond, R is

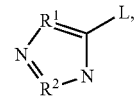

$R^1$ is CH, and L is —$(CH_2)_2OCH_2$— or $(CH_2)_2OCH_2$ and salts thereof. It is especially preferred that X is a bond and L is —$(CH_2)_2OCH_2$—. It is further preferred that X is a bond, and L is —$CH_2O$—. and R is

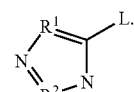

It is preferred that X is $CH_2$, R is

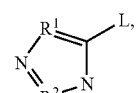

$R^1$ is CH, $R^2$ is N, L is —$(CH_2)_2OCH_2$— or $(CH_2)_2OCH_2$ and salts thereof.
It is especially preferred that X is $CH_2$ and L is —$(CH_2)_2$ $OCH_2$— and R is

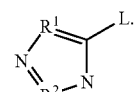

Preferred compounds are:
H-{3-[2-(2,3-dihydro-1H-inden-2-ylamino)-7,8-dihydropyrido[4,3-d]pyrimidin-6(5H)-yl]-3-oxopropyl}-2-(1H-imidazol-1-yl)acetamide, 3-(4-methyl-1H-imidazol-1-yl)propyl 2-(2,3-dihydro-1H-inden-2-ylamino)-7,8-dihydropyrido[4,3-d]pyrimidine-6(5H)-carboxylate, 1-[2-(2,3-dihydro-1H-inden-2-ylamino)-7,8-dihydropyrido[4,3-d]pyrimidin-6(5H)-yl]-5-(1H-imidazol-1-yl)pentan-1-one, 3-(1H-imidazol-1-yl)propyl 2-(2,3-dihydro-1H-inden-2-ylamino)-7,8-dihydropyrido[4,3-d]pyrimidine-6(5H)-carboxylate, 1-[2-(2,3-dihydro-1H-inden-2-ylamino)-7,8-dihydropyrido[4,3-d]pyrimidin-6(5H)-yl]-2-[2-(1H-imidazol-1-yl)ethoxy]ethanone, and the pharmaceutically acceptable salt thereof.

Preferred compounds are:
1-[2-(2,3-dihydro-1H-inden-2-ylamino)-7,8-dihydropyrido[4,3-d]pyrimidin-6(5H)-yl]-2-[2-(1H-1,2,3-triazol-4-yl)ethoxy]ethanone, 1-[2-(2,3-dihydro-1H-inden-2-ylamino)-7,8-dihydropyrido[4,3-d]pyrimidin-6(5H)-yl]-5-(4H-1,2,4-triazol-3-yl)pentan-1-one, 1-[2-(2,3-dihydro-1H-inden-2-ylamino)-7,8-dihydropyrido[4,3-d]pyrimidin-6(5H)-yl]-3-(1H-1,2,3-triazol-4-ylmethoxy)propan-1-one, 3-(1H-tetrazol-5-yl)propyl 2-(2,3-dihydro-1H-inden-2-ylamino)-7,8-dihydropyrido[4,3-d]pyrimidine-6(5H)-carboxylate, 1-[2-(2,3-dihydro-1H-inden-2-ylamino)-7,8-dihydropyrido[4,3-d]pyrimidin-6(5H)-yl]-2-{[2-(1H-1,2,3-triazol-4-yl)-ethyl]amino}ethanone, 2-(2,3-dihydro-1H-inden-2-ylamino)-n-[3-(1H-1,2,3-triazol-4-yl)propyl]-7,8-dihydropyrido[4,3-d]pyrimidine-6(5H)-carboxamide, N-{2-[2-(2,3-dihydro-1H-inden-2-ylamino)-7,8-dihydropyrido[4,3-d]pyrimidin-6

(5H)-yl]-2-oxoethyl}-N-[3-(1H-1,2,3-triazol-4-yl)propyl]
acetamide, N-{2-[2-(2,3-dihydro-1H-inden-2-ylamino)-7,8-
dihydropyrido[4,3-d]pyrimidin-6(5H)-yl]-2-oxoethyl}-n-
[2-(1H-1,2,3-triazol-4-yl)-ethyl]acetamide, N-{3-[2-(2,3-
dihydro-1H-inden-2-ylamino)-7,8-dihydropyrido[4,3-d]
pyrimidin-6(5H)-yl]-3-oxopropyl}-2-(1H-1,2,3-triazol-5-
yl)acetamide, N-{3-[2-(2,3-dihydro-1H-inden-2-ylamino)-
7,8-dihydropyrido[4,3-d]pyrimidin-6(5H)-yl]-3-
oxopropyl}-1H-1,2,3-triazole-4-carboxamide, and the
pharmaceutically acceptable salts thereof.

Preferred compounds are:
1-[2-(2,3-dihydro-1H-inden-2-ylamino)-5,7-dihydro-6H-
pyrrolo[3,4-d]pyrimidin-6-yl]-5-(1H-tetrazol-5-yl)pentan-
1-one, 1-[2-(2,3-dihydro-1H-inden-2-ylamino)-5,7-dihydro-
6H-pyrrolo[3,4-d]pyrimidin-6-yl]-2-{[2-(1H-1,2,3-triazol-
5-yl)-ethyl]amino}ethanone, 3-(1H-tetrazol-5-yl)propyl
2-(2,3-dihydro-1H-inden-2-ylamino)-5,7-dihydro-6H-pyr-
rolo[3,4-d]pyrimidine-6-carboxylate, 2-(2,3-dihydro-1H-in-
den-2-ylamino)-N-[3-(1H-1,2,3-triazol-4-yl)propyl]-5,7-di-
hydro-6H-pyrrolo[3,4-d]pyrimidine-6-carboxamide, 3-(1H-
imidazol-5-yl)propyl 2-(2,3-dihydro-1H-inden-2-ylamino)-
5,7-dihydro-6H-pyrrolo[3,4-d]pyrimidine-6-carboxylate,
1-[2-(2,3-dihydro-1H-inden-2-ylamino)-5,7-dihydro-6H-
pyrrolo[3,4-d]pyrimidin-6-yl]-4-(1H-1,2,3-triazol-5-yloxy)
butan-1-one, 1-[2-(2,3-dihydro-1H-inden-2-ylamino)-5,7-
dihydro-6H-pyrrolo[3,4-d]pyrimidin-6-yl]-2-[2-(1H-1,2,3-
triazol-4-yl)ethoxy]ethanone; and the pharmaceutically
acceptable salts thereof.

Especially preferred compounds are:
1-[2-(2,3-dihydro-1H-inden-2-ylamino)-5,7-dihydro-6H-
pyrrolo[3,4-d]pyrimidin-6-yl]-2-[2-(1H-1,2,3-triazol-4-yl)
ethoxy]ethanone; and 1-[2-(2,3-dihydro-1H-inden-2-
ylamino)-7,8-dihydropyrido[4,3-d]pyrimidin-6(5H)-yl]-2-
[2-(1H-1,2,3-triazol-4-yl)ethoxy]ethanone; and the
pharmaceutically acceptable salts thereof.

PREPARATIONS AND EXAMPLES

The following Preparations and Examples further illustrate
the invention and represent a typical synthesis of the com-
pound of the invention. It should be understood that the
Preparations and Examples are set forth by way of illustration
and not limitation, and that various modifications may be
made by one of ordinary skill in the art. In the schemes
presented below, all substituents, unless otherwise indicated,
are as previously defined. Certain stereochemical centers
have been left unspecified and certain substituents have been
eliminated in the following schemes for the sake of clarity and
are not intended to limit the teaching of the schemes in any
way. Furthermore, individual isomers, enantiomers, or dias-
tereomers may be separated or resolved by one of ordinary
skill in the art at any convenient point in the synthesis of
compounds of Formula I by methods such as selective crys-
tallization techniques or chiral chromatography (see for
example, J. Jacques, et al., "*Enantiomers, Racemates, and
Resolutions*", John Wiley and Sons, Inc., 1981, and E. L. Eliel
and S. H. Wilen "*Stereochemistry of Organic Compounds*",
Wiley-Interscience, 1994). The reagents and starting materi-
als are generally available to one of ordinary skill in the art.
Others may be prepared by standard techniques of organic
and heterocyclic chemistry which are analogous to the syn-
thesis of known structurally similar compounds and proce-
dures described by the Preparations and Examples which
follow, including any novel procedures.

Unless noted to the contrary, the compounds illustrated
herein are named and numbered using either ACDLABS or
Symyx Draw 3.2.

Generally, a compound of formula I where X is a bond or
$CH_2$ may be prepared from a compound of formula II. More
specifically in Scheme A, a compound of formula II where X
is a bond or $CH_2$ is coupled with a compound of formula VII
in the presence of a carbodiimide, 1-hyroxybenzotraizole and
a base such as triethylamine to provide a compound of for-
mula I where X is a bond or $CH_2$. Suitable solvents include
dichloromethane.

Alternatively in Scheme A, a compound of formula I where
X is a bond or $CH_2$ may be prepared from a compound of
formula IV. More specifically, compound of formula IV
where X is a bond or $CH_2$ is reacted with azide source such as
azidotrimethylsilane in the presence of copper (II) sulfate in a
solvent such as dimethylformamide/water to provide a com-
pound of formula I where X is a bond or $CH_2$. A compound of
formula IV where X is a bond or $CH_2$ may be prepared by
reacting a compound of formula III with 3-butyn-1-ol and a
base such as sodium hydride in a solvent such as tetrahydro-
furan. A compound of formula III where X is a bond or $CH_2$
may be prepared by reacting a compound of formula II with
2-chloroacetyl chloride and a base such as triethylamine in a
solvent such as dichloromethane.

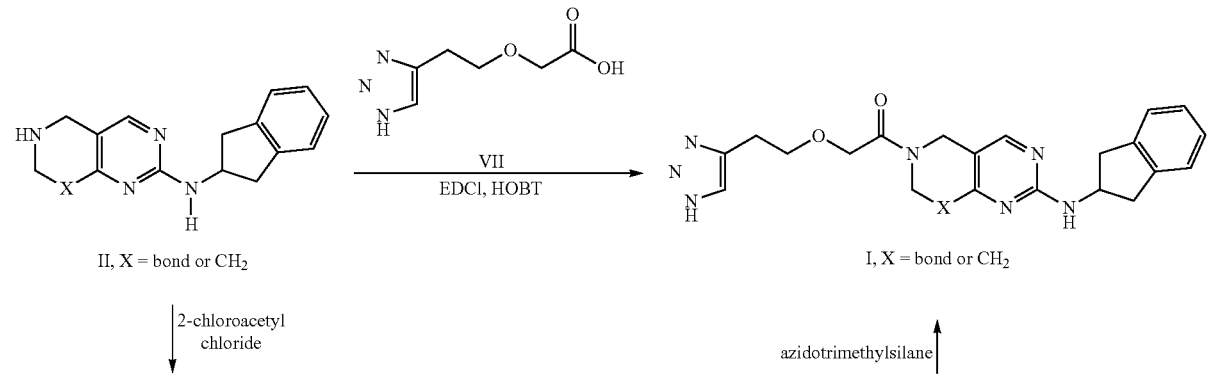

Scheme A

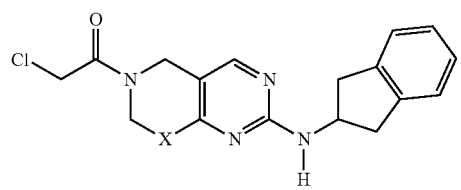

III, X = bond or CH₂

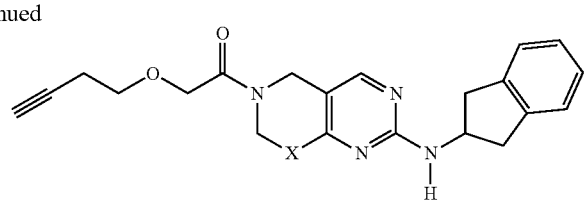

IV, X = bond or CH₂

As shown in Scheme B, a compound of formula II where X is a bond or CH₂ may be prepared from a compound of formula V where Pg is an amine protecting group. More specifically, a compound of formula V where X is a bond or CH₂; and Pg is tert-butoxycarbonyl is reacted with an acid such as hydrochloric acid in a solvent such as tetrahydrofuran to provide a compound of formula II where X is a bond or CH₂.

Scheme B

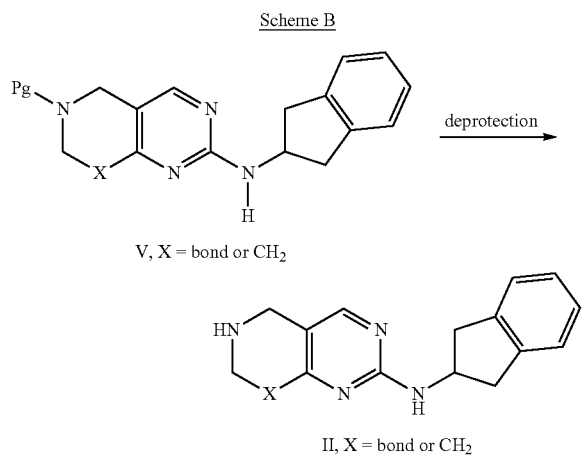

In Scheme C, a compound of formula V where X is CH₂; and Pg is tert-butoxycarbonyl may be prepared from a compound of formula VI. More specifically, N-tert-butoxycarbonyl-4-piperidone is reacted sequentially with (CH₃)₂NCH (OCH₃)₂ in a solvent such as dimethylformamide, and then with a compound of formula VI, a base such as potassium carbonate in a co-solvent such as ethanol to provide a compound of formula V where X is CH₂ and Pg is tert-butoxycarbonyl. A compound of formula VI may be prepared by reacting 2,3-dihydro-1H-inden-2-amine hydrochloride and 1H-pyrazole-1-carboximidamide hydrochloride with a base such as diisopropylethylamine in a solvent as acetonitrile.

Scheme C

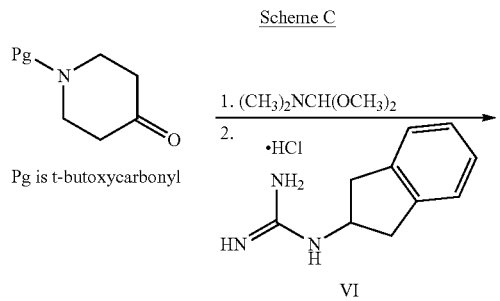

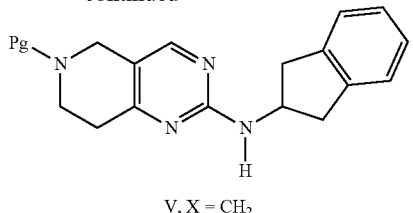

V, X = CH₂

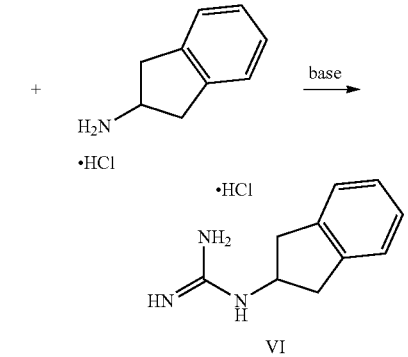

VI

In Scheme D, a compound of formula V where X is a bond and Pg is an amine protecting group such as tert-butoxycarbonyl may be prepared by reacting tert-butyl 2-chloro-5,7-dihydro-6H-pyrrolo[3,4-d]pyrimidine-6-carboxylate and 2,3-dihydro-1H-inden-2-amine in the presence of a base such as N-ethyl-N-isopropylpropan-2-amine in a solvent as 1-methylpyrrolidin-2-one.

Scheme D

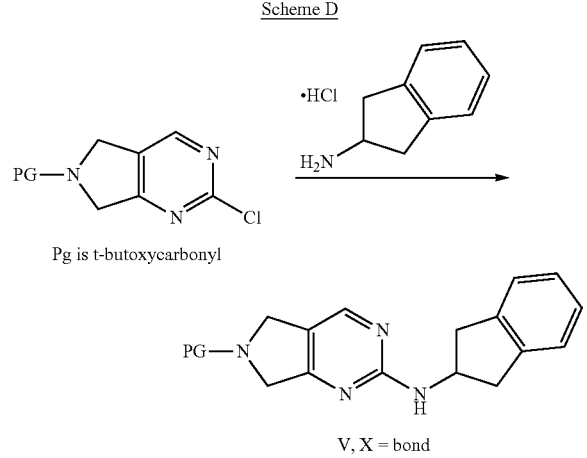

V, X = bond

Generally, a compound of formula VII may be prepared from 3-butyn-1-ol by employing multiple synthetic steps. More specifically in Scheme E, a compound of formula VIII where Pg1 is a carboxylic acid protecting group such as tert-butyl is reacted with an acid such as trifluoroacetic acid in a solvent such as dichloromethane to provide a compound of formula VII. A compound of formula VIII may be prepared by reacting a compound of formula IX where Pg1 is tert-butyl with azide source such as azidotrimethylsilane in the presence of copper (I) iodide in a solvent such as dimethylformamide/methanol. A compound of formula IX where Pg1 is tert-butyl may be prepared by reacting 3-butyn-1-ol with YCH2 C(O)OPg1 where Y is a suitable leaving group such the halogen bromo, and Pg1 is tert-butyl. The reaction is conveniently carried out with a phase transfer catalyst such as tetrabutylammonium sulfate, and a base such as aqueous sodium hydroxide in a solvent such as dichloromethane.

Alternatively in Scheme E, a compound of formula VII may be prepared by reacting a compound of formula X with hydrogen in the presence of a transition metal catalyst such as palladium (II) chloride in a solvent such as isopropyl alcohol/water. A compound of formula X may be prepared by reacting a compound of formula XI with YCH2C(O)OPg1 where Y is a suitable leaving group such the halogen bromo, and Pg1 is tert-butyl. The reaction is conveniently carried out with a phase transfer catalyst such as tetrabutylammonium chloride, and a base such as aqueous sodium hydroxide in a solvent such as dichloromethane. The resulting tert-butyl ester intermediate is treated with an acid such as hydrochloric acid to provide a compound of formula X. A compound of formula XI may be prepared by reacting a compound of formula XII with isopropylmagnesium chloride and benzyl azide in a solvent such as tetrahydrofuran. A compound of formula XII may be prepared by reacting 3-butyn-1-ol with dihydropyran in the presence of an organic acid such p-toluenesulfonic acid. The reaction is typically carried out in a solvent such as dichloromethane.

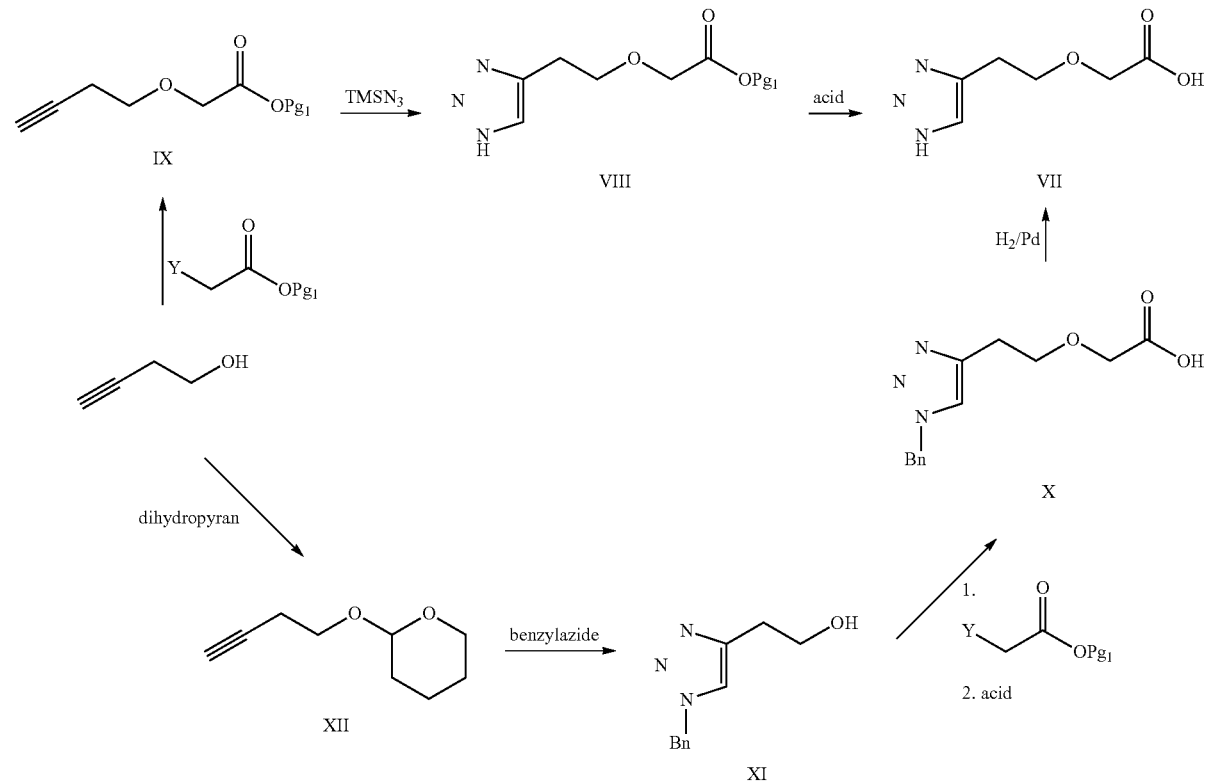

Scheme E

Preparation 1

Synthesis of 1-(2,3-dihydro-1H-inden-2-yl)guanidine hydrochloride

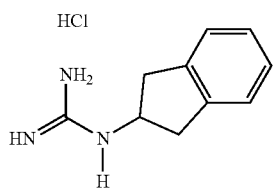 [SMILES: Cl ; N=C(N)NC1Cc2ccccc2C1]

Stir a solution of 2,3-dihydro-1H-inden-2-amine hydrochloride (197 g; 1.08 equiv; 1.16 moles), 1H-pyrazole-1-carboximidamide hydrochloride (158 g; 1.00 equiv; 1.08 moles) and diisopropylethylamine (400 g; 2.87 equiv; 3.09 moles; 539.74 mL) in acetonitrile (2 L) at 62° C. for 2 hours, during which time a white solid precipitates. Cool the mixture to 25° C., then filter and wash with 300 mL acetonitrile and 300 mL methyltert-butyl ether. Dry the product in air at 25° C. for 1 h to afford the title compound (200 g, 87%) as a white solid: MS (m/z): 176 (M+1).

Preparation 2

Synthesis of tert-butyl 2-(indan-2-ylamino)-7,8-dihydro-5H-pyrido[4,3-d]pyrimidine-6-carboxylate

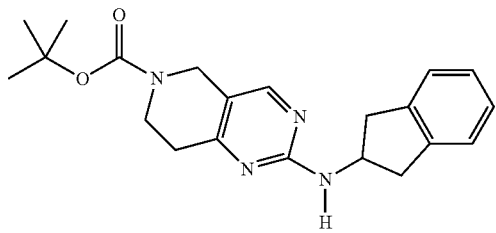 [SMILES: CC(C)(C)OC(=O)N1CCc2nc(NC3Cc4ccccc4C3)ncc2C1]

Stir a solution of 1,1-dimethoxy-N,N-dimethyl-methanamine (224 g; 2.15 equiv; 1.88 moles; 250.98 mL) and N-t-butoxycarbonyl-4-piperidone (250 g; 1.44 equiv; 1.25 moles) in dimethylformamide (1.2 L) at 109° C. under $N_2$ for 4 h. Cool the mixture to 25° C. and then add ethanol (700 mL; 12.02 moles; 553.91 g). Add 1-(2,3-dihydro-1H-inden-2-yl) guanidine hydrochloride (185 g; 1.00 equiv; 873.90 mmoles) and potassium carbonate (475 g; 3.44 moles) to the mixture at 25° C. in one portion to form a white suspension. Stir the mixture at 80-90° C. for 24 h, then cool to 25° C. and pour the mixture into 5 L ice/water to get a yellow suspension. Extract with ethyl acetate (3×3 L), and wash the organic layer with 10% lithium chloride solution (3 L), water (3 L), and saturated sodium chloride solution (3 L). Dry over anhydrous sodium sulfate, filter and concentrate to give about 300 ml of a red solution. Filter the solution through a silica gel plug (10 cm height, 5 cm diameter) and then concentrate to dryness to give the title compound as a red gel (320 g, 100%): MS (m/z): 367 (M+1).

Preparation 3

Synthesis of N-indan-2-yl-5,6,7,8-tetrahydropyrido[4,3-d]pyrimidin-2-amine

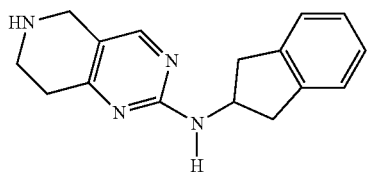 [SMILES: c1ccc2c(c1)CC(Nc1ncc3c(n1)CCNC3)C2]

Add portionwise hydrochloric acid (900 mL; 5M in water; 5.17 equiv; 4.50 mole; 1.08 kg) to a solution of tert-butyl 2-(indan-2-ylamino)-7,8-dihydro-5H-pyrido[4,3-d]pyrimidine-6-carboxylate (319 g; 1.00 equiv; 870.48 mmoles) in tetrahydrofuran (1.5 L). Once the addition is complete, stir the solution at 50° C. for 1 h. Cool the mixture to 25° C. and then add 3 L methyltert-butyl ether and 1 L water. Allow the solution to stand at 20° C. for 16 h. Separate the phases and extract the aqueous phase with dichloromethane (2 L). Discard the organic extracts and adjust the aqueous phase to pH 10 using 4M sodium hydroxide. Extract with ethyl acetate (3×3 L), and wash the combined organic extracts with saturated sodium chloride (2 L). Dry over anhydrous sodium sulfate, filter and concentrate to dryness to give a red gel. Redissolve the substance in ethyl acetate (300 mL) and petroleum ether (200 mL) at 50° C., and allow for precipitation over 24 hours. Filter and dry to afford the title compound (85 g, 37%). MS (m/z): 267 (M+1).

Preparation 4

Synthesis of 2-but-3-ynoxytetrahydropyran

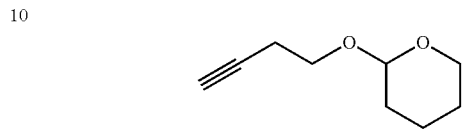

A solution of 3-butyn-1-ol (50 g, 1 equiv, 713 mmol), p-toluenesulfonic acid monohydrate (1.36 g, 0.01 equiv, 7.13 mmol), and dihydropyran (71.7 mL, 1.10 equiv, 785 mmol) in dichloromethane (500 mL) is stirred at 25° C. for 24 hours. Saturated sodium bicarbonate solution (500 mL) is then slowly added, and the mixture is extracted with dichloromethane (500 mL). The organic extract is dried over anhydrous sodium sulfate, filtered, and concentrated to afford the crude product, which is purified by vacuum distillation to afford the title compound (90 g, 82%): b.p.: 65° C., 1 mm Hg.

Preparation 5

Synthesis of 2-(3-benzyltriazol-4-yl)ethanol

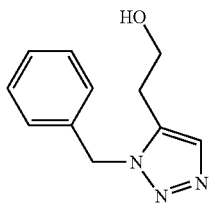 [SMILES: OCCc1cnnn1Cc1ccccc1]

Add isopropylmagnesium chloride (368 mL, 736.00 mmol) drop-wise to a solution of 2-but-3-ynoxytetrahydropyran (113.50 g, 736.00 mmol) in tetrahydrofuran (1.4 L) at 15° C., maintaining the internal temperature less than 20° C. Remove the ice-water bath, allow the temperature to warm to 25° C., and hold at that temperature for 20 min to ensure gas evolution is complete. Heat the reaction mixture to 30-35° C., and add benzyl azide (70 g, 525.71 mmol) drop-wise to the mixture over 2 h while ensuring benzyl azide concentration in the reaction mixture does not rise to appreciable levels by a method such as LCMS. After a 4 h stir, cool the reaction mixture to 25° C., and quench with saturated aqueous ammonium chloride (400 mL) via drop-wise addition. After a 16 h stir, dilute with methyltert-butyl ether (200 mL), separate the layers, and stir the organic layer with 3M hydrochloric acid (600 mL) for 4 h. When greater than 98% conversion is achieved by a method such as LCMS, raise the pH of the reaction mixture to pH>10 via dropwise addition of 6 M sodium hydroxide (ca. 350 mL). Extract the resulting mixture with methyltert-butyl ether (3×300 mL) and dichloromethane (3×300 mL). Concentrate the combined organic layers in vacuo, and purify the resulting crude product by silica gel column chromatography, eluting with ethyl acetate, to afford the title compound (53 g, 50%) as an off-white solid. MS (m/z): 204.1 (M+1).

Preparation 6

Synthesis of [2-(1-benzyl-1H-1,2,3-triazol-5-yl)ethoxy]acetic acid

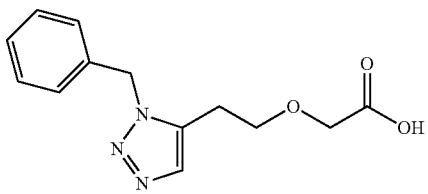 [SMILES: O=C(O)COCCc1cnnn1Cc1ccccc1]

Charge 400 mL of 40% w/w sodium hydroxide (5.73 mol) to a mixture of 2-(3-benzyltriazol-4-yl)ethanol (50 g, 246.01 mmol) and tetra-N-butylammonium chloride (6.84 g, 24.60 mmol) in dichloromethane (400 mL) at 0° C. Add bromo-1,1-dimethyl acetic acid ethyl ester (62.38 g, 319.81 mmol), and stir for 16 h, allowing the temp to rise to 25° C. Separate the layer, and extract the aqueous phase with dichloromethane (2×100 mL). Concentrate the combined organic layers in vacuo to give 75 g of the intermediate tert-butyl 2-(2-(3-benzyl-3H-1,2,3-triazol-4-yl)ethoxy)acetate as a yellow oil. Dilute the oil with 450 mL of toluene and 150 mL of 6 M hydrochloric acid, and stir at 25° C. for 16 h. Separate the layers and adjust the pH of the aqueous layer to ca. pH 2.0. Filter the resulting white solid, rinsing with water (2×200 mL) to give the title compound (58 g, 90%) as a white solid. MS (m/z): 262.1 (M+1).

Preparation 7

Synthesis of 2-[2-(1H-triazol-5-yl)ethoxy]acetic acid

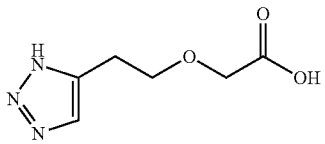 [SMILES: O=C(O)COCCc1cnn[nH]1]

Pressurize 1 atmosphere of hydrogen (g) to a flask containing [2-(1-benzyl-1H-1,2,3-triazol-5-yl)ethoxy]acetic acid (10.1 g; 1.00 equiv; 38.66 mmoles) and palladium (II) chloride (3 g; 16.92 mmoles; 3.00 g) in isopropyl alcohol (300 mL) and water (60 mL). Maintain the flask under a hydrogen atmosphere for 3 h, then filter through Celite™ and concentrate. Add toluene (2×50 mL) and concentrate to afford the title compound (7.96 g, 100%). $^1$H NMR (d$_6$-DMSO): 2.86 (t, J=7 Hz, 2H), 3.65 (t, J=7 Hz, 2H), 3.98 (s, 2H), 7.77 (s, 1H), 13.4-13.6 (br s, 2H).

Example 1

Synthesis of 1-[2-(2,3-dihydro-1H-inden-2-ylamino)-7,8-dihydropyrido[4,3-d]pyrimidin-6(5H)-yl]-2-[2-(1H-1,2,3-triazol-4-yl)ethoxy]ethanone

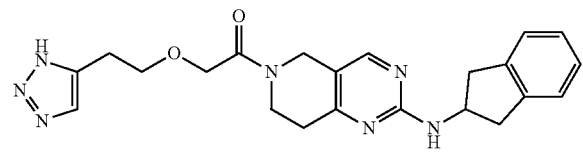 [SMILES: O=C(COCCc1cnn[nH]1)N1CCc2nc(NC3Cc4ccccc4C3)ncc2C1]

Add N-indan-2-yl-5,6,7,8-tetrahydropyrido[4,3-d]pyrimidin-2-amine (4.2 g, 15.8 mmol) to a mixture of 2-[2-(1H-triazol-5-yl)ethoxy]acetic acid (2.7 g, 15.8 mmol), 1-hydroxybenzotriazole (3.20 g, 23.7 mmol), and dimethylaminopropyl)-3-ethylcarbodiimide hydrochloride (5.44 g, 28.4 mmol) in dichloromethane (40 mL) at 25° C. Add triethylamine (4.40 mL, 31.6 mmol) to the reaction mixture and stir for 16 h. Wash with water (2×50 mL) and concentrate the organic layer. Purify by silica gel column chromatography, eluting with ethyl acetate/methanol, to give the title compound (4.0 g, 60%) as a solid. MS (m/z): 420 (M+H).

Preparation 8

Synthesis of 2-chloro-1-[2-(2,3-dihydro-1H-inden-2-ylamino)-7,8-dihydropyrido[4,3-d]pyrimidin-6(5H)-yl]ethanone

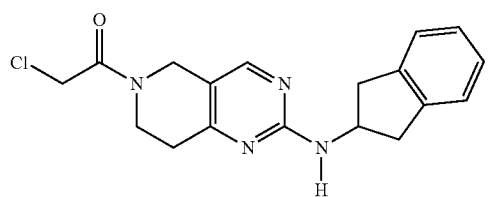 [SMILES: O=C(CCl)N1CCc2nc(NC3Cc4ccccc4C3)ncc2C1]

To N-indan-2-yl-5,6,7,8-tetrahydropyrido[4,3-d]pyrimidin-2-amine (11.0 g, 41.3 mmol) and triethylamine (7.48 mL, 53.7 mmol) in dichloromethane (200 mL), add 2-chloroacetyl chloride (3.61 mL, 5.13 g, 45.4 mmol) dropwise over five minutes at 23° C. Stir for 30 minutes and pour the reaction mixture into 1:1 50% saturated aqueous sodium bicarbonate:dichloromethane (75 mL). Separate the organic layer from the aqueous layer and further extract the aqueous layer with dichloromethane (2×25 mL). Combine the organic extracts and dry over anhydrous sodium sulfate, filter, and concentrate. Dissolve the residue in chloroform (10 mL) and purify via silica gel column chromatography (gradient elution: 25% ethyl acetate in hexanes to 100% ethyl acetate) to give the title compound (9.75 g, 69%). $^1$H NMR (CDCl$_3$, *=minor amide rotamer) δ 2.77* (t, 2H), 2.84 (dd, 2H), 2.87 (t, 2H), 3.35 (dd, 2H), 3.76 (t, 2H), 3.85* (t, 2H), 4.12 (s, 2H), 4.52* (s, 2H), 4.57 (s, 2H), 4.72-4.82 (m, 1H), 5.48-5.64 (m, 1H), 7.12-7.21 (m, 4H), 8.03-8.10 (m, 1H).

Preparation 9

Synthesis of 2-(but-3-yn-1-yloxy)-1-[2-(2,3-dihydro-1H-inden-2-ylamino)-7,8-dihydropyrido[4,3-d]pyrimidin-6(5H)-yl]ethanone

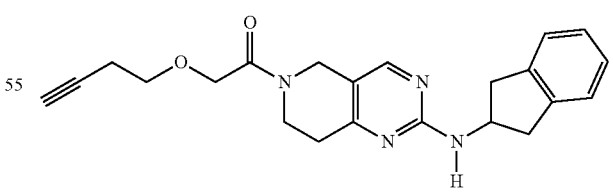

To sodium hydride (60 wt % in mineral oil, 1.58 g, 39.6 mmol) in tetrahydrofuran (50 mL) at 23° C., add 3-butyn-1-ol (7.93 g, 8.59 mL, 113.2 mmol) dropwise, then stir at 23° C. for 20 minutes. Add this solution to 2-chloro-1-[2-(2,3-dihydro-1H-inden-2-ylamino)-7,8-dihydropyrido[4,3-d]pyrimidin-6(5H)-yl]ethanone (9.70 g, 28.3 mmol) in tetrahydrofuran (150 mL) at 23° C. and stir for one hour. Pour the reaction mixture into 50% saturated aqueous sodium bicarbonate solution. Separate the organic layer and further extract the aqueous layer with ethyl ether (×2) and ethyl acetate (×2). Combine the organic extracts and wash with brine, then dry over anhydrous sodium sulfate, filter, and concentrate. Purify the resulting crude product by silica gel column chromatography (gradient elution: 20% ethyl acetate in hexanes to 100% ethyl acetate) to give the title compound (8.16 g, 77%). MS (m/z): 377 (M+1).

Example 1A

Alternative synthesis of 1-[2-(2,3-dihydro-1H-inden-2-ylamino)-7,8-dihydropyrido[4,3-d]pyrimidin-6(5H)-yl]-2-[2-(1H-1,2,3-triazol-4-yl)ethoxy]ethanone

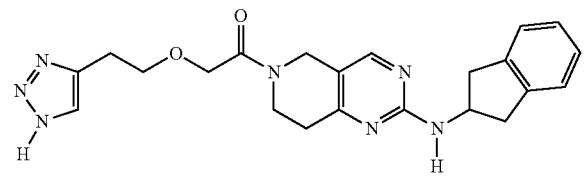 [SMILES: O=C(COCCc1c[nH]nn1)N1CCc2nc(NC3Cc4ccccc4C3)ncc2C1]

Sparge a solution of 2-(but-3-yn-1-yloxy)-1-[2-(2,3-dihydro-1H-inden-2-ylamino)-7,8-dihydropyrido[4,3-d]pyrimidin-6(5H)-yl]ethanone (8.15 g, 21.7 mmol) and L-ascorbic acid sodium salt (8.58 g, 43.3 mmol) in dimethylformamide (60 mL) and water (60 mL) with nitrogen for ten minutes, then evacuate and backfill with nitrogen three times. Add copper (II) sulfate pentahydrate (1.08 g, 4.33 mmol) and heat to 90° C., then add azidotrimethylsilane (23.1 mL, 20.0 g, 173 mmol) dropwise and stir for one hour. Cool reaction mixture to 23° C. and pour into water (50 mL). Extract this mixture with ethyl acetate (4×50 mL). Combine the organic extracts and wash with saturated aqueous sodium chloride, dry over anhydrous sodium sulfate, filter, and concentrate. Purify the resulting crude product by silica gel column chromatography (gradient elution: 0 to 10% methanol in ethyl acetate) to give the title compound (3.60 g, 40%). MS (m/z): 420 (M+1).

Preparation 10

Synthesis of tert-butyl-2-(2,3-dihydro-1H-inden-2-ylamino)-5,7-dihydro-6H-pyrrolo[3,4-d]pyrimidine-6-carboxylate

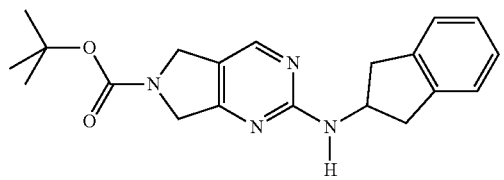 [SMILES: CC(C)(C)OC(=O)N1Cc2cnc(NC3Cc4ccccc4C3)nc2C1]

Charge 450 mL (2.58 mol) of N-ethyl-N-isopropylpropan-2-amine into a 15° C. solution of tert-butyl 2-chloro-5,7-dihydro-6H-pyrrolo[3,4-d]pyrimidine-6-carboxylate (220 g, 860.37 mmol) and 2,3-dihydro-1H-inden-2-amine (137.7 g, 1.03 mol) in 1-methylpyrrolidin-2-one (3.6 L). Heat the resulting mixture to 80° C. for 16 h, then cool to 30° C. and transfer the resulting mixture into 5 L of water at 25° C. Filter the resulting solid and rinse the filter cake with water (2×300 mL). Reslurry the solid in ethyl acetate (350 mL) for 45 min at 15° C. Filter the slurry, rinsing with 15° C. ethyl acetate (2×250 mL), and dry to give the title compound (226 g, 75%) as an off-white solid. $^1$H NMR (d$_6$-DMSO) 1.45 (s, 9H), 2.87 (dd, J=7.2, 15.8 Hz, 2H), 3.24 (dd, J=7.2, 15.8 Hz, 2H), 4.36 (d, 10.4 Hz, 2H), 4.44 (d, J=12.8 Hz, 2H), 4.60 (m, 1H), 7.14 (m, 2H), 7.20 (m, 2H), 7.55 (d, J=6.8 Hz, 1H), 8.27 (d, J=7.2 Hz, 1H).

Preparation 11

Synthesis of N-(2,3-dihydro-1H-inden-2-yl)-6,7-dihydro-5H-pyrrolo[3,4-d]pyrimidin-2-amine dihydrochloride hydrate

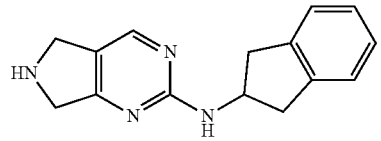

Charge 670 mL of 5 M hydrochloric acid (3.35 mol) to a solution of tert-butyl 2-(2,3-dihydro-1H-inden-2-ylamino)-5,7-dihydro-6H pyrrolo[3,4-d]pyrimidine-6-carboxylate (226 g, 641.25 mmol) in tetrahydrofuran (2.0 L) at 17° C., maintaining the internal temperature below 26° C. during the addition. Heat the resulting solution to 50° C. for 16 h, cool to 25° C. and dilute with 500 mL of water and 500 mL of tert-butylmethylether. Separate the resulting layers and extract with tert-butylmethylether (3×1 L). Concentrate the water phase down to a reaction volume of ca. 200 mL, and filter the resulting slurry. Rinse the cake with tert-butylmethylether (2×200 mL) and dry to give the title product (177 g, 80%) as a light brown solid. MS (m/z): 253.2 (M−2HCl—H$_2$O+1).

Preparation 12

Synthesis of tert-butyl 2-but-3-ynoxyacetate

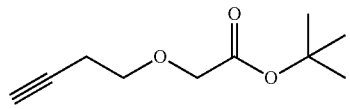

Stir a mixture of but-3-yn-1-ol (6.00 g; 85.60 mmol), tetrabutylammonium sulfate (2.07 g; 8.54 mmol) and sodium hydroxide (40% wt/wt; 150 mL) in dichloromethane (150 mL) at 0° C. Add tert-butyl bromoacetate (19.34 mL; 128.40 mmol) dropwise and stir the mixture for 2.5 hours at room temperature. Dilute the reaction mixture with dichloromethane (200 mL) and water (100 mL), separate the layers, and further extract the aqueous layer with dichloromethane (2×100 mL). Wash the combined organic layers with brine (100 mL), dry over anhydrous sodium sulfate, and concentrate to afford the crude title compound as a brown oil (11.93 g). Purify the oil by silica gel column chromatography, eluting with hexane:ethyl acetate (0% to 10% mixtures) to give the title compound (11.35 g; 72%) as a colorless oil. $^1$H NMR (CDCl$_3$) δ 1.48 (s, 9H), 2.00 (m, 1H), 2.52 (m, 2H), 3.67 (m, 2H), 4.01 (bs, 2H).

Preparation 13

Synthesis of tert-butyl 2-[2-(1H-triazol-5-yl)ethoxy]acetate

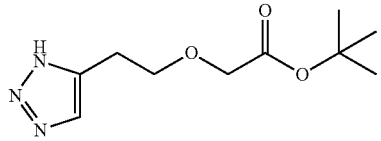 [SMILES: CC(C)(C)OC(=O)COCCc1cnn[nH]1]

Stir tert-Butyl 2-but-3-ynoxyacetate (11.34 g; 61.55 mmol) and copper(I)iodide (584 mg; 3.07 mmol) in a mixture of dimethylformamide (56.70 mL) and methanol (11.34 mL) at 0° C. Add azido(trimethyl)silane (12.33 mL; 86.47 mmol) dropwise and heat the mixture at 90° C. for 18 hours.

In a second batch, stir tert-butyl 2-but-3-ynoxyacetate (4.38 g; 23.77 mmol) and copper(I)iodide (226 mg; 1.19 mmol) in a mixture of dimethylformamide (22 mL) and methanol (6 mL) at 0° C. Add azido(trimethyl)silane (4.8 mL; 33.66 mmol) dropwise and the mixture heated at 90° C. for 18 hours.

Upon cooling to room temperature, combine the crude products from both batches and concentrate the mixture to afford a greenish residue. Purify the crude product by filtration through a plug of silica eluting with dichloromethane:ethyl acetate (75% to 100% mixtures) to afford the title compound (14.15 g, 73%) as a colorless oil. MS (m/z): 228.15 (M+1).

Preparation 14

Synthesis of 2-[2-(1H-triazol-5-yl)ethoxy]acetic acid 2,2,2-trifluoroacetic acid

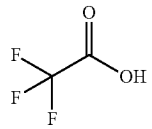

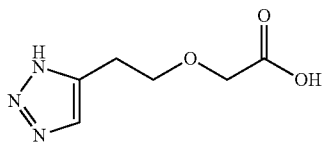

Stir a mixture of tert-butyl 2-[2-(1H-triazol-5-yl)ethoxy]acetate (14.15 g; 62.26 mmol) and trifluoroacetic acid (70.75 mL, 935.69 mmol) in dichloromethane (70.75 mL) for 2 hours at room temperature. Concentrate the reaction mixture under reduced pressure to provide the title compound containing additional trifluoroacetic acid (20.22 g, >100%) as a brown solid. MS (m/z): 172.05 (M+1).

Example 2

Synthesis of 1-[2-(2,3-dihydro-1H-inden-2-ylamino)-5,7-dihydro-6H-pyrrolo[3,4-d]pyrimidin-6-yl]-2-[2-(1H-1,2,3-triazol-4-yl)ethoxy]ethanone

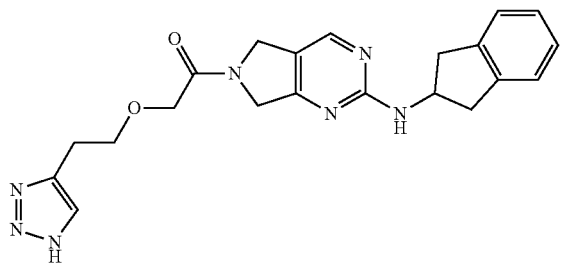 [SMILES: O=C(COCCc1c[nH]nn1)N1Cc2cnc(NC3Cc4ccccc4C3)nc2C1]

Stir a mixture of 2-[2-(1H-triazol-5-yl)ethoxy]acetic acid 2,2,2-trifluoroacetic acid (20.22 g; 70.90 mmol), N-(2,3-dihydro-1H-inden-2-yl)-6,7-dihydro-5H-pyrrolo[3,4-d]pyrimidin-2-amine dihydrochloride hydrate (27.99 g; 81.54 mmol) and triethylamine (98.83 mL; 709.03 mmol) in dimethylformamide (404.40 mL) at 0° C. Add a solution of 1-propanephosphonic acid cyclic anhydride (50% solution in DMF; 51.89 mL; 81.54 mmol) over 30 minutes, and stir the mixture at room temperature for 18 hours.

Concentrate the reaction mixture under reduced pressure to give a residue. Add water (200 mL) and extract the mixture with ethyl acetate (4×250 mL) and dichloromethane (4×250 mL). Wash the combined organic layers with saturated aqueous sodium bicarbonate (2×100 mL) and brine (100 mL), then dry over anhydrous sodium sulfate. Filter the mixture and concentrate the solution under reduced pressure to give a red solid (25.70 g) that is slurried in ethyl acetate/methanol (9:1 mixture; 200 mL) for 2 hours at room temperature. Filter the resulting solid and wash with cold ethyl acetate (50 mL) to give a solid (ca.18.2 g) that is re-slurried in ethyl acetate (200 mL) at reflux for 1 hour. On cooling to room temperature, stir the mixture for 1 hour and filter the resulting light pink solid.

Slurry the light pink solid in water/methanol (1:1 mixture; 200 mL) and heat the mixture at 50° C. for 30 minutes. Add ammonium hydroxide solution (32%; 50 mL) and continue to heat the mixture at 50° C. for 30 minutes. Upon cooling to room temperature, add additional ammonium hydroxide solution (32%; 50 mL) and continue stirring for 1 hour at room temperature. Filter the resulting light gray solid, dry and slurry again in ethyl acetate (200 mL) for 1 hour to afford a light gray solid that is filtered, washed with ethyl acetate (25 mL), and dried to give the title compound (12.42 g; 43%) as a gray solid. MS (m/z): 406 (M+1).

Preparation 15

Synthesis of 2-chloro-1-[2-(2,3-dihydro-1H-inden-2-ylamino)-5,7-dihydro-6H-pyrrolo[3,4-d]pyrimidin-6-yl]ethanone

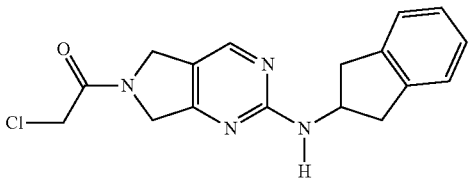 [SMILES: O=C(CCl)N1Cc2cnc(NC3Cc4ccccc4C3)nc2C1]

Stir a suspension of N-(2,3-dihydro-1H-inden-2-yl)-6,7-dihydro-5H-pyrrolo[3,4-d]pyrimidin-2-amine dihydrochloride hydrate (14.4 g, 41.9 mmol) and triethylamine (14.3 g, 19.7 mL, 141.4 mmol) in dichloromethane (200 mL) at 23° C. for 10 minutes, then cool to −30° C. Add 2-chloroacetyl chloride (5.49 g, 3.86 mL, 48.6 mmol) over two minutes and warm to 23° C. over 10 minutes. Add methanol (5 mL) and remove the solvent in vacuo. Slurry the crude reaction mixture in methanol (30 mL), add 50 g silica gel and remove solvent in vacuo. Load the resulting residue onto a loading column and purify via silica gel column chromatography (gradient elution: 50% ethyl acetate in hexanes to ethyl acetate to 10% methanol in ethyl acetate) to give the title compound (11.5 g, 84%). MS (m/z): 329(M+1).

Preparation 16

Synthesis of 2-(but-3-yn-1-yloxy)-1-[2-(2,3-dihydro-1H-inden-2-ylamino)-5,7-dihydro-6H-pyrrolo[3,4-d]pyrimidin-6-yl]ethanone

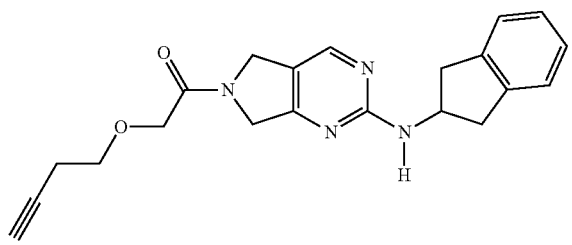 [SMILES: C#CCCOCC(=O)N1Cc2cnc(NC3Cc4ccccc4C3)nc2C1]

To sodium hydride (60 wt % in mineral oil, 2.06 g, 51.4 mmol) in tetrahydrofuran (86 mL) at 0° C., add 3-butyn-1-ol (4.64 g, 5.03 mL, 64.3 mmol), then stir at 23° C. for 15 minutes. Add this solution to 2-chloro-1-[2-(2,3-dihydro-1H-inden-2-ylamino)-5,7-dihydro-6H-pyrrolo[3,4-d]pyrimidin-6-yl]ethanone (8.45 g, 25.7 mmol) in tetrahydrofuran (86 mL) at 0° C. and stir for five minutes. Pour reaction mixture into 50% saturated aqueous sodium bicarbonate solution. Separate the organic layer and further extract the aqueous layer with ethyl ether and ethyl acetate (2×50 mL each). Combine the organic extracts and wash with brine, then dry over anhydrous sodium sulfate, filter, and concentrate. Combine the crude product with the crude product from a second reaction (run reaction under identical conditions and stoichiometry employing 2-chloro-1-[2-(indan-2-ylamino)-5,7-dihydropyrrolo[3,4-d]pyrimidin-6-yl]ethanone (3.0 g, 9.1 mmol)) and purify by silica gel column chromatography (gradient elution: 25% ethyl acetate in hexanes to 100% ethyl acetate) to give the title compound (2.90 g, 23%). MS (m/z): 363(M+1).

Example 2A

Alternative synthesis of 1-[2-(2,3-dihydro-1H-inden-2-ylamino)-5,7-dihydro-6H-pyrrolo[3,4-d]pyrimidin-6-yl]-2-[2-(1H-1,2,3-triazol-4-yl)ethoxy]ethanone

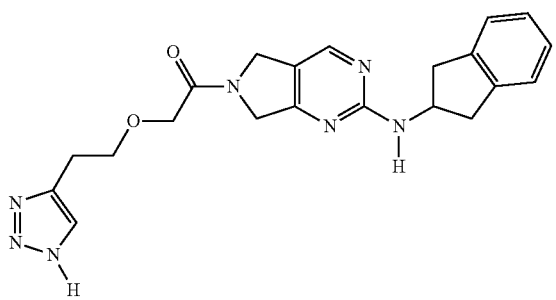 [SMILES: O=C(COCCc1c[nH]nn1)N1Cc2cnc(NC3Cc4ccccc4C3)nc2C1]

Add dimethylformamide (27 mL) and water (27 mL) to a flask containing 2-(but-3-yn-1-yloxy)-1-[2-(2,3-dihydro-1H-inden-2-ylamino)-5,7-dihydro-6H-pyrrolo[3,4-d]pyrimidin-6-yl]ethanone (2.90 g, 8.00 mmol). Add copper (II) sulfate pentahydrate (400 mg, 1.60 mmol) and L-ascorbic acid sodium salt (3.17 g, 16.0 mmol). Evacuate flask and backfill with nitrogen (×2), then add azidotrimethylsilane (7.37 g, 8.53 mL, 64.0 mmol) and heat the reaction to 90° C. for 70 minutes. Cool the reaction mixture to 23° C. and remove all solvent in vacuo. Suspend the residue in methanol/dichloromethane and then add silica gel and remove solvent in vacuo. Load this material onto a loading column and purify via silica gel column chromatography (gradient elution: 0-9% methanol in ethyl acetate) to give the title compound (980 mg, 30%). MS (m/z): 406(M+1).

Scheme F

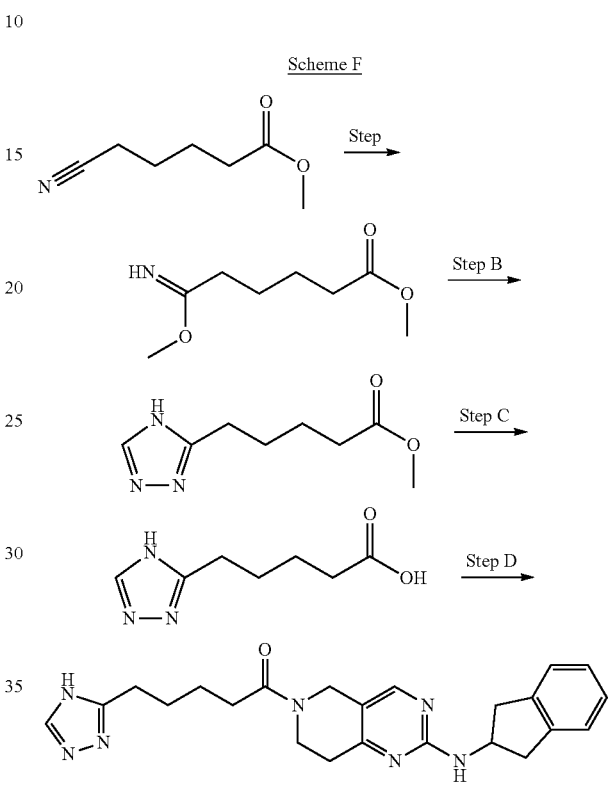

Preparation 17

Synthesis of methyl 6-imino-6-methoxy-hexanoate

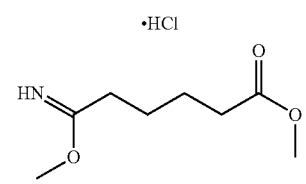

Scheme F, Step A.

Bubble hydrogen chloride (g) through a 0° C. solution of 5-cyano-pentanoic acid methyl ester (3.0 mL; 1.00 equiv; 22.02 mmoles) in methanol (5 mL), and ethyl ether (10 mL) for 1 hour. Allow the solution to warm to room temperature then add 50 mL ethyl ether, stir vigorously for 15 minutes, then filter and collect the resulting precipitate. Wash the solid with ethyl ether to afford methyl 6-imino-6-methoxy-hexanoate (3.82 g; 83%): $^1$H NMR (DMSO) δ 1.47-1.62 (m, 4H), 2.31 (t, 2H), 2.59 (t, 2H), 3.56 (s, 3H), 4.03 (s, 3H).

Preparation 18

Synthesis of methyl 5-(4H-1,2,4-triazol-3-yl)pentanoate

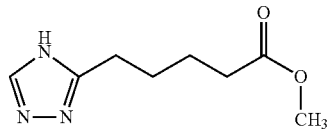

Scheme F, Step B.

Add methanol (1 mL) and triethylamine (0.36 mL; 1.0 equiv; 2.58 mmoles) to a vial containing methyl 6-imino-6-methoxy-hexanoate (0.542 g; 1.00 equiv; 2.58 mmoles), followed by a solution of formylhydrazine (0.155 g 1.0 equiv; 2.58 mmoles) in methanol (3 mL). Stir at room temperature for 18 hours, then heat to 70° C. for 3 hours. Concentrate the mixture, then dilute with ethyl acetate (30 mL) and filter. Concentrate the filtrate to afford methyl 5-(4H-1,2,4-triazol-3-yl)pentanoate (0.498 g; 105%) as a colorless oil: MS (m/z): 184 (M+1).

Preparation 18a

Synthesis of 5-(4H-1,2,4-triazol-3-yl)pentanoic acid

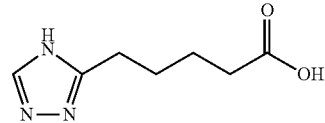 [SMILES: O=C(O)CCCCc1nnc[nH]1]

Scheme F, Step C.

Add methanol (3 mL), tetrahydrofuran (3 mL), and water (2 mL) to a flask containing methyl 5-(4H-1,2,4-triazol-3-yl)pentanoate (0.5 g; 1.0 equiv; 2.73 mmoles). Add lithium hydroxide (0.261 g; 4.0 equiv; 10.92 mmoles) in one portion, and stir at room temperature for 90 minutes. Cool the solution to 0° C. and add 5N hydrogen chloride (2.18 mL; 4.0 equiv; 10.92 mmoles) slowly. Concentrate the mixture and then azeotrope the residue with toluene (4×10 mL). Add dichloromethane (30 mL) followed by magnesium sulfate. Filter, and rinse the filter cake with 100 mL 10% ethanol in dichloromethane. Concentrate to provide 5-(4H-1,2,4-triazol-3-yl)pentanoic acid (1.6 g; >100%) as an alcoholic adduct: MS (m/z): 170 (M+1).

Example 3

Synthesis of 1-[2-(2,3-dihydro-1H-inden-2-ylamino)-7,8-dihydropyrido[4,3-d]pyrimidin-6(5H)-yl]-5-(4H-1,2,4-triazol-3-yl)pentan-1-one

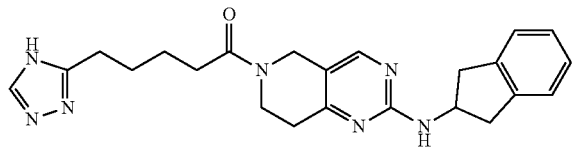 [SMILES: O=C(CCCCc1nnc[nH]1)N1CCc2nc(NC3Cc4ccccc4C3)ncc2C1]

Scheme F, Step D.

Add N-indan-2-yl-5,6,7,8-tetrahydropyrido[4,3-d]pyrimidin-2-amine (0.189 g; 1.0 equiv; 0.71 mmoles) to a solution containing 5-(4H-1,2,4-triazol-3-yl)pentanoic acid (0.40 g 1.0 equiv; 0.71 mmoles), followed by dimethylformamide (2 mL). Stir the resulting solution at room temperature until homogeneous. Add 4-pyridinamine, N,N-dimethyl-(0.017 g; 0.2 equiv; 0.141 mmoles), and cool the solution to 0° C. Add 1-(3-dimethylaminopropyl)-3-ethylcarbodiimide hydrochloride (0.204 g; 1.5 equiv; 1.06 mmoles) in one portion. Allow the mixture to warm to room temperature and stir for 30 minutes. Add dichloromethane (2 mL), heat to 40° C., and stir for 24 hours. Dilute with 250 mL water and then 50 mL ethyl acetate. Extract the mixture with ethyl acetate (5×25 mL). Wash the combined organic extracts with brine (10 mL). Dry the organics over magnesium sulfate, filter, concentrate, and purify via column chromatography (hexanes to 12% methanol in ethyl acetate) to give 1-[2-(2,3-dihydro-1H-inden-2-ylamino)-7,8-dihydropyrido[4,3-d]pyrimidin-6(5H)-yl]-5-(4H-1,2,4-triazol-3-yl)pentan-1-one (0.08 g; 27% yield) as a white foam: MS (m/z): 418 (M+1).

Scheme G

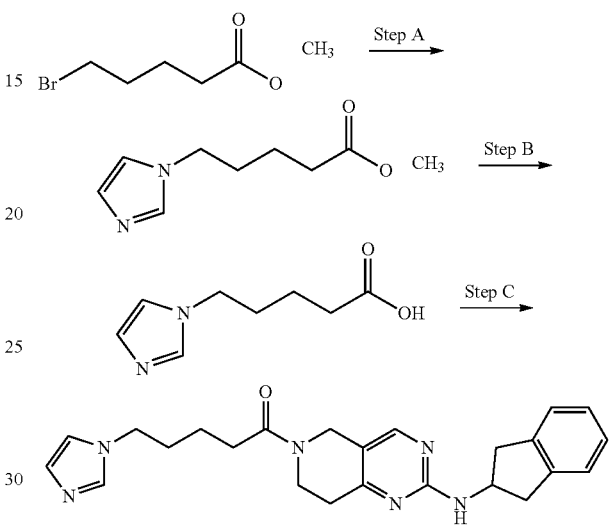

Preparation 19

Synthesis of methyl 5-imidazol-1-ylpentanoate

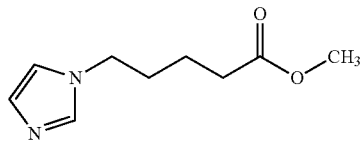

Scheme G, Step A.

Add sodium hydride (0.212 g; 1.2 equiv; 5.29 mmoles) to a solution of 1H-imidazole (0.30 g; 1.0 equiv; 4.41 mmoles) and methyl 5-bromopentanoate (1.03 g; 1.2 equiv; 5.29 mmoles) in dimethylformamide (20 mL). Stir the mixture for 18 hours then add water (15 mL). Extract the mixture with dichloromethane and wash with brine (20 mL). Dry the organic phase over sodium sulfate, filter, and concentrate to give the crude product, which is purified by column chromatography (0 to 10% methanol in dichloromethane) to afford methyl 5-imidazol-1-ylpentanoate (0.655 g; 82%) as a yellow oil: MS (m/z): 183(M+1).

Preparation 20

Synthesis of 5-imidazol-1-ylpentanoic acid

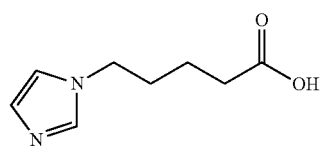 [SMILES: O=C(O)CCCCn1ccnc1]

Scheme G, Step B.

Stir a solution of methyl 5-imidazol-1-ylpentanoate (0.60 g; 1.0 equiv; 3.29 mmoles) and lithium hydroxide (0.553 g; 4 equiv; 13.17 mmoles) in tetrahydrofuran (20 mL) and water (15 mL) for 18 hours. Add 3 ml of 5N hydrochloric acid then concentrate the mixture. Purify the crude product by column chromatography (0 to 15% methanol in dichloromethane) to afford 5-imidazol-1-ylpentanoic acid (0.72 g; 19%) as a yellow oil: MS (m/z): 169(M+1).

Example 4

Synthesis of 1-[2-(2,3-dihydro-1H-inden-2-ylamino)-7,8-dihydropyrido[4,3-d]pyrimidin-6(5H)-yl]-5-(1H-imidazol-1-yl)pentan-1-one

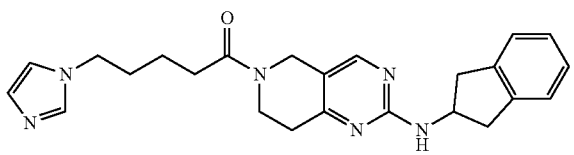 [SMILES: O=C(CCCCn1ccnc1)N1CCc2nc(NC3Cc4ccccc4C3)ncc2C1]

Scheme G, Step C.

Add 1-(3-dimethylaminopropyl)-3-ethylcarbodiimide hydrochloride (0.288 g; 2.0 equiv; 1.50 mmoles) to a solution of N-indan-2-yl-5,6,7,8-tetrahydropyrido[4,3-d]pyrimidin-2-amine (0.20 m; 1.0 equiv; 0.75 mmoles), 5-imidazol-1-ylpentanoic acid (0.152 g; 1.2 equiv; 0.90 mmoles), and 1-hydroxybenzotriazole (0.203 g; 2.0 equiv; 1.50 mmoles) in dichloromethane (20 mL) and triethylamine (0.52 mL). Stir the mixture for 18 hours, then concentrate, add water (10 mL), and extract with ethyl acetate (3×20 mL). Dry the combined organic extracts over anhydrous sodium sulfate, filter, and concentrate. Purify the crude product by column chromatography (0 to 10% methanol in dichloromethane) to afford 1-[2-(2,3-dihydro-1H-inden-2-ylamino)-7,8-dihydropyrido[4,3-d]pyrimidin-6(5H)-yl]-5-(1H-imidazol-1-yl)pentan-1-one (0.14 g; 45%) as a colorless oil: MS (m/z): 417 (M+1).

Preparation 21

Synthesis of 1-[2-(indan-2-ylamino)-7,8-dihydro-5H-pyrido[4,3-d]pyrimidin-6-yl]prop-2-en-1-one

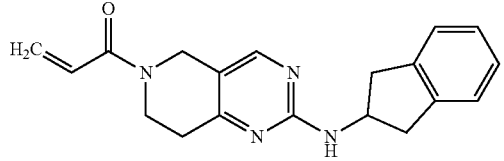 [SMILES: C=CC(=O)N1CCc2nc(NC3Cc4ccccc4C3)ncc2C1]

Scheme H, Step A.

Add triethylamine (0.82 mL; 2.0 equiv; 5.86 mmoles) followed by 2-propenoyl chloride (0.24 mL; 1.0 equiv; 2.93 mmoles) dropwise to a 0° C. solution of N-indan-2-yl-5,6,7, 8-tetrahydropyrido[4,3-d]pyrimidin-2-amine (0.781 g; 1.0 equiv; 2.93 mmoles) in dichloromethane (29 mL). Stir the solution for 16 hours at ambient temperature, then dilute with dichloromethane, wash with brine, dry over sodium sulfate, filter, and concentrate to an orange oil. Purify the crude product by column chromatography to afford 1-[2-(indan-2-ylamino)-7,8-dihydro-5H-pyrido[4,3-d]pyrimidin-6-yl] prop-2-en-1-one (0.66 g; 70%): MS (m/z): 321 (M+1).

Preparation 22

Synthesis of 1-[2-(2,3-dihydro-1H-inden-2-ylamino)-7,8-dihydropyrido[4,3-d]pyrimidin-6(5H)-yl]-3-(prop-2-yn-1-yloxy)propan-1-one

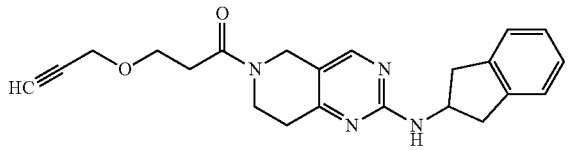 [SMILES: C#CCOCCC(=O)N1CCc2nc(NC3Cc4ccccc4C3)ncc2C1]

Scheme H, Step B.

Add 1,8-diazabicyclo[5.4.0]undec-7-ene (0.035 mL; 0.15 equiv; 0.23 mmoles) to a solution of 1-[2-(indan-2-ylamino)-7,8-dihydro-5H-pyrido[4,3-d]pyrimidin-6-yl]prop-2-en-1-one (0.5 g; 1.0 equiv; 1.56 mmoles) and 2-propyn-1-ol (5.0 mL; 55 equiv; 85.86 mmoles). Stir the reaction at ambient temperature for 16 hours, then heat to 50° C. for 36 hours. Concentrate the solution to a brown oil, then purify the crude Scheme H

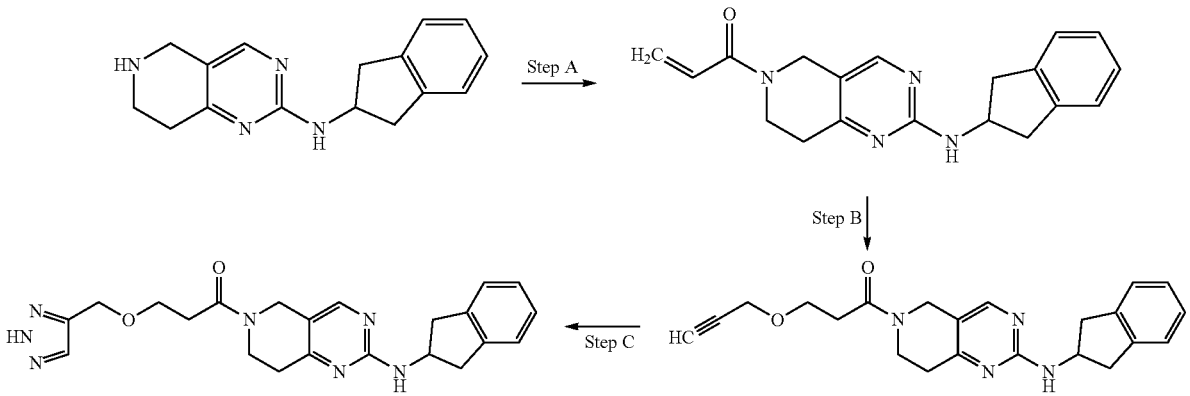

product by column chromatography (20 to 100% ethyl acetate in dichloromethane) to afford the desired 1-[2-(2,3-dihydro-1H-inden-2-ylamino)-7,8-dihydropyrido[4,3-d]pyrimidin-6(5H)-yl]-3-(prop-2-yn-1-yloxy)propan-1-one (0.28 g; 48%): MS (m/z): 377 (M+1).

Example 5

Synthesis of 1-[2-(2,3-dihydro-1H-inden-2-ylamino)-7,8-dihydropyrido[4,3-d]pyrimidin-6(5H)-yl]-3-(1H-1,2,3-triazol-4-ylmethoxy)propan-1-one

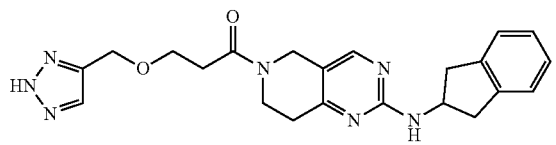 [SMILES: O=C(CCOCc1cn[nH]n1)N1CCc2nc(NC3Cc4ccccc4C3)ncc2C1]

Scheme H, Step C. Add copper(II) sulfate pentahydrate (0.037 g; 0.2 equiv; 0.147 mmoles) and L-ascorbic acid sodium salt (0.291 g; 2.0 equiv; 1.47 mmoles) to a solution of 1-[2-(2,3-dihydro-1H-inden-2-ylamino)-7,8-dihydropyrido[4,3-d]pyrimidin-6(5H)-yl]-3-(prop-2-yn-1-yloxy)propan-1-one (0.277 g; 1.0 equiv; 0.74 mmoles) in dimethylformamide (4 mL) and water (4 mL). Evacuate the system twice and backfill with nitrogen. Add azidotrimethylsilane (0.784 mL; 8.0 equiv; 5.89 mmoles) and heat the heterogeneous mixture to 90° C. for 1 hour. Dilute the reaction mixture with water (250 mL) and ethyl acetate (50 mL) and extract with ethyl acetate (3×50 mL). Wash the combined organic extracts with brine (30 mL), dry over sodium sulfate, filter, and concentrate in vacuo to a yellow/orange oil. Purify the crude product by column chromatography (ethyl acetate to 10% methanol in ethyl acetate) to afford the desired 1-[2-(2,3-dihydro-1H-inden-2-ylamino)-7,8-dihydropyrido[4,3-d]pyrimidin-6(5H)-yl]-3-(1H-1,2,3-triazol-4-ylmethoxy)propan-1-one (0.135 g; 44%): MS (m/z): 420 (M+1).

Scheme I

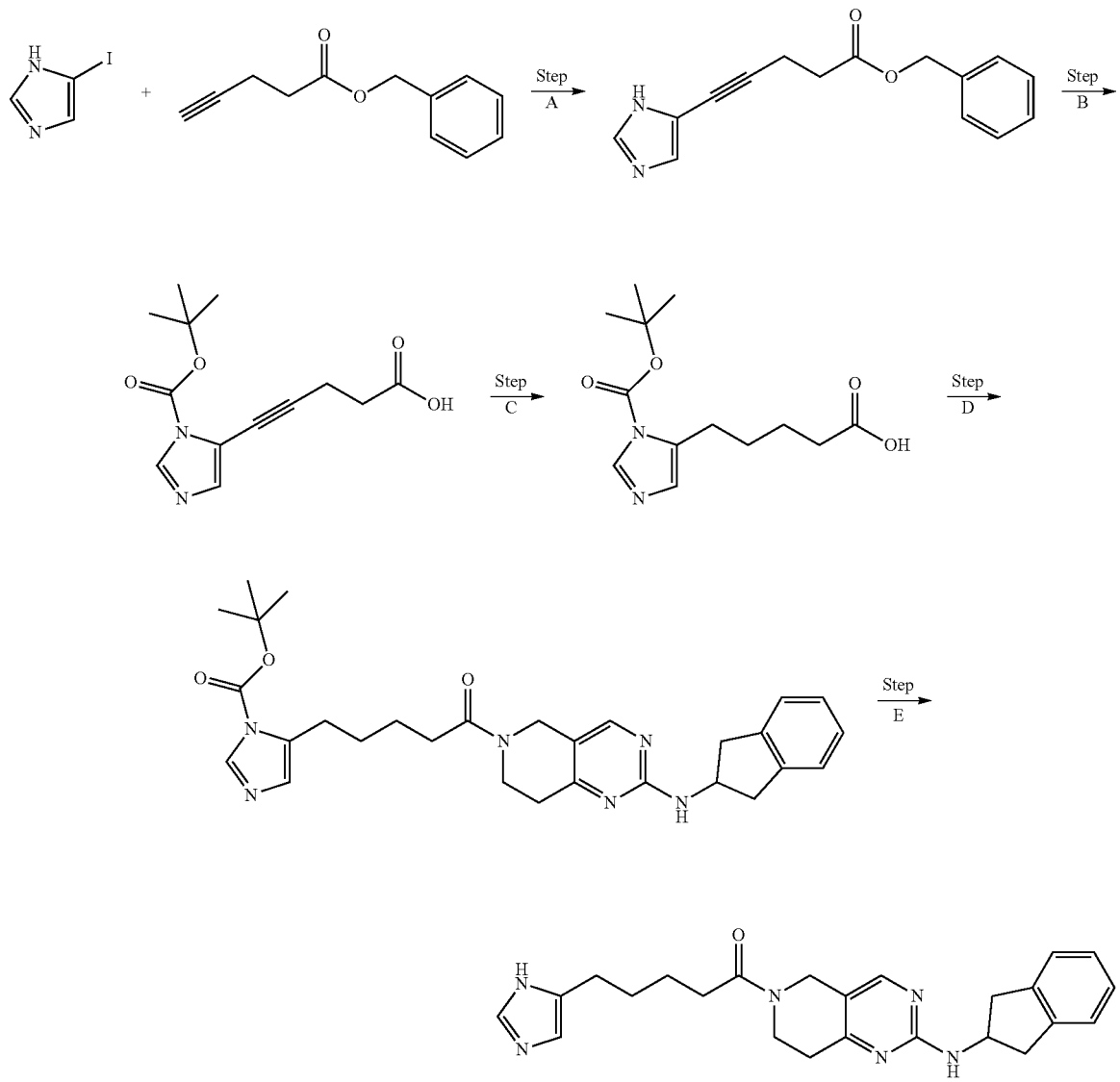

Preparation 23

Synthesis of benzyl 5-(1H-imidazol-5-yl)pent-4-ynoate

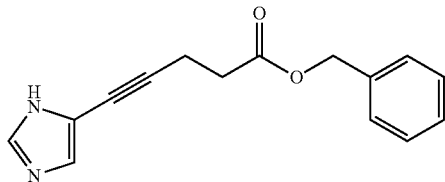 [SMILES: O=C(CCC#Cc1cnc[nH]1)OCc1ccccc1]

Scheme I, Step A.

Add bis(triphenylphosphine)palladium(II) chloride (0.14 g; 0.1 equiv; 0.20 mmoles) and copper(I) iodide (0.039 mg; 0.1 equiv; 0.20 mmoles) to a deoxygenated solution of 4-iodo-1H-imidazole (0.388 g; 1.0 equiv; 2.00 mmoles), benzyl pent-4-ynoate (0.376 g; 1.0 equiv; 2.00 mmoles), and triethylamine (0.84 mL; 3 equiv; 6.0 mmoles) in dimethylformamide (8 mL). Heat the mixture to 75° C. for 16 hours, then dilute the mixture with water (30 mL) and extract 3× with ethyl acetate. Wash the combined organic extracts with brine, dry over magnesium sulfate, filter, and concentrate to provide the crude product. Purify the crude product by column chromatography (0 to 10% methanol in dichloromethane) to afford benzyl 5-(1H-imidazol-5-yl)pent-4-ynoate (0.35 g; 69%) as a colorless oil: MS (m/z): 255(M+1).

Preparation 24

Synthesis of tert-butyl 5-(5-benzyloxy-5-oxo-pent-1-ynyl)imidazole-1-carboxylate

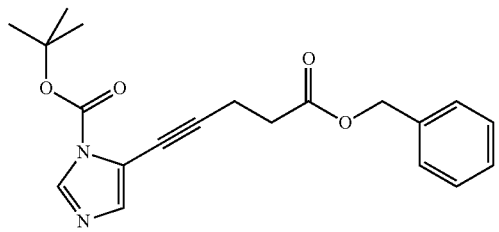 [SMILES: CC(C)(C)OC(=O)n1cncc1C#CCCC(=O)OCc1ccccc1]

Scheme I, Step B.

Stir a solution of benzyl 5-(1H-imidazol-5-yl)pent-4-ynoate (0.19 g; 1.00 equiv; 0.747 mmoles), di-t-butyldicarbonate (0.210 g; 1.29 equiv; 0.96 mmoles), triethylamine (0.21 mL; 2.0 equiv; 1.49 mmoles), and 4-pyridinamine, N,N-dimethyl-(9 mg; 0.1 equiv; 0.074 mmoles) in dichloromethane (10 mL) for 2 hr. Concentrate the solution and purify the crude product by column chromatography (25% ethyl acetate in hexanes) to afford tert-butyl 5-(5-benzyloxy-5-oxo-pent-1-ynyl)imidazole-1-carboxylate (0.170 g; 64%) as a white solid: MS (m/z): 299 (M-t-Bu+1).

Preparation 25

Synthesis of 5-(3-tert-butoxycarbonylimidazol-4-yl)pentanoic acid

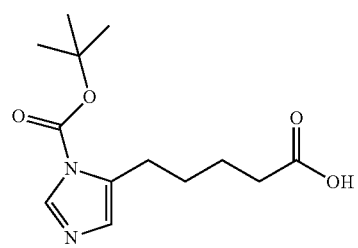 [SMILES: CC(C)(C)OC(=O)n1cncc1CCCCC(=O)O]

Scheme I, Step C.

Vigorously stir a 60° C. solution of tert-butyl 5-(5-benzyloxy-5-oxo-pent-1-ynyl)imidazole-1-carboxylate (0.17 g; 1.0 equiv; 0.48 mmoles) and palladium (10% on carbon; 0.030 g; 0.014 mmoles) in methanol (13 mL) under 1 atmosphere of hydrogen for 16 hours. Filter and concentrate to afford the desired 5-(3-tert-butoxycarbonylimidazol-4-yl) pentanoic acid (0.128 g; 99%) as a white solid: MS (m/z): 213(M-t-Bu+1).

Preparation 26

Synthesis of tert-butyl 5-[5-[2-(indan-2-ylamino)-7,8-dihydro-5H-pyrido[4,3-d]pyrimidin-6-yl]-5-oxo-pentyl]imidazole-1-carboxylate

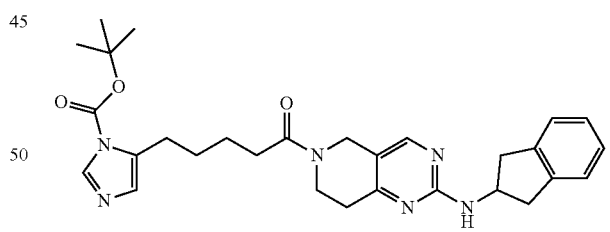

Scheme I, Step D.

Add 1-(3-dimethylaminopropyl)-3-ethylcarbodiimide hydrochloride (0.092 g; 1.5 equiv; 0.48 mmoles) to a solution of 5-(3-tert-butoxycarbonylimidazol-4-yl)pentanoic acid (0.084 g; 1.0 equiv; 0.31 mmoles), N-indan-2-yl-5,6,7,8-tetrahydropyrido[4,3-d]pyrimidin-2-amine (0.064 g; 0.77 equiv; 0.24 mmoles), 1-hydroxybenzotriazole (0.065 g; 1.5 equiv; 0.48 mmoles), and triethylamine (0.20 mL; 4.5 equiv; 1.44 mmoles) in dichloromethane (15 mL). Heat the mixture to 40° C. for 16 hours. Concentrate the mixture, and then purify the crude product by column chromatography (0 to 10% methanol in dichloromethane) to afford tert-butyl 5-[5-[2-(indan-2-ylamino)-7,8-dihydro-5H-pyrido[4,3-d]pyrimidin-6-yl]-5-oxo-pentyl]imidazole-1-carboxylate (0.040 g; 25%) as a white solid: MS (m/z): 517 (M+1).

Example 6

Synthesis of 1-[2-(2,3-dihydro-1H-inden-2-ylamino)-7,8-dihydropyrido[4,3-d]pyrimidin-6(5H)-yl]-5-(1H-imidazol-4-yl)pentan-1-one

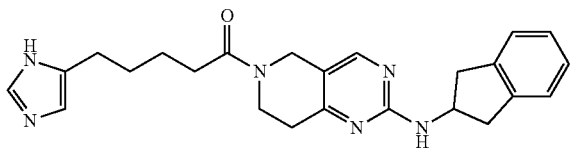 [SMILES: O=C(CCCCc1cnc[nH]1)N1CCc2nc(NC3Cc4ccccc4C3)ncc2C1]

Scheme I, Step E.

Add trifluoroacetic acid (1.5 mL) to a solution of tert-butyl 5-[5-[2-(indan-2-ylamino)-7,8-dihydro-5H-pyrido[4,3-d]pyrimidin-6-yl]-5-oxo-pentyl]imidazole-1-carboxylate (0.030 g; 0.058 mmoles) in dichloromethane (8 mL). Stir the reaction at room temperature for 2 hr. Concentrate the mixture and add saturated sodium bicarbonate (10 mL) and water (20 mL), then extract with dichloromethane (3×20 mL). Wash the combined organic extracts with brine, dry over sodium sulfate, filter, and concentrate. Purify the crude product by column chromatography (0 to 10% methanol in dichloromethane) to afford 1-[2-(2,3-dihydro-1H-inden-2-ylamino)-7,8-dihydropyrido[4,3-d]pyrimidin-6(5H)-yl]-5-(1H-imidazol-4-yl)pentan-1-one (0.020 g; 83%) as a white solid: MS (m/z): 417 (M+1).

Scheme J

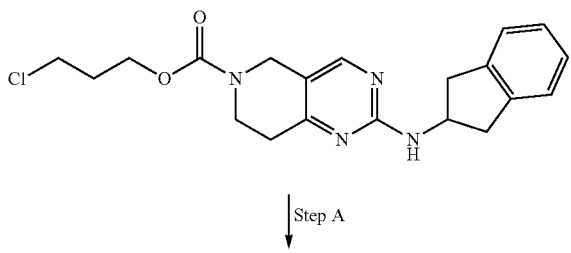

Step A

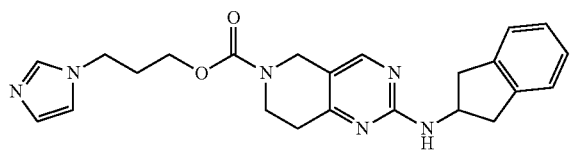

Example 7

Synthesis of 3-(1H-imidazol-1-yl)propyl 2-(2,3-dihydro-1H-inden-2-ylamino)-7,8-dihydropyrido[4,3-d]pyrimidine-6(5H)-carboxylate

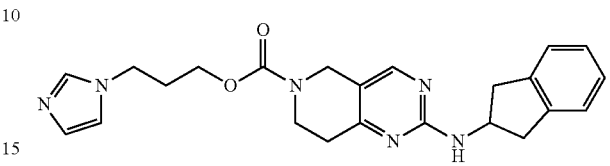

Scheme J, Step A.

Add sodium hydride (0.050 g; 2.2 equiv; 1.25 mmoles) to a solution of 3-chloropropyl 2-(indan-2-ylamino)-7,8-dihydro-5H-pyrido[4,3-d]pyrimidine-6-carboxylate (0.22 g; 1.0 equiv; 0.57 mmoles) and 1H-imidazole (0.082 g; 2.1 equiv; 1.20 mmoles) in dimethylformamide (2 mL) and stir for 18 hours. Dilute the reaction with dichloromethane and water. Separate the layers and further extract the aqueous layer with dichloromethane (2×). Dry the combined organic extracts with sodium sulfate, filter, and concentrate. Purify the crude product by column chromatography (0 to 10% methanol in dichloromethane) to afford the desired 3-(1H-imidazol-1-yl)propyl 2-(2,3-dihydro-1H-inden-2-ylamino)-7,8-dihydropyrido[4,3-d]pyrimidine-6(5H)-carboxylate (0.078 g; 33%) as a white solid: MS (m/z): 419 (M+1).

Scheme K

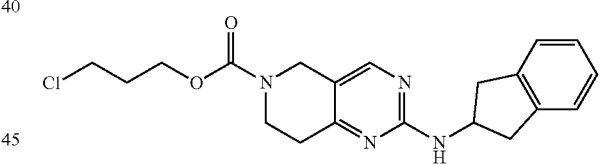

Step A

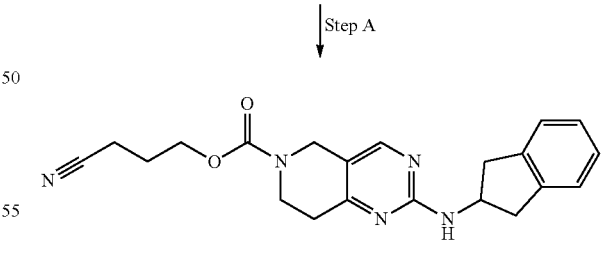

Step B

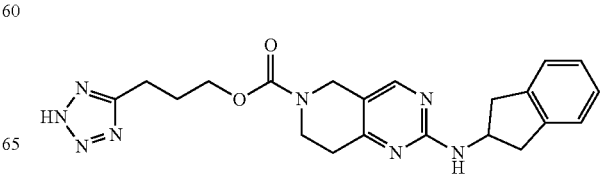

Preparation 27

Synthesis of 3-cyanopropyl 2-(2,3-dihydro-1H-inden-2-ylamino)-7,8-dihydropyrido[4,3-d]pyrimidine-6(5H)-carboxylate

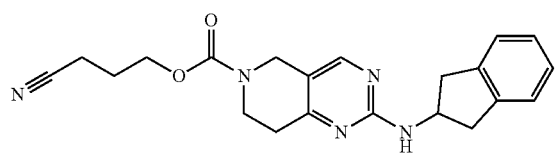 [SMILES: N#CCCCOC(=O)N1CCc2nc(NC3Cc4ccccc4C3)ncc2C1]

Scheme K, Step A.

Heat a solution of 3-chloropropyl 2-(indan-2-ylamino)-7,8-dihydro-5H-pyrido[4,3-d]pyrimidine-6-carboxylate (0.42 g; 1.0 equiv; 1.09 mmoles) and and sodium cyanide (0.085 g; 1.6 equiv; 1.73 mmoles) in dimethylformamide (3 mL) to 100° C. for 2 hours. Cool the mixture to ambient temperature, dilute with dichloromethane (20 mL) and wash the reaction mixture with water (25 mL). Extract the aqueous layer with dichloromethane (2×20 mL). Dry the combined organic extracts over sodium sulfate, filter, and concentrate to afford crude product. Combine the crude product and purify by column chromatography (0 to 10% methanol in dichloromethane) to afford 3-cyanopropyl 2-(2,3-dihydro-1H-inden-2-ylamino)-7,8-dihydropyrido[4,3-d]pyrimidine-6(5H)-carboxylate as a light brown oil and used in next step. MS (m/z): 378 (M+1).

Example 8

Preparation of 3-(1H-tetrazol-5-yl)propyl 2-(2,3-dihydro-1H-inden-2-ylamino)-7,8-dihydropyrido[4,3-d]pyrimidine-6(5H)-carboxylate

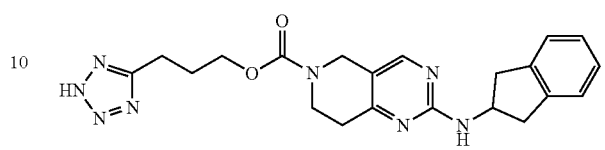

Scheme K, Step B.

Heat a solution of 3-cyanopropyl 2-(2,3-dihydro-1H-inden-2-ylamino)-7,8-dihydropyrido[4,3-d]pyrimidine-6(5H)-carboxylate (0.24 g; 1.0 equiv; 0.64 mmoles), azidotrimethylsilane (0.85 mL; 10 equiv; 6.38 mmoles) and dibutyloxostannane (0.040 g; 0.25 equiv; 0.16 mmoles) in toluene (5 mL) to 100° C. for 24 hours, then cool to ambient temperature and concentrate. Purify the crude material by reverse phase chromatography to afford impure product. Dissolve the impure product in 50 mL dichloromethane and wash with saturated sodium bicarbonate, and further extract the aqueous layer 2× dichloromethane. Dry the combined organic extracts over sodium sulfate, filter, and concentrate to afford 3-(1H-tetrazol-5-yl)propyl 2-(2,3-dihydro-1H-inden-2-ylamino)-7,8-dihydropyrido[4,3-d]pyrimidine-6(5H)-carboxylate (0.110 g; 41%) as a yellow solid: MS (m/z): 421 (M+1).

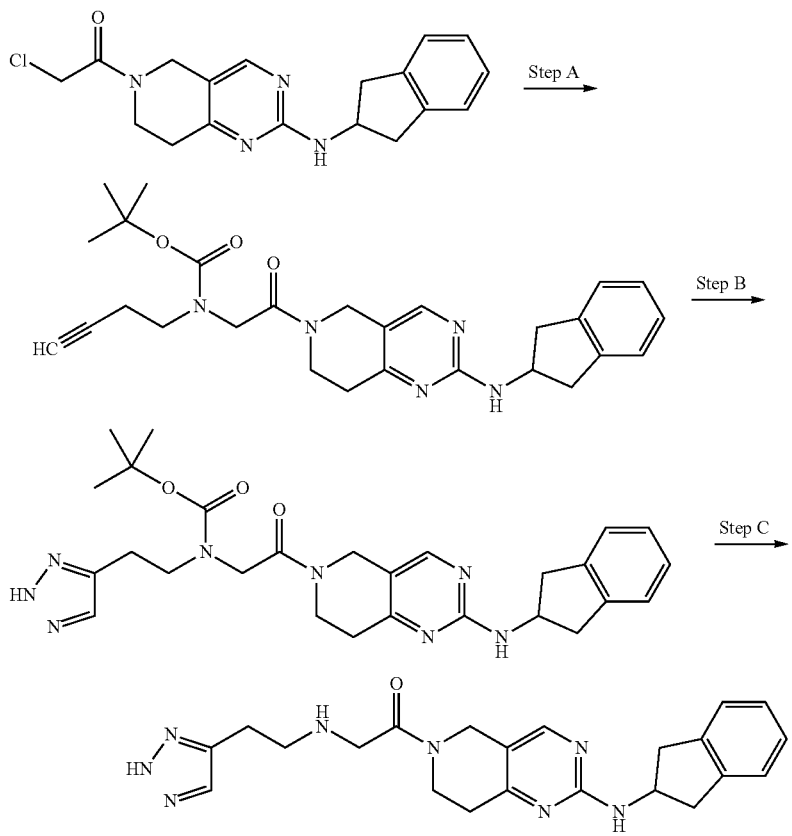

Scheme L

Preparation 28

Synthesis of tert-butyl N-but-3-ynyl-N-[2-[2-(indan-2-ylamino)-7,8-dihydro-5H-pyrido[4,3-d]pyrimidin-6-yl]-2-oxo-ethyl]carbamate

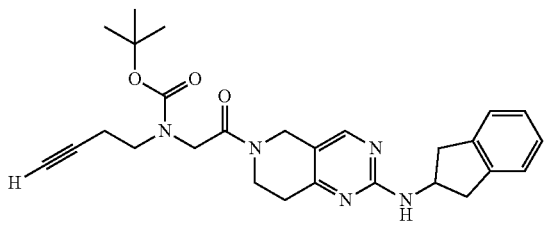 [SMILES: C#CCCN(CC(=O)N1CCc2nc(NC3Cc4ccccc4C3)ncc2C1)C(=O)OC(C)(C)C]

Scheme L, Step A.

Add but-3-yn-1-amine (2.71 g; 8 equiv; 9.80 mmoles) quickly to a 0° C. solution of 2-chloro-1-[2-(2,3-dihydro-1H-inden-2-ylamino)-7,8-dihydropyrido[4,3-d]pyrimidin-6(5H)-yl]ethanone (0.42 g; 1.0 equiv; 1.23 mmoles) in triethylamine (0.205 mL; 1.2 equiv; 1.47 mmoles) in tetrahydrofuran (8 mL). After 15 minutes, heat the solution to 45° C. for 2 hours, then concentrate the mixture and redissolve the residue in dichloromethane (3 mL). Add di-t-butyl-dicarbonate (0.802 g; 3 equiv; 3.68 mmoles) and stir at ambient temperature for 1 hour. Concentrate the mixture and purify the crude product by column chromatography (0 to 100% ethyl acetate/hexanes) to give tert-butyl N-but-3-ynyl-N-[2-[2-(indan-2-ylamino)-7,8-dihydro-5H-pyrido[4,3-d]pyrimidin-6-yl]-2-oxo-ethyl]carbamate (0.504 g; 87%) as a white solid: MS (m/z): 476 (M+1).

Preparation 29

Synthesis of tert-butyl {2-[2-(2,3-dihydro-1H-inden-2-ylamino)-7,8-dihydropyrido[4,3-d]pyrimidin-6(5H)-yl]-2-oxoethyl}[2-(1H-1,2,3-triazol-4-yl)-ethyl]carbamate

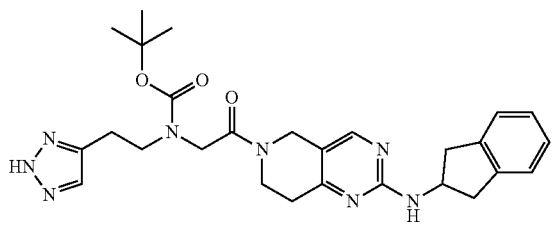 [SMILES: CC(C)(C)OC(=O)N(CCc1cn[nH]n1)CC(=O)N1CCc2nc(NC3Cc4ccccc4C3)ncc2C1]

Scheme L, Step B.

Add copper(II)sulfate pentahydrate (0.026 g; 0.2 equiv; 0.106 mmoles) and L-ascorbic acid sodium salt (0.21 g; 2.0 equiv; 1.06 mmoles) to a deoxygenated solution of tert-butyl N-but-3-ynyl-N-[2-[2-(indan-2-ylamino)-7,8-dihydro-5H-pyrido[4,3-d]pyrimidin-6-yl]-2-oxo-ethyl]carbamate (0.252 g; 1.0 equiv; 0.53 mmoles) in dimethylformamide (6 mL) and water (3 mL) (including toluene (0.05 mL) as an internal standard). Heat the reaction vessel to 90° C. and then add azidotrimethylsilane (0.565 mL; 8 equiv; 4.24 mmoles) slowly. Stir at 90° C. for 4 hours, then dilute the reaction mixture with water (100 mL) and ethyl acetate (50 mL), and extract 3×50 mL ethyl acetate. Wash the combined organic extracts with brine, dry over magnesium sulfate, filter, and concentrate. Purify the crude product by column chromatography (0 to 10% methanol in ethyl acetate) to give tert-butyl {2-[2-(2,3-dihydro-1H-inden-2-ylamino)-7,8-dihydropyrido[4,3-d]pyrimidin-6(5H)-yl]-2-oxoethyl}[2-(1H-1,2,3-triazol-4-yl)-ethyl]carbamate (0.174 g; 63%) as a colorless foam: MS (m/z): 519 (M+1).

Example 9

Synthesis of 1-[2-(2,3-dihydro-1H-inden-2-ylamino)-7,8-dihydropyrido[4,3-d]pyrimidin-6(5H)-yl]-2-{[2-(1H-1,2,3-triazol-4-yl)-ethyl]amino}ethanone

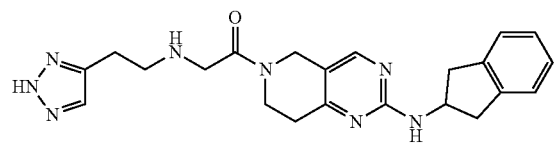 [SMILES: O=C(CNCCc1cn[nH]n1)N1CCc2nc(NC3Cc4ccccc4C3)ncc2C1]

Scheme L, Step C.

Add hydrogen chloride (1M in ethyl ether; 2.55 mL; 8 equiv; 2.55 mmoles) to a 0° C. solution of tert-butyl {2-[2-(2,3-dihydro-1H-inden-2-ylamino)-7,8-dihydropyrido[4,3-d]pyrimidin-6(5H)-yl]-2-oxoethyl}[2-(1H-1,2,3-triazol-4-yl)ethyl]carbamate (0.165 g; 1.0 equiv; 0.318 mmoles) in dichloromethane (2 mL) and methanol (1 mL). After stirring for 1 hour at 0° C., concentrate the mixture. Redissolve the crude product in a 10:1 mixture of dichloromethane:methanol and wash with saturated sodium bicarbonate. Extract the aqueous layer with additional 10:1 mixtures of dichloromethane:methanol (4×). Dry the combined organic extracts over magnesium sulfate, filter, and concentrate to afford 1-[2-(2,3-dihydro-1H-inden-2-ylamino)-7,8-dihydropyrido[4,3-d]pyrimidin-6(5H)-yl]-2-{[2-(1H-1,2,3-triazol-4-yl)ethyl]amino}ethanone (0.136 g; 102%) as a brown foam: MS (m/z): 419 (M+1).

Scheme M

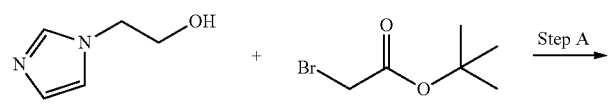

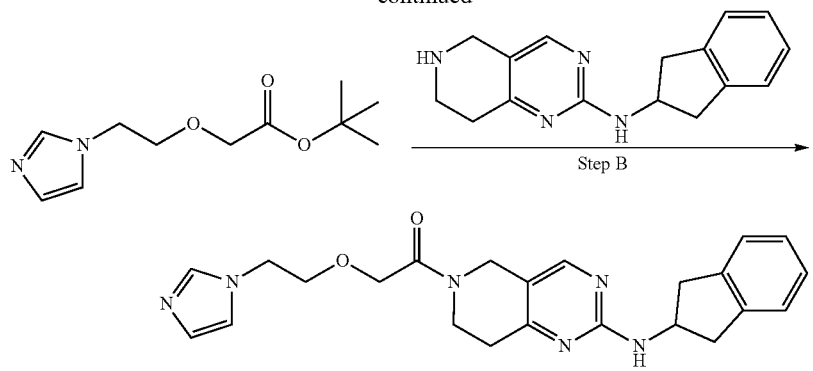

Preparation 30

Synthesis of tert-butyl 2-(2-imidazol-1-ylethoxy)acetate

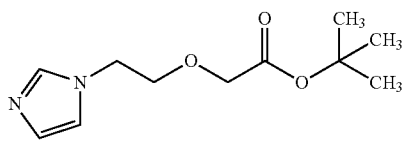 [SMILES: CC(C)(C)OC(=O)COCCn1ccnc1]

Scheme M, Step A.

Add sodium hydride (0.79 g; 1.1 equiv; 19.75 mmoles) slowly to a 0° C. solution of 1H-imidazole-1-ethanol (2.01 g; 1.0 equiv; 17.93 mmoles) in tetrahydrofuran (90 mL). Stir for 1 hour, then add acetic acid, bromo-, 1,1-dimethylethyl ester (4.03 mL; 1.49 equiv; 26.76 mmoles) dropwise at 0° C. Warm the solution to ambient temperature and stir for 3 hours, then add 250 mL saturated aqueous sodium bicarbonate solution. Extract the mixture with dichloromethane (3×150 mL). Wash the combined organic extracts with brine (100 mL), dry over sodium sulfate, filter, and concentrate to afford the crude product. Purify this residue by column chromatography (0 to 20% methanol in dichloromethane) to afford tert-butyl 2-(2-imidazol-1-ylethoxy)acetate (0.85 g; 21%) as a viscous yellow-brown oil: MS (m/z): 227(M+1).

Example 10

Synthesis of 1-[2-(2,3-dihydro-1H-inden-2-ylamino)-7,8-dihydropyrido[4,3-d]pyrimidin-6(5H)-yl]-2-[2-(1H-imidazol-1-yl)ethoxy]ethanone

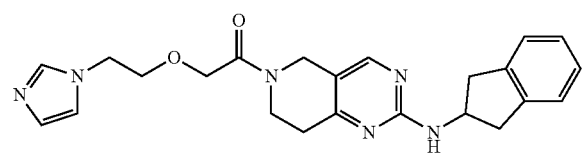 [SMILES: O=C(COCCn1ccnc1)N1CCc2nc(NC3Cc4ccccc4C3)ncc2C1]

Scheme M, Step B.

Add trifluoroacetic acid (2 mL) dropwise to a solution of tert-butyl 2-(2-imidazol-1-ylethoxy)acetate (0.375 g; 1.0 equiv; 1.66 mmoles) in dichloromethane (10 mL). Stir at room temperature for 4 hours and then concentrate the mixture. Redissolve the remaining residue in dimethylformamide (5 mL) and add diisopropylethylamine (1.45 mL; 5 equiv; 8.31 mmoles) followed by N-indan-2-yl-5,6,7,8-tetrahydro-pyrido[4,3-d]pyrimidin-2-amine (0.44 g; 1.0 equiv; 1.65 mmoles). Add O-(7-azabenzotriazol-1-yl)-N,N,N',N'-tetramethyluronium hexafluorophosphate (0.69 g; 1.1 equiv; 1.81 mmoles) and stir at room temperature for 16 hours. Pour the reaction mixture into saturated aqueous sodium bicarbonate solution (200 mL) and extract with dichloromethane (2×200 mL). Wash the combined organic extracts with saturated aqueous sodium bicarbonate solution (100 mL), dry over sodium sulfate, filter, and concentrate to give the crude product. Purify this residue by column chromatography (0 to 20% methanol in dichloromethane) to afford 1-[2-(2,3-dihydro-1H-inden-2-ylamino)-7,8-dihydropyrido[4,3-d]pyrimidin-6(5H)-yl]-2-[2-(1H-imidazol-1-yl)ethoxy]ethanone (0.152 g; 22%) as a light brown solid: MS (m/z): 419(M+1).

Scheme N

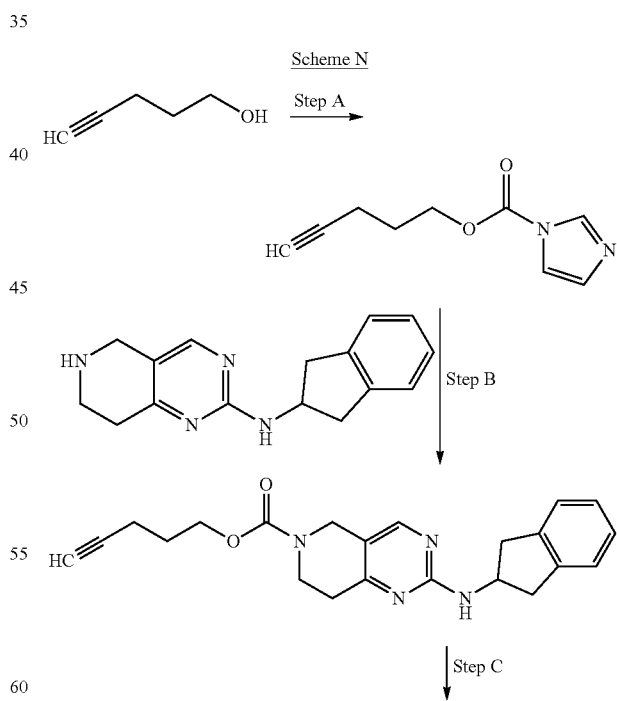

Preparation 31

Synthesis of pent-4-yn-1-yl 2-(2,3-dihydro-1H-inden-2-ylamino)-7,8-dihydropyrido[4,3-d]pyrimidine-6(5H)-carboxylate

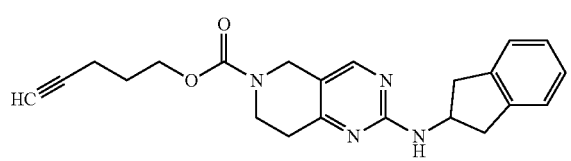 [SMILES: C#CCCCOC(=O)N1CCc2nc(NC3Cc4ccccc4C3)ncc2C1]

Scheme N, Steps A and B.

Add 1,1'-carbonyldiimidazole (0.936 g; 5.66 mmoles) slowly dropwise to a −78° C. solution of 4-pentyn-1-ol (0.50 mL; 5.39 mmoles) in dichloromethane (18 mL). Allow the reaction to warm to ambient temperature for 30 minutes, then add half of this solution to a solution of N-indan-2-yl-5,6,7,8-tetrahydropyrido[4,3-d]pyrimidin-2-amine (0.581 g; 1.05 equiv; 2.18 mmoles), 4-pyridinamine, N,N-dimethyl-(0.258 g; 1.0 equiv; 2.08 mmoles), and triethylamine (0.58 mL; 2.0 equiv; 4.15 mmoles). Warm the resulting pale yellow solution to ambient temperature and stir for 16 hours, then warm to 40° C. for an additional 24 hours. Cool the reaction mixture to ambient temperature and load directly onto a silica gel column. Purify by column chromatography (20 to 100% ethyl acetate in dichloromethane) to afford pent-4-yn-1-yl 2-(2,3-dihydro-1H-inden-2-ylamino)-7,8-dihydropyrido[4,3-d]pyrimidine-6(5H)-carboxylate (0.76 g; 88%): MS (m/z): 377 (M+1).

Example 11

Synthesis of 3-(1H-1,2,3-triazol-4-yl)propyl 2-(2,3-dihydro-1H-inden-2-ylamino)-7,8-dihydropyrido[4,3-d]pyrimidine-6(5H)-carboxylate

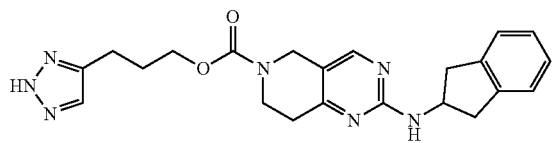 [SMILES: O=C(OCCCc1cn[nH]n1)N1CCc2nc(NC3Cc4ccccc4C3)ncc2C1]

Scheme N, Step C.

Add copper(II)sulfate pentahydrate (0.090 g; 0.2 equiv; 0.36 mmoles) and L-ascorbic acid sodium salt (0.714 g; 2.0 equiv; 3.61 mmoles) to a deoxygenated solution of pent-4-yn-1-yl 2-(2,3-dihydro-1H-inden-2-ylamino)-7,8-dihydropyrido[4,3-d]pyrimidine-6(5H)-carboxylate (0.754 g; 1.0 equiv; 1.80 mmoles) in dimethylformamide (15 mL) and water (15 mL). Add azidotrimethylsilane (1.92 mL; 8 equiv; 14.42 mmoles) and heat the reaction to 90° C. for 3 hours. Dilute the reaction mixture with water (250 mL) and ethyl acetate. Extract the mixture with ethyl acetate (3×50 mL). Wash the combined organic extracts with water (3×) and brine, dry over sodium sulfate, filter, and concentrate to a tan/orange oil. Purify the crude product by column chromatography (0 to 5% methanol in dichloromethane) to afford 3-(1H-1,2,3-triazol-4-yl)propyl 2-(2,3-dihydro-1H-inden-2-ylamino)-7,8-dihydropyrido[4,3-d]pyrimidine-6(5H)-carboxylate (0.26 g; 35%): MS (m/z): 420(M+1).

Scheme O

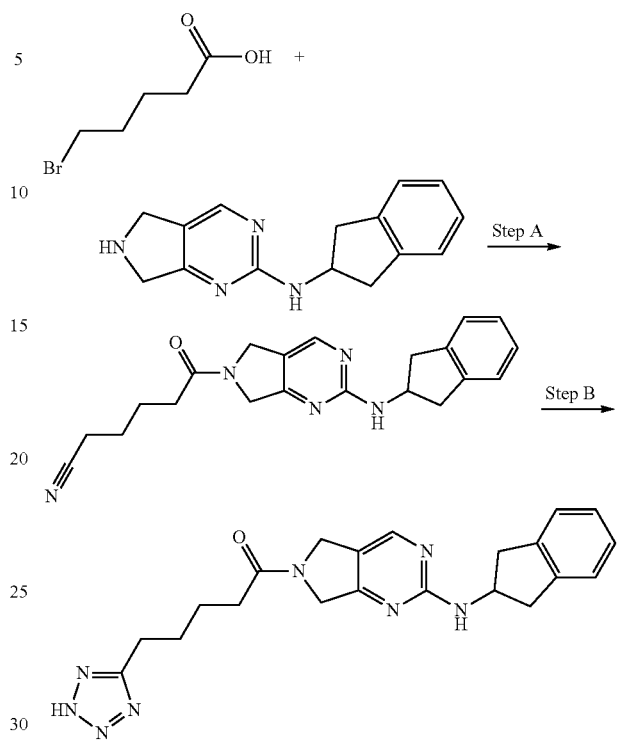

Preparation 32

Synthesis of 6-[2-(indan-2-ylamino)-5,7-dihydropyrrolo[3,4-d]pyrimidin-6-yl]-6-oxo-hexanenitrile

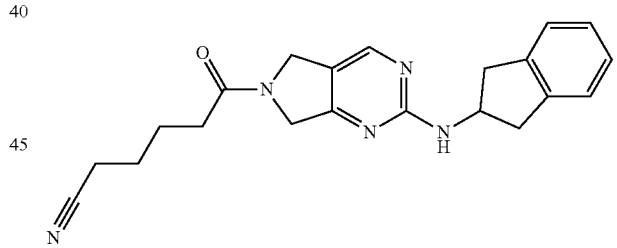

Scheme O, Step A.

Add 1-(3-dimethylaminopropyl)-3-ethylcarbodiimide hydrochloride (1.33 g; 1.15 equiv; 6.94 mmoles) to a flask charged with N-(2,3-dihydro-1 h-inden-2-yl)-6,7-dihydro-5H-pyrrolo[3,4-d]pyrimidin-2-amine dihydrochloride hydrate (1.96 g; 1.0 equiv; 6.03 mmoles) and 5-bromovaleric acid (1.4 g; 1.25 equiv; 7.50 mmoles) in dichloromethane (25 mL). Stir the resulting reaction for 2 h, then directly concentrate the mixture. Partition the residue between water and dichloromethane, and concentrate the organic extract. Purify the crude material by column chromatography (70 to 90% ethyl acetate/hexanes) to afford the intermediate 5-bromovaleramide (0.66 g), which is dissolved in dimethylformamide (10 mL). Add sodium cyanide (0.128 g; 2.48 mmol) and heat the resulting mixture to 100° C. for 3 hours then cool to ambient temperature. Partition the reaction mixture between ethyl acetate and water, and separate. Extract the aqueous layer with ethyl acetate (2×100 mL), and wash the combined organic extracts with 1 N hydrochloric acid followed by brine. Dry the combined organic extracts over sodium sulfate, filter, and concentrate to afford the crude product. Purify the crude product by column chromatography (5 to 10% methanol in dichloromethane) to provide 6-[2-(indan-2-ylamino)-5,7-dihydropyrrolo[3,4-d]pyrimidin-6-yl]-6-oxo-hexanenitrile (0.0772 g; 4%): MS (m/z): 362(M+1).

Example 12

Synthesis of 1-[2-(2,3-dihydro-1H-inden-2-ylamino)-5,7-dihydro-6H-pyrrolo[3,4-d]pyrimidin-6-yl]-5-(1H-tetrazol-5-yl)pentan-1-one

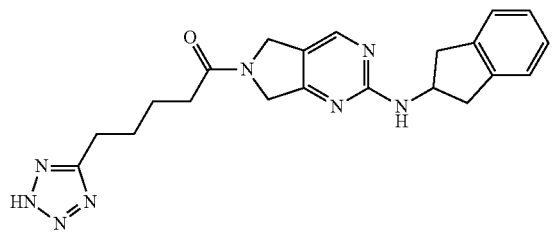

Scheme O, Step B.

Add dibutyloxostannane (0.071 g; 1.33 equiv; 0.29 mmoles) and azidotrimethylsilane (1.6 mL; 56 equiv; 12.01 mmoles) to a stirred solution of 6-[2-(indan-2-ylamino)-5,7-dihydropyrrolo[3,4-d]pyrimidin-6-yl]-6-oxo-hexanenitrile (0.077 g; 1.0 equiv; 0.213 mmoles) in toluene (6 mL). Heat the resulting solution to 105° C. for 16 hours. Cool the reaction mixture to ambient temperature and concentrate. Dissolve the residue in methanol (5 mL) and load the solution on an SCX column (eluting with methanol to 7N ammonia in methanol) to afford the crude product, which is purified by reverse phase chromatography to give 1-[2-(2,3-dihydro-1H-inden-2-ylamino)-5,7-dihydro-6H-pyrrolo[3,4-d]pyrimidin-6-yl]-5-(1H-tetrazol-5-yl)pentan-1-one (0.0265 g; 31%): MS (m/z): 405(M+1).

Scheme P

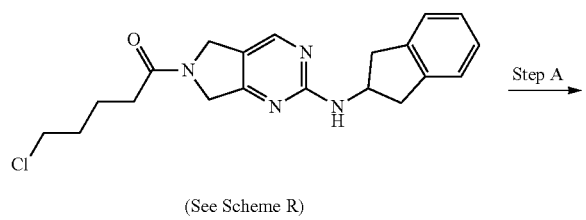

(See Scheme R)

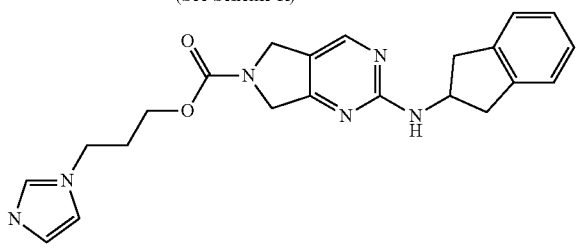

Example 13

Synthesis of 3-(1H-imidazol-1-yl)propyl 2-(2,3-dihydro-1H-inden-2-ylamino)-5,7-dihydro-6H-pyrrolo[3,4-d]pyrimidine-6-carboxylate

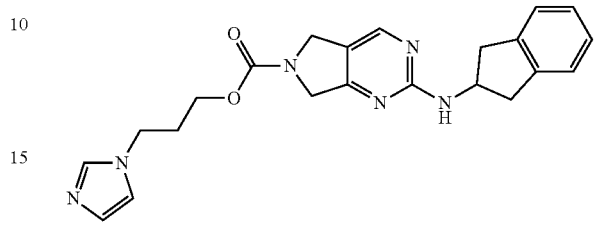

Scheme P, Step A.

Add sodium hydride (0.068 g; 2.25 equiv; 1.70 mmoles) to a solution of: 3-chloropropyl 2-(indan-2-ylamino)-5,7-dihydropyrrolo[3,4-d]pyrimidine-6-carboxylate (0.283 g; 1.0 equiv; 0.76 mmoles), and 1H-imidazole (0.105 g; 2.0 equiv; 1.54 mmoles) in dimethylformamide (2.4 mL). Stir the reaction mixture for 16 hours, then dilute with dichloromethane and wash with water. Extract the aqueous layer with dichloromethane twice. Concentrate the combined organic extracts and then purify the crude product by column chromatography (0 to 10% methanol in dichloromethane) to afford of 3-(1H-imidazol-1-yl)propyl 2-(2,3-dihydro-1H-inden-2-ylamino)-5,7-dihydro-6H-pyrrolo[3,4-d]pyrimidine-6-carboxylate (0.0922 g; 30%) as a yellow solid: MS (m/z): 405(M+1).

Scheme Q

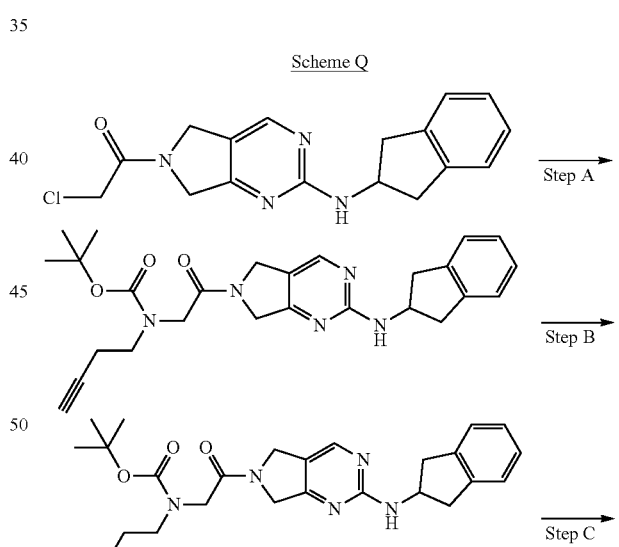

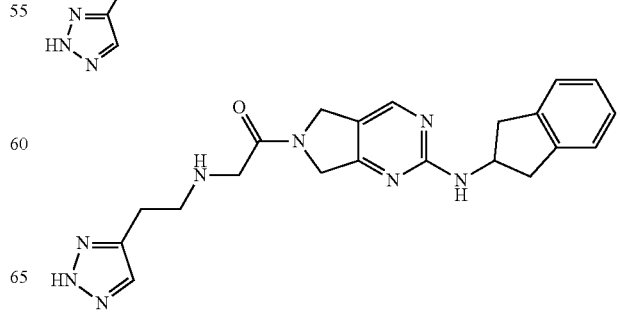

Preparation 33

Synthesis of tert-butyl N-but-3-ynyl-N-[2-[2-(indan-2-ylamino)-5,7-dihydropyrrolo[3,4-d]pyrimidin-6-yl]-2-oxo-ethyl]carbamate

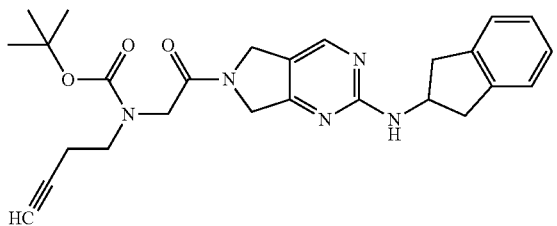 [SMILES: C#CCCN(CC(=O)N1Cc2cnc(NC3Cc4ccccc4C3)nc2C1)C(=O)OC(C)(C)C]

Scheme Q, Step A.

Add but-3-yn-1-amine (1.24 g; 8 equiv; 4.48 mmoles) quickly to a flask containing 2-chloro-1-[2-(2,3-dihydro-1H-inden-2-ylamino)-5,7-dihydro-6H-pyrrolo[3,4-d]pyrimidin-6-yl]ethanone (0.184 g; 1.0 equiv; 0.56 mmoles) and triethylamine (0.094 mL; 1.2 equiv; 0.67 mmoles) in tetrahydrofuran (5 mL). Stir at ambient temperature for 15 minutes, then heat to 55° C. for 1 hour and to 65° C. for 30 minutes. Concentrate the mixture and then dissolve the residue in dichloromethane (10 mL). Add di-t-butyldicarbonate (0.8 g; 6.5 equiv; 3.67 mmoles) and stir at room temperature for 30 minutes. Load the solution directly onto a silica gel column and purify via chromatography (0 to 100% ethyl acetate/hexanes) to give tert-butyl N-but-3-ynyl-N-[2-[2-(indan-2-ylamino)-5,7-dihydropyrrolo[3,4-d]pyrimidin-6-yl]-2-oxo-ethyl]carbamate (0.204 g; 79%) as a colorless foam: MS (m/z): 462(M+1).

Preparation 34

Synthesis of tert-butyl {2-[2-(2,3-dihydro-1H-inden-2-ylamino)-5,7-dihydro-6H-pyrrolo[3,4-d]pyrimidin-6-yl]-2-oxoethyl}[2-(1H-1,2,3-triazol-5-yl)ethyl]carbamate

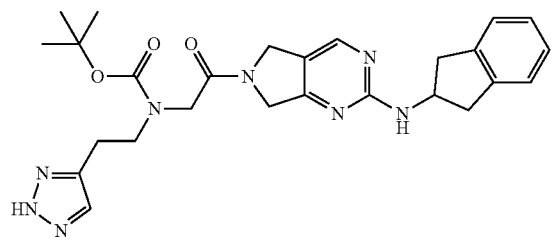 [SMILES: CC(C)(C)OC(=O)N(CCc1cn[nH]n1)CC(=O)N1Cc2cnc(NC3Cc4ccccc4C3)nc2C1]

Scheme Q, Step B.

Add copper(II)sulfate pentahydrate (0.022 g; 0.2 equiv; 0.088 mmoles) and L-ascorbic acid sodium salt (0.175 g; 2.0 equiv; 0.88 mmoles) to a deoxygenated solution of tert-butyl N-but-3-ynyl-N-[2-[2-(indan-2-ylamino)-5,7-dihydropyrrolo[3,4-d]pyrimidin-6-yl]-2-oxo-ethyl]carbamate (0.204 g; 1.0 equiv; 0.44 mmoles) in dimethylformamide (6 mL) and water (3 mL) (including toluene (0.05 mL) as an internal standard). Heat to 90° C. and then add azidotrimethylsilane (0.47 mL; 8 equiv; 3.54 mmoles) dropwise with continued stirring at 90° C. Stir for 3 hours, then dilute the reaction mixture with water (100 mL) and ethyl acetate (50 mL). Extract with ethyl acetate (3×50 mL), and wash the combined organic extracts with brine. Dry the organics over magnesium sulfate, filter, and concentrate. Purify the crude product by column chromatography (0 to 10% methanol in ethyl acetate) to give tert-butyl {2-[2-(2,3-dihydro-1H-inden-2-ylamino)-5,7-dihydro-6H-pyrrolo[3,4-d]pyrimidin-6-yl]-2-oxoethyl}[2-(1H-1,2,3-triazol-5-yl)ethyl]carbamate (0.157 g; 70%) as a yellowish foam: MS (m/z): 505(M+1).

Example 14

Synthesis of 1-[2-(2,3-dihydro-1H-inden-2-ylamino)-5,7-dihydro-6H-pyrrolo[3,4-d]pyrimidin-6-yl]-2-{[2-(1H-1,2,3-triazol-5-yl)-ethyl]amino}ethanone

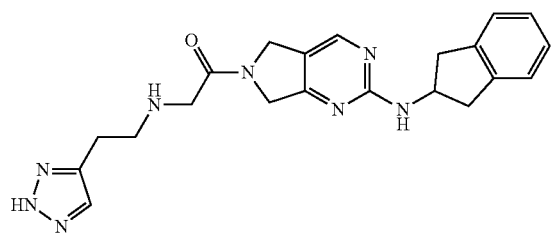

Scheme Q, Step C.

Add trifluoroacetic acid (3 mL) slowly to a 0° C. solution containing tert-butyl {2-[2-(2,3-dihydro-1H-inden-2-ylamino)-5,7-dihydro-6H-pyrrolo[3,4-d]pyrimidin-6-yl]-2-oxoethyl}[2-(1H-1,2,3-triazol-5-yl)ethyl]carbamate (0.15 g; 1.0 equiv; 0.297 mmoles) in dichloromethane (1 mL). Stir for 2 hours, then warm to ambient temperature and stir for 30 minutes. Concentrate the mixture and dissolve the residue in dichloromethane (20 mL). Add saturated sodium bicarbonate (20 mL), brine (20 mL), and water (50 mL), and extract with dichloromethane (6×20 mL). Dry the combined organic extracts over magnesium sulfate, filter, and concentrate to afford 1-[2-(2,3-dihydro-1H-inden-2-ylamino)-5,7-dihydro-6H-pyrrolo[3,4-d]pyrimidin-6-yl]-2-{[2-(1H-1,2,3-triazol-5-yl)-ethyl]amino}ethanone (0.093 g; 77%) as a yellowish foam: MS (m/z): 405(M+1).

Scheme R

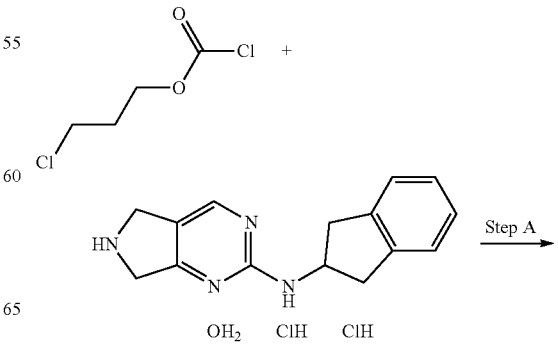

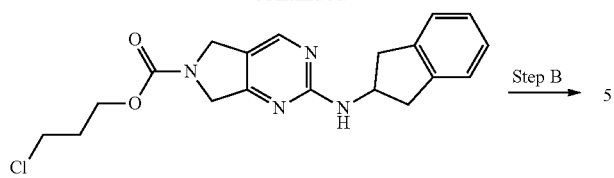

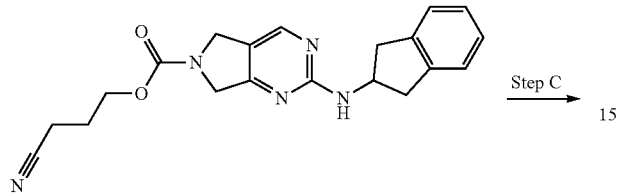

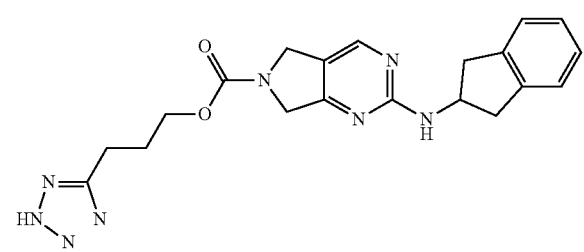

Preparation 35

Synthesis of 3-chloropropyl 2-(indan-2-yl amino)-5,7-dihydropyrrolo[3,4-d]pyrimidine-6-carboxylate

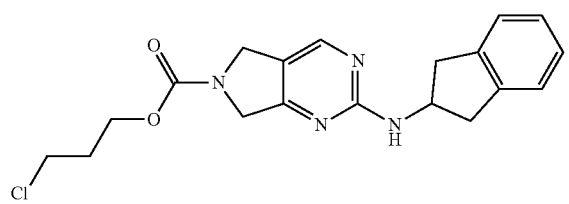 [SMILES: O=C(OCCCCl)N1Cc2cnc(NC3Cc4ccccc4C3)nc2C1]

Scheme R, Step A.

Add a solution of 3-chloropropyl carbonochloridate (0.55 mL; 1.48 equiv; 4.54 mmoles) in tetrahydrofuran (21 mL) dropwise over 1 hour to a mixture of N-(2,3-dihydro-1H-inden-2-yl)-6,7-dihydro-5H-pyrrolo[3,4-d]pyrimidin-2-amine dihydrochloride hydrate (1.0 g; 1.0 equiv; 3.07 mmoles) and triethylamine (2.2 mL; 5.1 equiv; 15.78 mmoles) in tetrahydrofuran (21 mL). Stir the solution for 18 hours, then dilute with dichloromethane and wash with sodium bicarbonate solution. Further extract the aqueous layer with dichloromethane (2×). Dry the combined organic extracts over sodium sulfate, filter, and concentrate to afford 3-chloropropyl 2-(indan-2-ylamino)-5,7-dihydropyrrolo[3,4-d]pyrimidine-6-carboxylate (1.15 g; 100%) as a brown solid: MS (m/z): 373(M+1).

Preparation 36

Synthesis of 3-cyanopropyl 2-(indan-2-ylamino)-5,7-dihydropyrrolo[3,4-d]pyrimidine-6-carboxylate

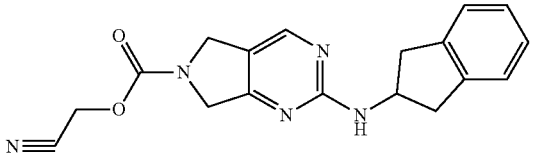 [SMILES: N#CCOC(=O)N1Cc2cnc(NC3Cc4ccccc4C3)nc2C1]

Scheme R, Step B.

Add sodium cyanide (0.230 g; 1.5 equiv; 4.69 mmoles) to a solution containing 3-chloropropyl 2-(indan-2-ylamino)-5,7-dihydropyrrolo[3,4-d]pyrimidine-6-carboxylate (1.15 g; 1.0 equiv; 3.08 mmoles) in dimethylformamide (10 mL). Heat the reaction mixture to 100° C. for 3 hours, then cool to ambient temperature, dilute with dichloromethane, water, and 5% lithium chloride solution. Separate the layers and further extract the aqueous layer with dichloromethane and ethyl acetate. Dry the combined organic extracts over sodium sulfate, filter, and concentrate to provide 3-cyanopropyl 2-(indan-2-ylamino)-5,7-dihydropyrrolo[3,4-d]pyrimidine-6-carboxylate (0.98 g; 87%) as a brown solid: MS (m/z): 364(M+1).

Example 15

Synthesis of 3-(1H-tetrazol-5-yl)propyl 2-(2,3-dihydro-1H-inden-2-ylamino)-5,7-dihydro-6H-pyrrolo[3,4-d]pyrimidine-6-carboxylate

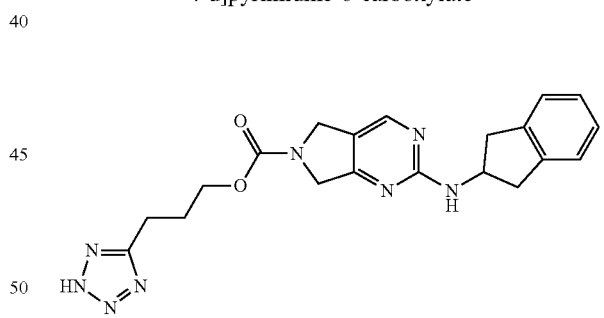

Scheme R, Step C.

Add azidotrimethylsilane (3.5 mL; 9.7 equiv; 26.27 mmoles) and dibutyloxostannane (0.163 g; 0.25 equiv; 0.66 mmoles) to a solution of 3-cyanopropyl 2-(indan-2-ylamino)-5,7-dihydropyrrolo[3,4-d]pyrimidine-6-carboxylate (0.98 g; 1.0 equiv; 2.70 mmoles) in toluene (20.4 mL). Heat the reaction mixture to 100° C. for 18 hours. Concentrate the solution and purify by reverse phase chromatography followed by silica gel chromatography (0 to 15% methanol in chloroform) to afford the desired 3-(1H-tetrazol-5-yl)propyl 2-(2,3-dihydro-1H-inden-2-ylamino)-5,7-dihydro-6H-pyrrolo[3,4-d]pyrimidine-6-carboxylate (0.097 g; 9%) as a brown solid: MS (m/z): 407(M+1).

45

Scheme S

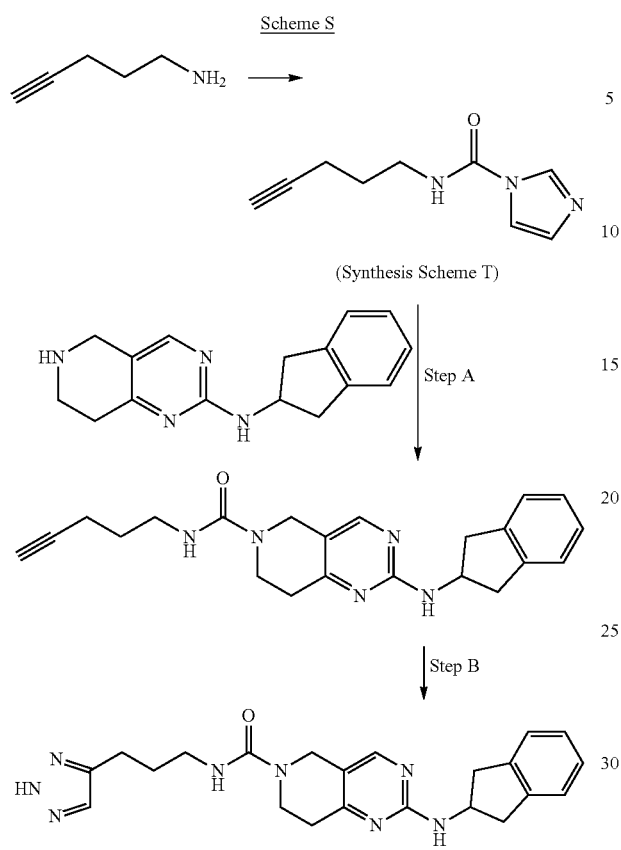

Preparation 37

Synthesis of 2-(2,3-dihydro-1H-inden-2-ylamino)-n-(pent-4-yn-1-yl)-7,8-dihydropyrido[4,3-d]pyrimidine-6(5H)-carboxamide Scheme S, Step A.

Add N-indan-2-yl-5,6,7,8-tetrahydropyrido[4,3-d]pyrimidin-2-amine (0.418 g; 1.05 equiv; 1.57 mmoles) followed by 4-pyridinamine, N,N-dimethyl-(0.185 g; 1.0 equiv; 1.50 mmoles) and triethylamine (0.42 mL; 2.0 equiv; 2.99 mmoles) to a −78° C. solution of N-pent-4-ynylimidazole-1-carboxamide (0.265 g; 1.0 equiv; 1.50 mmoles). Warm the resulting pale yellow solution to room temperature and stir for 18 hours. Load the reaction mixture directly onto a silica pre-column and purify by column chromatography (10 to 50% acetone in hexanes) to afford 2-(2,3-dihydro-1H-inden-2-ylamino)-n-(pent-4-yn-1-yl)-7,8-dihydropyrido[4,3-d]pyrimidine-6(5H)-carboxamide (0.286 g; 51%) as a white solid: MS (m/z): 376(M+1).

46

Example 16

Synthesis of 2-(2,3-dihydro-1H-inden-2-ylamino)-n-[3-(1H-1,2,3-triazol-4-yl)propyl]-7,8-dihydropyrido[4,3-d]pyrimidine-6(5H)-carboxamide

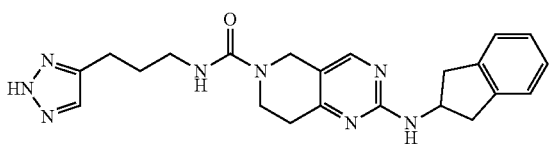 [SMILES: O=C(NCCCc1cn[nH]n1)N1CCc2nc(NC3Cc4ccccc4C3)ncc2C1]

Scheme S, Step B.

Add copper(II)sulfate pentahydrate (0.037 g; 0.2 equiv; 0.15 mmoles) and L-ascorbic acid sodium salt (0.29 g; 2.0 equiv; 1.46 mmoles) to a deoxygenated solution containing 2-(2,3-dihydro-1H-inden-2-ylamino)-n-(pent-4-yn-1-yl)-7,8-dihydropyrido[4,3-d]pyrimidine-6(5H)-carboxamide (0.275 g; 1.0 equiv; 0.73 mmoles) in dimethylformamide (2.44 mL) and water (2.44 mL). Add azidotrimethylsilane (0.78 mL; 8 equiv; 5.86 mmoles) and heat to 90° C. for 1 hour. Cool the solution to ambient temperature, dilute the reaction mixture with 30 mL water, and extract with ethyl acetate (3×50 mL). Wash the combined organic extracts with water and brine, dry over sodium sulfate, filter and concentrate in vacuo to a yellow oil. Purify the crude product by column chromatography (0 to 80% acetone in dichloromethane) to afford 2-(2,3-dihydro-1H-inden-2-ylamino)-N-[3-(1H-1,2,3-triazol-4-yl)propyl]-7,8-dihydropyrido[4,3-d]pyrimidine-6(5H)-carboxamide (0.132 g; 43%) as a white solid: MS (m/z): 419(M+1).

Scheme T

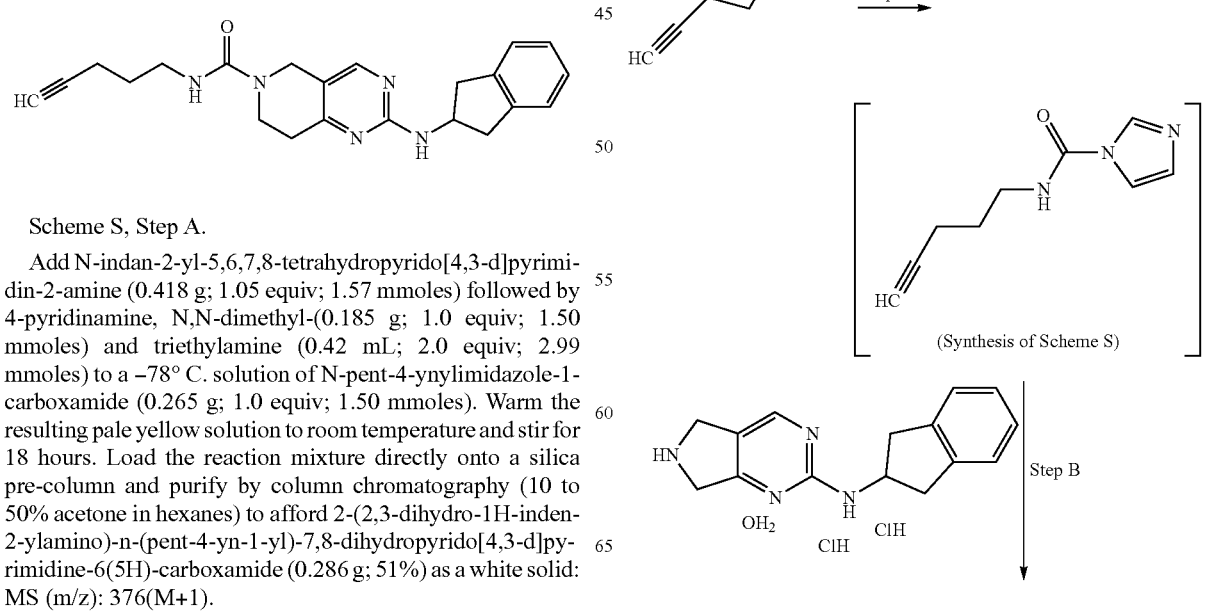

-continued

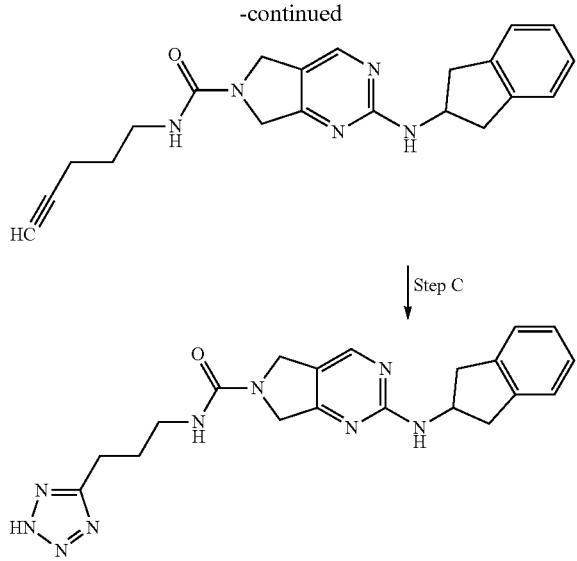

Preparation 38

Synthesis of N-pent-4-ynylimidazole-1-carboxamide

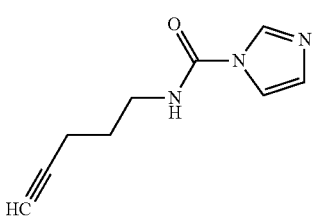

Scheme T, Step A.

Add 1,1'-carbonyldiimidazole (0.539 mg 1.05 equiv; 3.26 mmoles) slowly portion wise to a −78° C. solution of 4-pentyn-1-amine (0.258 mL; 1.0 equiv; 3.10 mmoles) in dichloromethane (10 mL). Allow the reaction to warm to ambient temperature and stir for 72 hours. Use the solution directly for subsequent chemistry: MS (m/z): 178(M+1).

Preparation 39

Synthesis of 2-(2,3-dihydro-1H-inden-2-ylamino)-n-(pent-4-yn-1-yl)-5,7-dihydro-6H-pyrrolo[3,4-d]pyrimidine-6-carboxamide

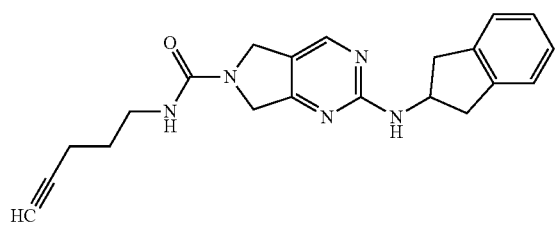 [SMILES: C#CCCCNC(=O)N1Cc2cnc(NC3Cc4ccccc4C3)nc2C1]

Scheme T, Step B.

Add N-(2,3-dihydro-1H-inden-2-yl)-6,7-dihydro-5H-pyrrolo[3,4-d]pyrimidin-2-amine dihydrochloride hydrate (0.266 g; 0.5 equiv; 0.78 mmoles) followed by triethylamine (1.08 mL; 5 equiv; 7.76 mmoles) and 4-pyridinamine, N,N-dimethyl-(0.029 g; 0.15 equiv; 0.23 mmoles) to a −78° C. solution of N-pent-4-ynylimidazole-1-carboxamide (0.275 g; 1.0 equiv; 1.55 mmoles) in dichloromethane (5 mL). Allow the light brown solution to warm to ambient temperature and stir for 24 hours. Load the reaction mixture directly onto a silica gel column and purify by column chromatography (0 to 30% ethyl acetate in hexanes) to afford 2-(2,3-dihydro-1H-inden-2-ylamino)-n-(pent-4-yn-1-yl)-5,7-dihydro-6H-pyrrolo[3,4-d]pyrimidine-6-carboxamide (0.293 g; 63%) as a white solid: MS (m/z): 362(M+1).

Example 17

Synthesis of 2-(2,3-dihydro-1H-inden-2-ylamino)-N-[3-(1H-1,2,3-triazol-4-yl)propyl]-5,7-dihydro-6H-pyrrolo[3,4-d]pyrimidine-6-carboxamide

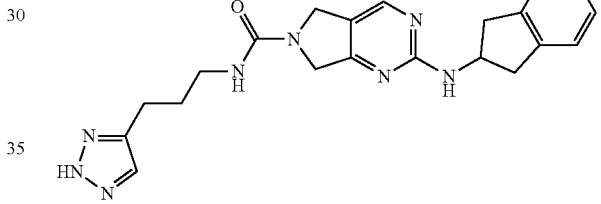

Scheme T, Step C.

Add copper(II)sulfate pentahydrate (0.049 g; 0.2 equiv; 0.20 mmoles) and L-ascorbic acid sodium salt (0.388 g; 2.0 equiv; 1.96 mmoles) to a deoxygenated solution of 2-(2,3-dihydro-1H-inden-2-ylamino)-N-(pent-4-yn-1-yl)-5,7-dihydro-6H-pyrrolo[3,4-d]pyrimidine-6-carboxamide (0.354 g; 1.0 equiv; 0.98 mmoles) in dimethylformamide (3.26 mL) and water (3.26 mL). Add azidotrimethylsilane (1.04 mL; 8 equiv; 7.84 mmoles) and heat the mixture to 90° C. for 1 hour, the cool to ambient temperature and stir for 16 hours. Concentrate the solution to dryness, and purify the resulting orange semisolid by column chromatography (0 to 10% methanol in ethyl acetate) to afford 2-(2,3-dihydro-1H-inden-2-ylamino)-N-[3-(1H-1,2,3-triazol-4-yl)propyl]-5,7-dihydro-6H-pyrrolo[3,4-d]pyrimidine-6-carboxamide (0.085 g; 21%) as a solid: MS (m/z): 405(M+1).

Scheme U

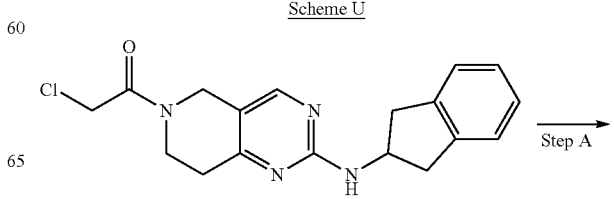

Step A

-continued

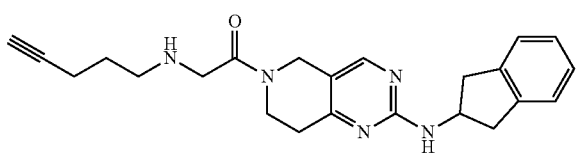

Step B

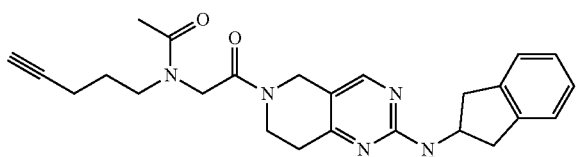

Step C

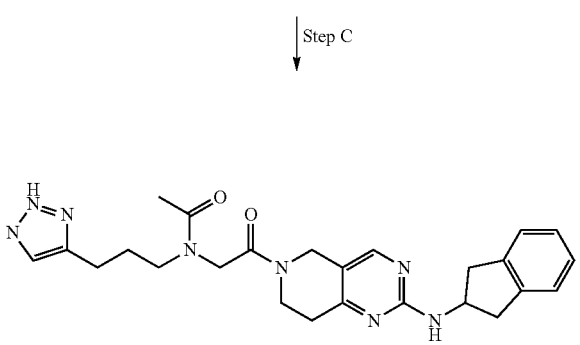

Preparation 40

Synthesis of 1-[2-(indan-2-ylamino)-7,8-dihydro-5H-pyrido[4,3-d]pyrimidin-6-yl]-2-(pent-4-ynylamino)ethanone

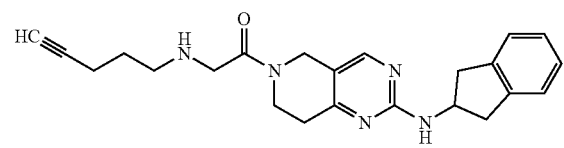 [SMILES: C#CCCCNCC(=O)N1CCc2nc(NC3Cc4ccccc4C3)ncc2C1]

Scheme U, Step A.

Add triethylamine (0.434 mL; 2.0 equiv; 3.12 mmoles) followed by 4-pentyn-1-amine (0.194 mL; 1.50 equiv; 2.34 mmoles) to a solution of 2-chloro-1-[2-(2,3-dihydro-1H-inden-2-ylamino)-7,8-dihydropyrido[4,3-d]pyrimidin-6(5H)-yl]ethanone (0.534 g; 1.0 equiv; 1.56 mmoles) in tetrahydrofuran (5.19 mL). Stir for 48 hours at 55° C. The solution was directly concentrated to afford 1-[2-(indan-2-ylamino)-7,8-dihydro-5H-pyrido[4,3-d]pyrimidin-6-yl]-2-(pent-4-ynylamino)ethanone (0.606 g; 100%): MS (m/z): 390(M+1).

Preparation 41

Synthesis of N-{2-[2-(2,3-dihydro-1H-inden-2-ylamino)-7,8-dihydropyrido[4,3-d]pyrimidin-6(5H)-yl]-2-oxoethyl}-n-(pent-4-yn-1-yl)acetamide

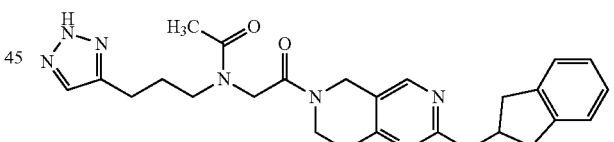

Scheme U, Step B.

Add acetic acid anhydride (0.176 mL; 1.20 equiv; 1.87 mmoles) followed by triethylamine (0.325 mL 1.5 equiv; 2.33 mmoles) to a solution of 1-[2-(indan-2-ylamino)-7,8-dihydro-5H-pyrido[4,3-d]pyrimidin-6-yl]-2-(pent-4-ynylamino)ethanone (0.606 g; 1.0 equiv; 1.56 mmoles) in dichloromethane (5.2 mL). Dilute the reaction mixture with water and dichloromethane. Separate the layers and wash the organic extract with brine, dry over sodium sulfate, filter, and concentrate to an orange/brown oil. Purify the crude product by column chromatography (0 to 2% methanol in ethyl acetate) to afford the desired N-{2-[2-(2,3-dihydro-1H-inden-2-ylamino)-7,8-dihydropyrido[4,3-d]pyrimidin-6(5H)-yl]-2-oxoethyl}-n-(pent-4-yn-1-yl)acetamide (0.138 g; 21%): MS (m/z): 432(M+1).

Example 18

Synthesis of N-{2-[2-(2,3-dihydro-1H-inden-2-ylamino)-7,8-dihydropyrido[4,3-d]pyrimidin-6(5H)-yl]-2-oxoethyl}-N-[3-(1H-1,2,3-triazol-4-yl)propyl]acetamide Scheme U, Step C.

Add copper(II)sulfate pentahydrate (0.016 g; 0.2 equiv; 0.063 mmoles) and L-ascorbic acid sodium salt (0.126 g; 2.0 equiv; 0.64 mmoles) to a deoxygenated solution containing N-{2-[2-(2,3-dihydro-1H-inden-2-ylamino)-7,8-dihydropyrido[4,3-d]pyrimidin-6(5H)-yl]-2-oxoethyl}-n-(pent-4-yn-1-yl)acetamide (0.137 g; 1.0 equiv; 0.32 mmoles) in dimethylformamide (2.12 mL) and water (1.06 mL). Add azidotrimethylsilane (0.34 mL; 8 equiv; 2.54 mmoles) and heat the resulting solution to 90° C. for 1 hour. Concentrate the reaction mixture to a brown paste and purify the crude product by column chromatography (0 to 10% methanol in ethyl acetate) to afford N-{2-[2-(2,3-dihydro-1H-inden-2-ylamino)-7,8-dihydropyrido[4,3-d]pyrimidin-6(5H)-yl]-2-oxoethyl}-N-[3-(1H-1,2,3-triazol-4-yl)propyl]acetamide (0.036 g; 25%) as an off-white solid: MS (m/z): 475(M+1).

Scheme V

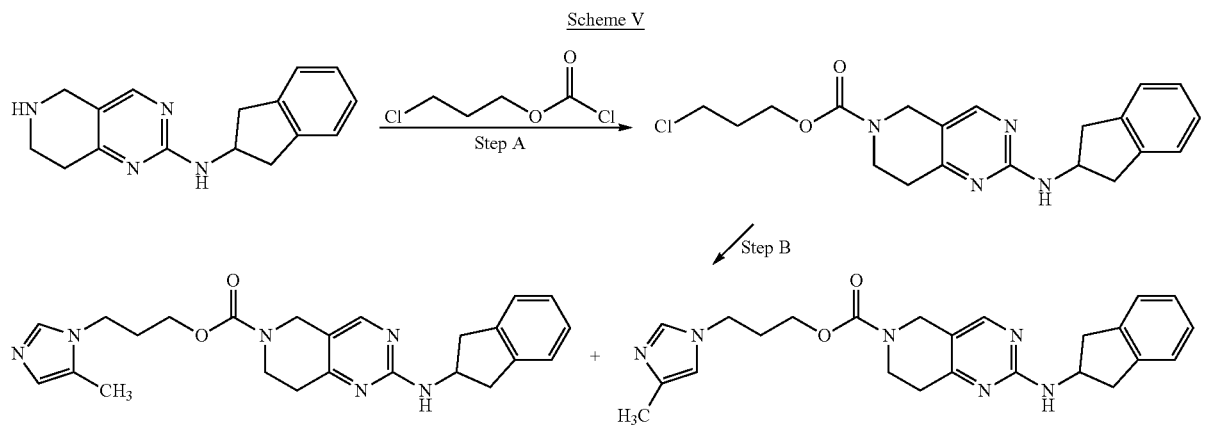

Preparation 42

Synthesis of 3-chloropropyl 2-(indan-2-ylamino)-7,8-dihydro-5H-pyrido[4,3-d]pyrimidine-6-carboxylate

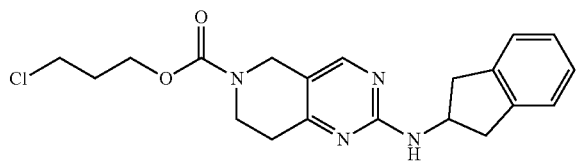 [SMILES: O=C(OCCCCl)N1CCc2nc(NC3Cc4ccccc4C3)ncc2C1]

Scheme V, Step A.

Add a solution of 3-chloropropyl carbonochloridate (0.55 mL; 1.2 equiv; 4.51 mmoles) in tetrahydrofuran (25 mL) over 1 hour to a mixture of N-indan-2-yl-5,6,7,8-tetrahydropyrido[4,3-d]pyrimidin-2-amine (1.00 g; 1.0 equiv; 3.75 mmoles) and triethylamine (1.10 mL; 2.1 equiv; 7.88 mmoles) in tetrahydrofuran (25 mL). Stir for 2 hours, then dilute with dichloromethane and saturated sodium bicarbonate and separate the layers. Further extract the aqueous layer with dichloromethane (2×). Dry the combined organic extracts over sodium sulfate, filter, and concentrated to dryness to give a yellow oil. Purify the crude product by column chromatography (10% methanol in dichloromethane) to 3-chloropropyl 2-(indan-2-ylamino)-7,8-dihydro-5H-pyrido[4,3-d]pyrimidine-6-carboxylate (1.146 g; 79%): MS (m/z): 387(M+1).

Example 19

Synthesis of 3-(5-methyl-1H-imidazol-1-yl)propyl 2-(2,3-dihydro-1H-inden-2-ylamino)-7,8-dihydropyrido[4,3-d]pyrimidine-6(5H)-carboxylate

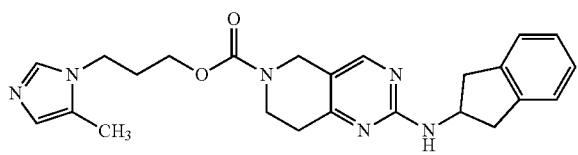 [SMILES: Cc1cncn1CCCOC(=O)N1CCc2nc(NC3Cc4ccccc4C3)ncc2C1]

Scheme V, Step B.

Add sodium hydride (0.121 g; 2.2 equiv; 3.01 mmoles) to a solution of 4(5)-methylimidazole (0.180 g; 1.6 equiv; 2.19 mmoles) in tetrahydrofuran (15 mL). Cool the reaction mixture to 0° C. and stir for 15 minutes before adding 3-chloropropyl 2-(indan-2-ylamino)-7,8-dihydro-5H-pyrido[4,3-d]pyrimidine-6-carboxylate (0.530 g; 1.0 equiv; 1.37 mmoles). Allow the reaction to stir at ambient temperature for 24 hours. Dilute the reaction mixture with dichloromethane and water and separate the layers. Further extract the aqueous layer with dichloromethane (2×). Dry the combined organic extracts over sodium sulfate, filter, and concentrate to dryness to give a yellow liquid. Purify the crude products by column chromatography (0 to 5% methanol in dichloromethane) to afford a mixture of both regioisomeric products. Further purification using a chiral chromatographic support (chiralcel OJ-H, 5% acetonitrile in methanol with 0.2% isopropylamine) affords product 3-(5-methyl-1H-imidazol-1-yl)propyl 2-(2,3-dihydro-1H-inden-2-ylamino)-7,8-dihydropyrido[4,3-d]pyrimidine-6(5H)-carboxylate (0.055 g; 12%). MS (m/z): 433(M+1).

Example 20

Synthesis of 3-(4-methyl-1H-imidazol-1-yl)propyl 2-(2,3-dihydro-1H-inden-2-ylamino)-7,8-dihydropyrido[4,3-d]pyrimidine-6(5H)-carboxylate

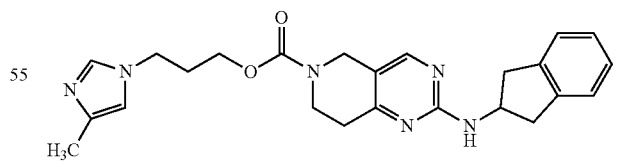

Prepare substantially as described in Example 19. Further purification using a chiral chromatographic support (chiralcel OJ-H, 5% acetonitrile in methanol with 0.2% isopropylamine) affords product 3-(4-methyl-1H-imidazol-1-yl)propyl 2-(2,3-dihydro-1H-inden-2-ylamino)-7,8-dihydropyrido[4,3-d]pyrimidine-6(5H)-carboxylate (0.111 g; 25%). MS (m/z): 433(M+1).

Scheme W

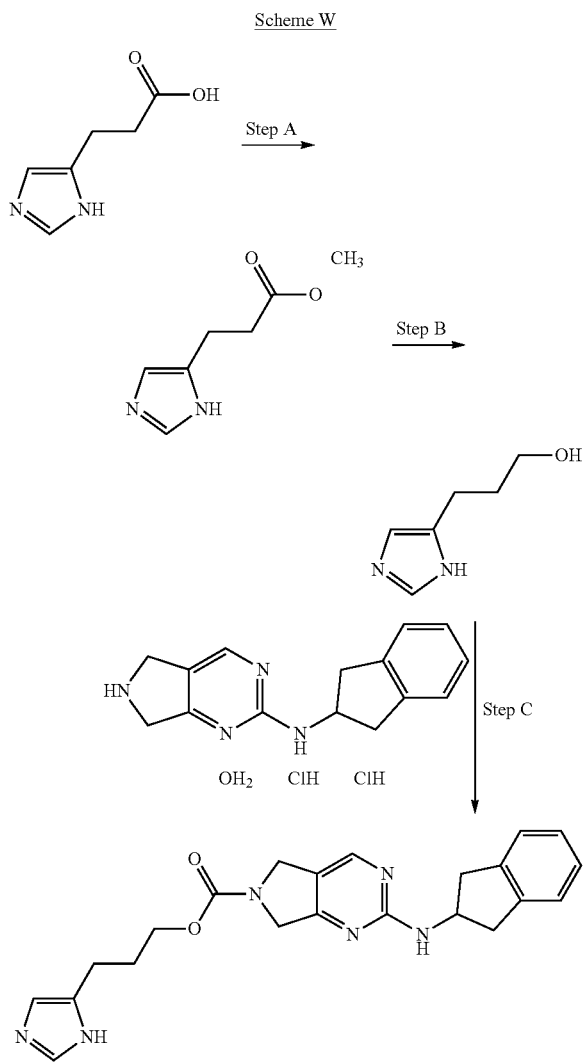

Preparation 43

Synthesis of methyl 3-(1H-imidazol-5-yl)propanoate

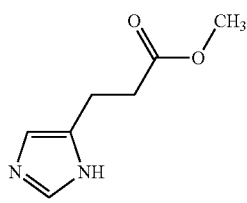

Scheme W, Step A.

Add thionyl chloride (0.75 mL) to a −78° C. solution of 3-(1H-imidazol-5-yl)propanoic acid (2.0 g; 1.0 equiv; 14.27 mmoles) in methanol (18 mL). Allow the reaction mixture to warm to ambient temperature and stir for 30 minutes. Add saturated sodium bicarbonate (10 mL) to the reaction mixture and concentrate. Suspended the resulting residue in methanol (10 mL) and filter, then concentrate to afford methyl 3-(1H-imidazol-5-yl)propanoate (2.2 g; 100%) as a white solid: MS (m/z): 155(M+1).

Preparation 44

Synthesis of 3-(1H-imidazol-5-yl)propan-1-ol

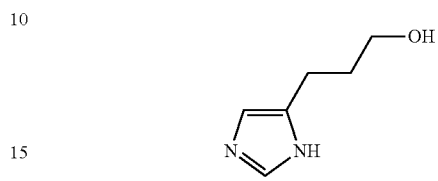

Scheme W, Step B.

Add lithium aluminum hydride (1M in tetrahydrofuran; 17 mL; 2.0 equiv; 17.00 mmoles) dropwise over 5 minutes to a 0° C. solution of methyl 3-(1H-imidazol-4-yl)propanoate (2.2 g; 1.0 equiv; 8.52 mmoles) in tetrahydrofuran (85 mL). Warm the reaction mixture to ambient temperature and stir for 16 hours. Add water (0.65 mL), 15% sodium hydroxide (0.65 mL), and water (1.95 mL) sequentially, then stir for 30 minutes. Filter the resulting solid and rinse with acetone. Concentrate the filtrate to afford 3-(1H-imidazol-5-yl)propan-1-ol (3.0 g; 61%) as a white solid. To further purify the product, suspend a portion of 3-(1H-imidazol-4-yl)propan-1-ol (1.5 g) in water (50 mL) and stir at 100° C. for 2 hours. Filter the product mixture and concentrate the filtrate to afford pure 3-(1H-imidazol-5-yl)propan-1-ol (0.5 g) as an off white solid: MS (m/z): 127(M+1).

Example 21

Synthesis of 3-(1H-imidazol-5-yl)propyl 2-(2,3-dihydro-1H-inden-2-ylamino)-5,7-dihydro-6H-pyrrolo[3,4-d]pyrimidine-6-carboxylate

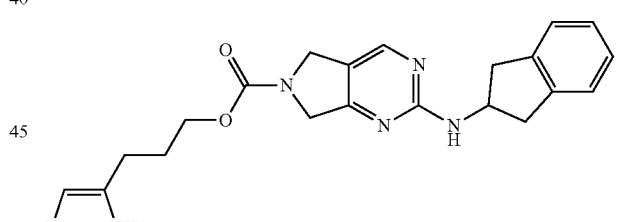

Scheme W, Step C.

Add 1,1'-carbonyldiimidazole (0.51 g; 1.2 equiv; 3.15 mmoles) to a solution of 3-(1H-imidazol-5-yl)propan-1-ol (0.50 g; 1.0 equiv; 2.62 mmoles) in dimethylformamide (8.5 mL) and stir for 1 hour. Slowly add N-(2,3-dihydro-1H-inden-2-yl)-6,7-dihydro-5H-pyrrolo[3,4-d]pyrimidin-2-amine dihydrochloride hydrate (0.94 g; 1.10 equiv; 2.89 mmoles) to the aforementioned solution. Stir for 16 hours at ambient temperature and then heat to 60° C. for an additional 16 hours. Partition the reaction mixture between water and chloroform and separate the layers. Further extract the aqueous layer with chloroform (2×). Dry the combined organic extracts over magnesium sulfate, filter, and concentrate to a viscous liquid. Purify the crude product by column chromatography (0 to 20% methanol in dichloromethane) to afford 3-(1H-imidazol-5-yl)propyl 2-(2,3-dihydro-1H-inden-2-ylamino)-5,7-dihydro-6H-pyrrolo[3,4-d]pyrimidine-6-carboxylate (0.041 g; 4%) as a brown solid: MS (m/z): 405(M+1).

Scheme X

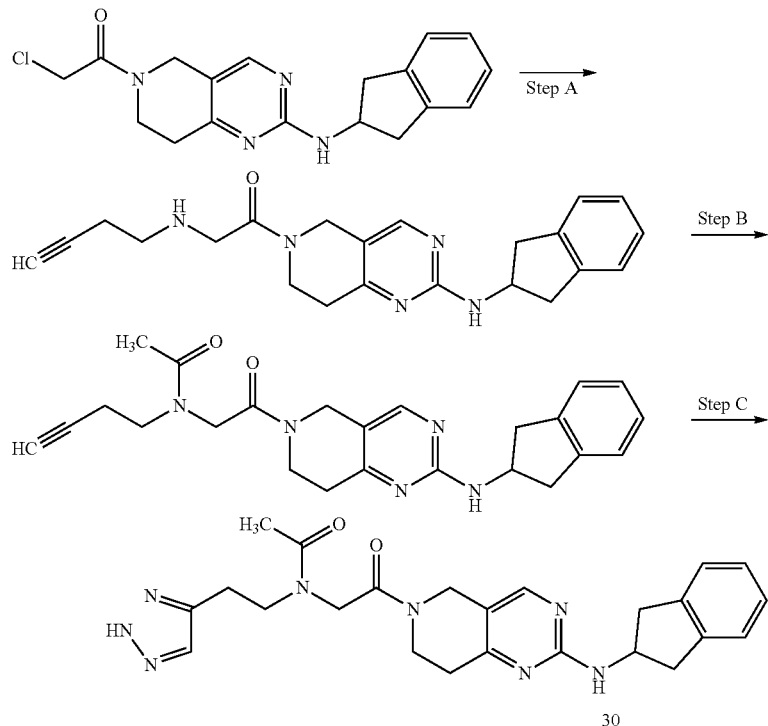

Preparation 45

Synthesis of 2-(but-3-ynylamino)-1-[2-(indan-2-ylamino)-7,8-dihydro-5H-pyrido[4,3-d]pyrimidin-6-yl]ethanone

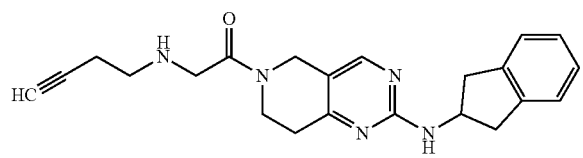 [SMILES: C#CCCNCC(=O)N1CCc2nc(NC3Cc4ccccc4C3)ncc2C1]

Scheme X, Step A.

Add triethylamine (0.85 mL; 2.0 equiv; 6.13 mmoles) followed by 1-amino-3-butyne (0.38 mL; 1.5 equiv; 4.59 mmoles) to a solution of 2-chloro-1-[2-(2,3-dihydro-1H-inden-2-ylamino)-7,8-dihydropyrido[4,3-d]pyrimidin-6(5H)-yl]ethanone (1.05 g; 1.0 equiv; 3.06 mmoles) in tetrahydrofuran (10.2 mL), and heat to 55° C. for 16 hours, then concentrate and use the 2-(but-3-ynylamino)-1-[2-(indan-2-ylamino)-7,8-dihydro-5H-pyrido[4,3-d]pyrimidin-6-yl]ethanone directly in the next step: MS (m/z): 376(M+1).

Preparation 46

Synthesis of N-(but-3-yn-1-yl)-n-{2-[2-(2,3-dihydro-1H-inden-2-ylamino)-7,8-dihydropyrido[4,3-d]pyrimidin-6(5H)-yl]-2-oxoethyl}acetamide

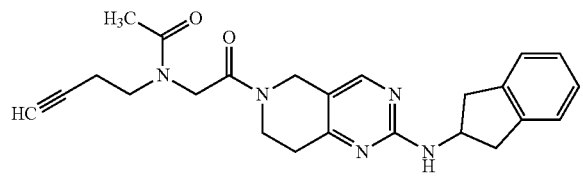 [SMILES: C#CCCN(CC(=O)N1CCc2nc(NC3Cc4ccccc4C3)ncc2C1)C(C)=O]

Scheme X, Step B.

Add acetyl chloride (0.041 mL; 1.2 equiv; 0.58 mmoles) and triethylamine (0.101 mL; 1.5 equiv; 0.73 mmoles) to a solution of 2-(but-3-ynylamino)-1-[2-(indan-2-ylamino)-7,8-dihydro-5H-pyrido[4,3-d]pyrimidin-6-yl]ethanone (0.303 g; 1.0 equiv; 0.48 mmoles) in dichloromethane (1.61 mL). After 5 minutes, dilute the reaction with water and dichloromethane (20 mL each) and separate the layers. Wash the organic layer with brine, dry over sodium sulfate, filter, and concentrate to an orange/brown oil. Purify the crude product by column chromatography (0 to 80% acetone in dichloromethane) to afford N-(but-3-yn-1-yl)-n-{2-[2-(2,3-dihydro-1H-inden-2-ylamino)-7,8-dihydropyrido[4,3-d]pyrimidin-6(5H)-yl]-2-oxoethyl}acetamide (0.08 g; 38%): MS (m/z): 418(M+1).

Example 22

Synthesis of N-{2-[2-(2,3-dihydro-1H-inden-2-ylamino)-7,8-dihydropyrido[4,3-d]pyrimidin-6(5H)-yl]-2-oxoethyl}-n-[2-(1H-1,2,3-triazol-4-yl)ethyl]acetamide

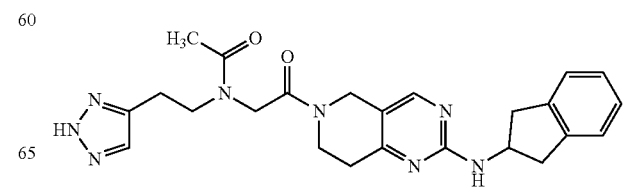

Scheme X, Step C.

Add copper(II)sulfate pentahydrate (0.009 g; 0.2 equiv; 0.036 mmoles) and L-ascorbic acid sodium salt (0.071 g; 2.0 equiv; 0.36 mmoles) to a deoxygenated solution containing N-(but-3-yn-1-yl)-N-{2-[2-(2,3-dihydro-1H-inden-2-ylamino)-7,8-dihydropyrido[4,3-d]pyrimidin-6(5H)-yl]-2-oxoethyl}acetamide (0.075 g; 1.0 equiv; 0.18 mmoles) in dimethylformamide (1.20 mL) and water (0.6 mL). Add azidotrimethylsilane (0.19 mL; 8 equiv; 1.44 mmoles) and heat to 90° C. for 1.5 hours. Dilute the reaction mixture with water and extract with ethyl acetate (3×50 mL). Wash the combined organic extracts with water and brine, dry over sodium sulfate, filter, and concentrate to a yellow oil. Purify the crude product by column chromatography (0 to 80% acetone in dichloromethane) to afford N-{2-[2-(2,3-dihydro-1H-inden-2-ylamino)-7,8-dihydropyrido[4,3-d]pyrimidin-6(5H)-yl]-2-oxoethyl}-n-[2-(1H-1,2,3-triazol-4-yl)ethyl]acetamide (0.025 g; 30%) as a yellow foam: MS (m/z): 461(M+1).

Scheme Y

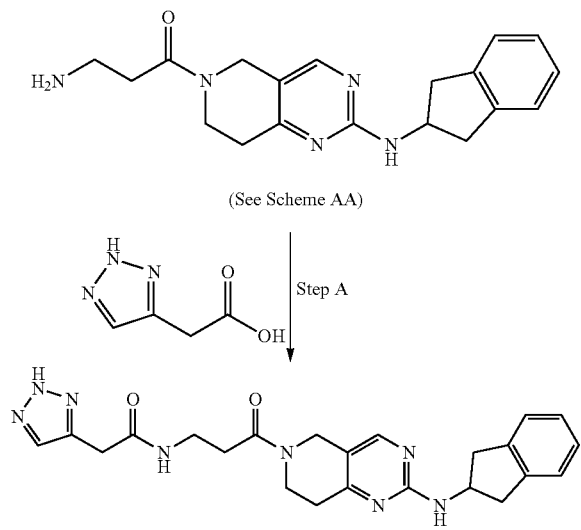

(See Scheme AA)

Example 23

Synthesis of N-{3-[2-(2,3-dihydro-1H-inden-2-ylamino)-7,8-dihydropyrido[4,3-d]pyrimidin-6(5H)-yl]-3-oxopropyl}-2-(1H-1,2,3-triazol-5-yl)acetamide

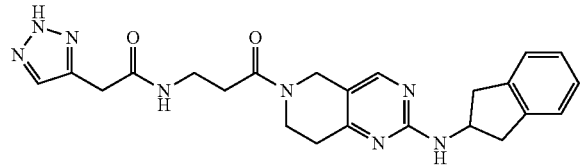 [SMILES: O=C(Cc1cn[nH]n1)NCCC(=O)N1CCc2nc(NC3Cc4ccccc4C3)ncc2C1]

Scheme Y, Step A.

Add 1-(3-dimethylaminopropyl)-3-ethylcarbodiimide hydrochloride (0.111 g; 1.5 equiv; 0.58 mmoles) to a solution of 2-(2H-triazol-4-yl)acetamide (0.056 g; 1.1 equiv; 0.42 mmoles), 3-amino-1-[2-(2,3-dihydro-1H-inden-2-ylamino)-7,8-dihydropyrido[4,3-d]pyrimidin-6(5H)-yl]propan-1-one (0.13 g; 1.0 equiv; 0.39 mmoles), and N,N-dimethyl-4-pyridinamine, (0.0094 g; 0.2 equiv; 0.077 mmoles) in dichloromethane (1.28 mL). Stir the reaction mixture for 16 hours at ambient temperature. Load the solution directly onto a silica gel column and purify by column chromatography (0 to 10% methanol in dichloromethane) to give N-{3-[2-(2,3-dihydro-1H-inden-2-ylamino)-7,8-dihydropyrido[4,3-d]pyrimidin-6(5H)-yl]-3-oxopropyl}-2-(1H-1,2,3-triazol-5-yl)acetamide (0.098 g; 57%) as a white solid: MS (m/z): 447(M+1).

Scheme Z

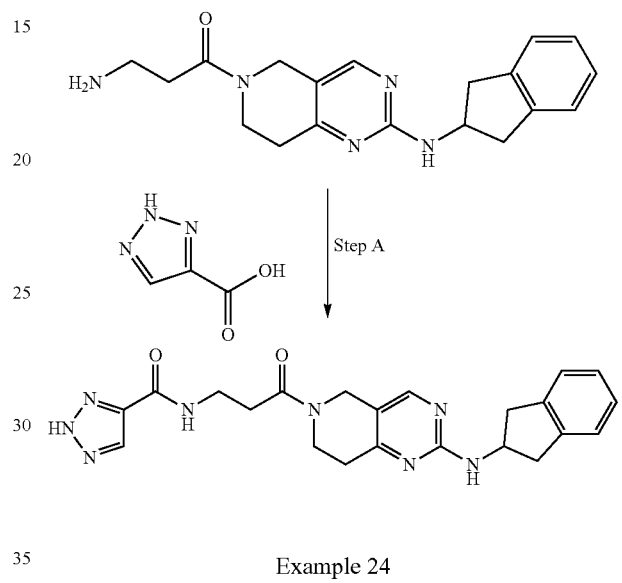

Example 24

Preparation of N-{3-[2-(2,3-dihydro-1H-inden-2-ylamino)-7,8-dihydropyrido[4,3-d]pyrimidin-6(5H)-yl]-3-oxopropyl}-1H-1,2,3-triazole-4-carboxamide

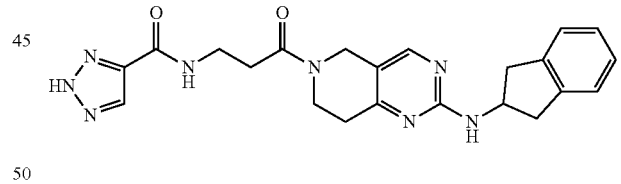

Scheme Z, Step A.

Add 1-(3-dimethylaminopropyl)-3-ethylcarbodiimide hydrochloride (0.111 g; 1.5 equiv; 0.58 mmoles) to a solution of 2H-triazole-4-carboxylic acid (0.048 g; 1.1 equiv; 0.42 mmoles), 3-amino-1-[2-(2,3-dihydro-1H-inden-2-ylamino)-7,8-dihydropyrido[4,3-d]pyrimidin-6(5H)-yl]propan-1-one (0.13 g; 1.0 equiv; 0.39 mmoles), and N,N-dimethyl-4-pyridinamine, (0.0094 g; 0.2 equiv; 0.077 mmoles) in dichloromethane (1.28 mL). Stir the reaction at ambient temperature for 16 hours. Load the mixture directly onto a silica gel column and purify by column chromatography (0 to 10% methanol in ethyl acetate) to afford N-{3-[2-(2,3-dihydro-1H-inden-2-ylamino)-1H-inden-2-ylamino)-7,8-dihydropyrido[4,3-d]pyrimidin-6(5H)-yl]-3-oxopropyl}-1H-1,2,3-triazole-4-carboxamide (0.105 g; 63%) as a white solid: MS (m/z): 433(M+1).

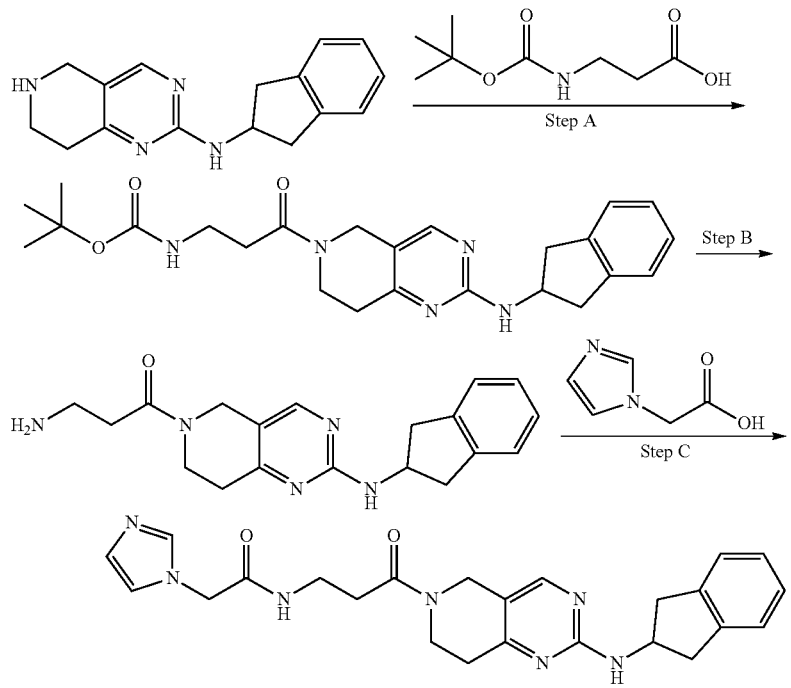

Preparation 47

Synthesis of tert-butyl {3-[2-(2,3-dihydro-1H-inden-2-ylamino)-7,8-dihydropyrido[4,3-d]pyrimidin-6(5H)-yl]-3-oxopropyl}carbamate

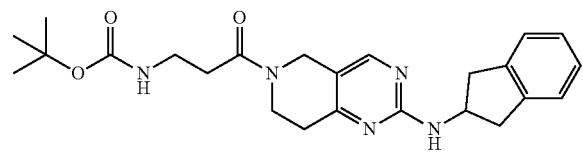 [SMILES: CC(C)(C)OC(=O)NCCC(=O)N1CCc2nc(NC3Cc4ccccc4C3)ncc2C1]

Scheme AA, Step A.

Add 1-(3-dimethylaminopropyl)-3-ethylcarbodiimide hydrochloride (2.69 g; 1.5 equiv; 14.06 mmoles) to a flask containing 3-(tert-butoxycarbonylamino)propanoic acid (1.8 g; 1.0 equiv; 9.37 mmoles), N-indan-2-yl-5,6,7,8-tetrahydropyrido[4,3-d]pyrimidin-2-amine (2.50 g; 1.0 equiv; 9.37 mmoles) and N,N-dimethyl-4-pyridinamine, (0.229 g; 0.2 equiv; 1.87 mmoles) in dichloromethane (30 mL). Stir the mixture for 2 hours, then load the solution directly onto a silica gel column and purify by column chromatography (30 to 100% ethyl acetate in dichloromethane) to give tert-butyl {3-[2-(2,3-dihydro-1H-inden-2-ylamino)-7,8-dihydropyrido[4,3-d]pyrimidin-6(5H)-yl]-3-oxopropyl}carbamate (3.42 g; 83%) as a colorless foam: MS (m/z): 438(M+1).

Preparation 48

Synthesis of 3-amino-1-[2-(2,3-dihydro-1H-inden-2-ylamino)-7,8-dihydropyrido[4,3-d]pyrimidin-6(5H)-yl]propan-1-one

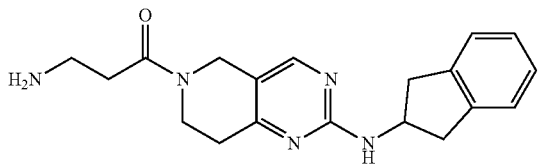 [SMILES: NCCC(=O)N1CCc2nc(NC3Cc4ccccc4C3)ncc2C1]

Scheme AA, Step B.

Add trifluoroacetic acid (1 mL) to a solution of tert-butyl {3-[2-(2,3-dihydro-1H-inden-2-ylamino)-7,8-dihydropyrido[4,3-d]pyrimidin-6(5H)-yl]-3-oxopropyl}carbamate (0.19 g; 1.0 equiv; 0.44 mmoles) in dichloromethane (1 mL) and stir for 16 hours. Concentrate the mixture and then partition the residue between dichloromethane and 1N sodium hydroxide. Separate the layers and further extract the aqueous layer with dichloromethane. Wash the combined organic extracts with brine, dry over sodium sulfate, filter, and concentrate to afford the desired 3-amino-1-[2-(2,3-dihydro-1H-inden-2-ylamino)-7,8-dihydropyrido[4,3-d]pyrimidin-6(5H)-yl]propan-1-one (0.145 g; 98%): MS (m/z): 338(M+1).

Example 25

Synthesis of H-{3-[2-(2,3-dihydro-1H-inden-2-ylamino)-7,8-dihydropyrido[4,3-d]pyrimidin-6(5H)-yl]-3-oxopropyl}-2-(1H-imidazol-1-yl)acetamide

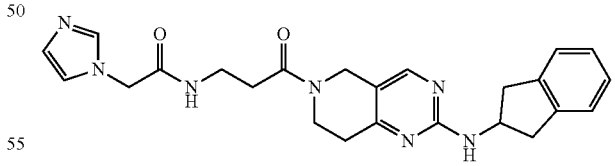

Scheme AA, Step C.

Add 1-(3-dimethylaminopropyl)-3-ethylcarbodiimide hydrochloride (0.124 g; 1.5 equiv; 0.65 mmoles) to a solution of 2-imidazol-1-ylacetic acid (0.060 g; 1.1 equiv; 0.47 mmoles), 3-amino-1-[2-(2,3-dihydro-1H-inden-2-ylamino)-7,8-dihydropyrido[4,3-d]pyrimidin-6(5H)-yl]propan-1-one (0.145 g; 1.0 equiv; 0.43 mmoles), and N,N-dimethyl-4-pyridinamine, (0.0105 g; 0.2 equiv; 0.086 mmoles) in dichloromethane (1.43 mL). Stir the resulting solution for 16 hours. Load the solution directly onto a silica gel column and purify by column chromatography (0 to 10% methanol in dichloromethane) to afford H-{3-[2-(2,3-dihydro-1H-inden-2-ylamino)-7,8-dihydropyrido[4,3-d]pyrimidin-6(5H)-yl]-3-oxopropyl}-2-(1H-imidazol-1-yl)acetamide (0.094 g; 49%) as a white solid: MS (m/z): 446(M+1).

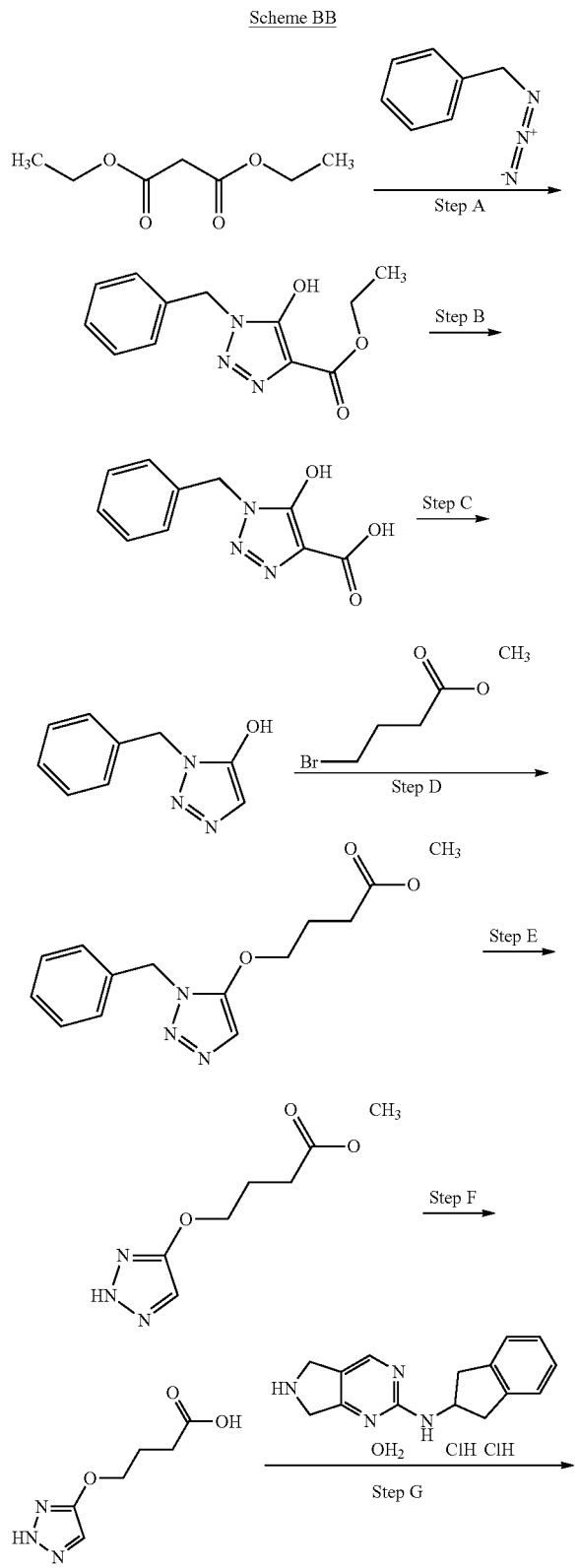

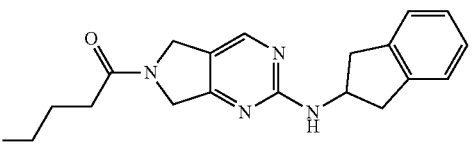

Preparation 49

Synthesis of ethyl 1-benzyl-5-hydroxy-1H-1,2,3-triazole-4-carboxylate

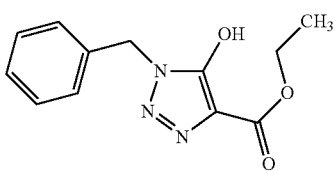 [SMILES: CCOC(=O)c1nnn(Cc2ccccc2)c1O]

Scheme BB, Step A.

Add diethyl propanedioate (7.16 mL; 1.3 equiv; 46.67 mmoles) followed by potassium carbonate (19.85 g; 4 equiv; 143.60 mmoles) to a solution of benzyl azide (4.5 mL; 1.0 equiv; 35.90 mmoles) in dimethyl sulfoxide (36 mL), and heat the resulting solution for 16 hours at 40° C. Add 5 N hydrochloric acid until the pH=1, and then filter the resulting precipitate. Wash the precipitate with water and dry to afford 1-benzyl-5-hydroxy-1H-1,2,3-triazole-4-carboxylate (5.65 g; 64%) as a white solid: MS (m/z): 248(M+1).

Preparation 50

Synthesis of 1-benzyl-5-hydroxy-1H-1,2,3-triazole-4-carboxylic acid

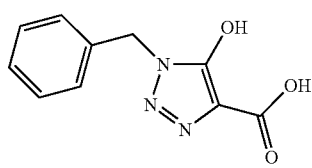 [SMILES: O=C(O)c1nnn(Cc2ccccc2)c1O]

Scheme BB, Step B.

Stir a 90° C. solution of 1-benzyl-5-hydroxy-1H-1,2,3-triazole-4-carboxylate (1.46 g; 1.0 equiv; 5.90 mmoles) and sodium hydroxide (1N; 10.00 mL; 1.7 equiv; 10.00 mmoles) for 9 hours. Add 1N hydrochloric acid until the pH is 2, then filter the reaction and dry the filter cake to afford 1-benzyl-5-hydroxy-1H-1,2,3-triazole-4-carboxylic acid (1.15 g; 89%): MS (m/z): 220(M+1).

Preparation 51

Synthesis of 1-benzyl-1H-1,2,3-triazol-5-ol

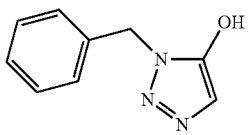 [SMILES: Oc1cnnn1Cc1ccccc1]

Scheme BB, Step C. Place a solution of 1-benzyl-5-hydroxy-1H-1,2,3-triazole-4-carboxylic acid (1.25 g; 1.0 equiv; 5.70 mmoles) in dimethylformamide (2 mL) in a reaction block preheated to 125° C. and heat for 2 minutes. Allow the reaction to cool to room temperature and use the 1-benzyl-1H-1,2,3-triazol-5-ol immediately in the next step: MS (m/z): 176(M+1).

Preparation 52

Synthesis of methyl 4-[(1-benzyl-1H-1,2,3-triazol-5-yl)oxy]butanoate

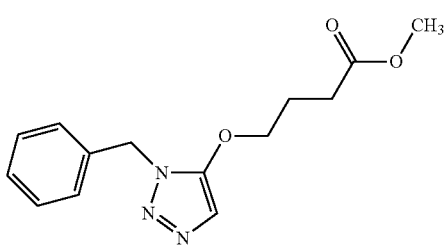 [SMILES: COC(=O)CCCOc1cnnn1Cc1ccccc1]

Scheme BB, Step D.

Add methyl 4-bromobutyrate (1.48 mL; 2.0 equiv; 11.42 mmoles) to a solution of 1-benzyl-1H-1,2,3-triazol-5-ol (1.0 g; 1.0 equiv; 5.71 mmoles) and potassium carbonate (1.59 g; 2.0 equiv; 11.42 mmoles) in dimethylformamide (2 mL). Heat the reaction at 50° C. for 1 hour, then cool to ambient temperature and stir for 16 hours. Dilute the reaction with ethyl acetate and water. Separate the layers and further extract the aqueous layer with ethyl acetate. Wash the combined organic extracts with water (3×), dry over sodium sulfate, filter, and concentrate. Purify the crude product by column chromatography (0 to 50% ethyl acetate in dichloromethane) to afford methyl 4-[(1-benzyl-1H-1,2,3-triazol-5-oxy]butanoate (0.506 g; 32%): MS (m/z): 276(M+1).

Preparation 53

Synthesis of methyl 4-(2H-triazol-4-yloxy)butanoate

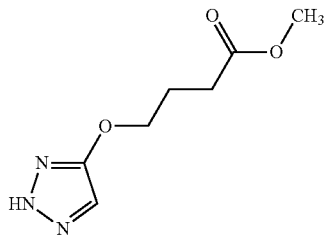

Scheme BB, Step E.

Add 5 drops of concentrated hydrochloric acid to a heterogeneous solution of methyl 4-[(1-benzyl-1H-1,2,3-triazol-5-yl)oxy]butanoate (0.50 g; 1.0 equiv; 1.82 mmoles) and 10% palladium on carbon (0.05 g; 0.025 equiv; 0.047 mmoles) in ethanol (7 mL). Evacuate and backfill with nitrogen (3×) then hydrogen (3×), and vigorously stir the reaction mixture for 16 hours under 50 psi hydrogen. Filter the contents and concentrate the filtrate to afford methyl 4-(2H-triazol-4-yloxy)butanoate (0.335 g; 99%). MS (m/z): 184(M−1).

Preparation 54

Synthesis of 4-(2H-triazol-4-yloxy)butanoic acid

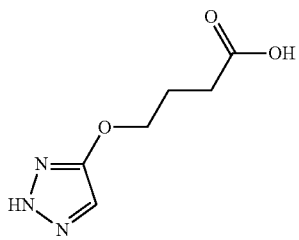 [SMILES: O=C(O)CCCOc1cn[nH]n1]

Scheme BB, Step F.

Add 1N sodium hydroxide (2.32 mL; 2.0 equiv; 2.32 mmoles) to a solution of methyl 4-(2H-triazol-4-yloxy)butanoate (0.215 g; 1.0 equiv; 1.16 mmoles) in ethanol (1 mL) and heat the mixture to 60° C. for 16 hours. Add 1N hydrochloric acid (2.32 mL; 2.0 equiv; 2.32 mmoles) and concentrate to afford 4-(2H-triazol-4-yloxy)butanoic acid (0.20 g; 100%). Use without further purification in the next step: MS (m/z): 170(M−1).

Example 26

Synthesis of 1-[2-(2,3-dihydro-1H-inden-2-ylamino)-5,7-dihydro-6H-pyrrolo[3,4-d]pyrimidin-6-yl]-4-(1H-1,2,3-triazol-5-yloxy)butan-1-one

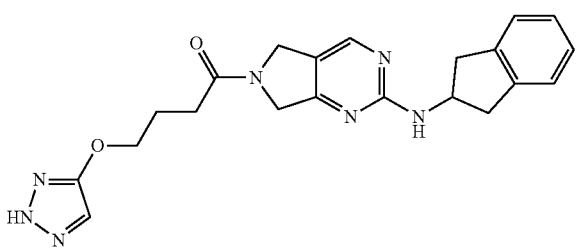 [SMILES: O=C(CCCOc1cn[nH]n1)N1Cc2cnc(NC3Cc4ccccc4C3)nc2C1]

Scheme BB, Step G.

Add 1-(3-dimethylaminopropyl)-3-ethylcarbodiimide hydrochloride (0.168 g; 1.5 equiv; 0.88 mmoles) and diisopropylethylamine (0.41 mL; 4 equiv; 2.34 mmoles) to a solution of 4-(2H-triazol-4-yloxy)butanoic acid (0.1 g; 1.0 equiv; 0.58 mmoles) and N-(2,3-dihydro-1H-inden-2-yl)-6,7-dihydro-5H-pyrrolo[3,4-d]pyrimidin-2-amine dihydrochloride hydrate (0.201 g; 1.0 equiv; 0.58 mmoles), and N,N-dimethyl-4-pyridinamine, (0.014 g; 0.2 equiv; 0.12 mmoles) in dichloromethane (5.8 mL). Stir the reaction for 2 hours then load the reaction mixture directly onto a silica gel column. Purify by column chromatography (10% (2 N ammonia in methanol)/ethyl acetate) to afford 1-[2-(2,3-dihydro-1H-inden-2-ylamino)-5,7-dihydro-6H-pyrrolo[3,4-d]pyrimidin-6-yl]-4-(1H-1,2,3-triazol-5-yloxy)butan-1-one (0.104 g; 44%) as a white solid: MS (m/z): 406(M+1).

Inhibition of Autotaxin as Measured by Choline Release

The purpose of this assay is to detect autotaxin inhibition using a choline release assay.

Test compounds (10 mM stocks in 100% DMSO) are serially diluted in 100% DMSO resulting in 10 concentrations of 100× inhibitor in half area 96 well plates (Corning 3992). Each of these 10 wells in 100% DMSO is diluted 1:33.33 in assay buffer in round bottom 96 well plates (Fisher 12565502) resulting in 3× concentrations in well containing 3% DMSO. The assay buffer is 50 mM Tris pH8.0, 5 mM KCl, 1 mM CaCl$_2$, 1 mM MgCl$_2$, 0.01% TRITON™ X-100 (Sigma T9284) and 0.01% fatty acid free bovine serum albumin (Sigma A8806). A 20 μl aliquot of each 3× test compound is then added to black flat bottom 96 well plates (Corning 3991) in singlicate. A 20 μl aliquot per well of 3× recombinant human autotaxin (full length human autotaxin with a C-terminal His tag transfected into 293E cells and purified via nickel chelate and size exclusion chromatography) is then added to every well except for the no enzyme control wells. A 20 μl aliquot per well of assay buffer is added to the no enzyme control wells. A 20 μl aliquot of a 3× cocktail containing choline oxidase (Sigma C5896), horseradish peroxidase (Sigma P8125), amplex ultrared (Invitrogen A36006) and the autotaxin substrate lysophosphatidylcholine (LPC) 16:0 (Avanti Polar Lipids 855675P) is added to each well while avoiding exposure to light. The final concentrations in the well of choline oxidase, horseradish peroxidase, amplex ultrared and LPC 16:0 are 0.4 units/ml, 4 units/ml, 40 μM and 30 μM respectively. The plate is then sealed with aluminum foil seals and incubated at 37° C. for 1 hour in a Labline Imperial III incubator. During this incubation, LPC is cleaved by autotaxin resulting in Lysophosphatidic Acid (LPA) 16:0 and choline. The choline that is released is oxidized by choline oxidase resulting in betaine and hydrogen peroxide. The hydrogen peroxide reacts with the horseradish peroxide and amplex ultrared to form the fluorescent molecule resorufin. The resorufin on the plates is measured with a SpectraMax Gemini EM fluorometer at excitation-emission wavelengths of 530-590 nm using SoftMax Pro 4.8 software. IC$_{50}$s are calculated using 4 parameter curve fits with the internal Lilly software OLO curve fitting tool. Results are expressed as the arithmetic mean+/− standard deviation; n=x. The compounds of Examples 1-15 herein were tested essentially as described above, and exhibited an IC$_{50}$ for autotaxin of lower than about 100 nM. The following exemplified compounds were tested essentially as described above and exhibited the following activity for autotaxin:

TABLE 1

| Inhibition of Autotaxin: Choline Release Assay | |
|---|---|
| Test Compound | IC$_{50}$ (nM) |
| Example 1 and 1a | 5.7 nM (n = 7) |
| Example 2 and 2a | <1.7 nM (n = 5) |

The data in Table 1 illustrate that the compounds of Table 1 inhibit autotaxin using the in vitro choline release assay.

Reduction of LPA in the Presence of Human Plasma

The following assay is intended to measure the reduction of LPA. This assay is a tool that can be used to identify selective autotaxin-mediated LPA inhibitor compounds when it is used to test compounds that have been identified as autotaxin inhibitors. LPA biosynthesis through autotaxin is believed to be the source of LPA for LPA$_1$ mediated neuropathic pain. Makoto Inoue, et. al, "*Autotaxin, a synthetic enzyme of lysophosphatidic acid (LPA), mediates the induction of nerve-injured neuropathic pain*", Molecular Pain, 2008, 4:6. Targeted inhibition of the autotaxin mediated LPA biosynthesis is supported by the results of this assay.

Units of plasma from healthy human female donors collected in sodium heparin (Lampire Biologicals) are pooled, aliquoted and stored at −80° C. On the day of assay, aliquots of the plasma are thawed and spun for 10 minutes at 3000 RPMs at 4° C. in a centrifuge to remove debris. A 90 μl aliquot of plasma is added to each well of a 96 well round bottom polypropylene plate. A 10 μL aliquot of 10× test compound containing 10% DMSO in assay buffer (50 mM Tris pH8.0, 5 mM KCl, 1 mM CaCl$_2$, 1 mM MgCl$_2$) is added to each well except for the control wells which contain no test compound. This results in 10 1× concentrations of test compound in singlicate with a final concentration of 1% DMSO in 90% plasma. A 10 μl aliquot of 10% DMSO in assay buffer without test compound is added to the 0 hour (n=8) and 3 hour no test compound controls (n=8) wells. A 10 μl aliquot of 500 mM ethylenediaminetetraacetic acid (EDTA) is added to each of the 0 hour no test compound control wells to chelate endogenous autotaxin. The entire contents of the 0 hour no test compound control wells are transferred to a new 96 well round bottom polypropylene plate and frozen at −80° C. The plate containing plasma +/− test compounds (minus the 0 hour no inhibitor control wells) is then incubated for 3 hours at 37° C. in a Robbins Scientific™ model 400 hybridization incubator while rocking at 14,000 RPMs. During this 3 hour incubation, lecithin cholesterol acyltransferases present in the plasma cleave phosphatidylcholine resulting in higher plasma levels of the autotaxin substrate lysophosphatidylcholine (LPC). The increased endogenous LPC levels are cleaved by endogenous autotaxin resulting in higher plasma concentrations of endogenous lysophosphatidic acid (LPA) (Nakamura et al, Clinical Biochemistry 40 (2007), 274-277). This increase in LPA in the 3 hour incubation can be inhibited by autotaxin inhibitors. Following the 3 hour incubation, 10 μl of 500 mM EDTA is added to all of the remaining wells (test compound containing wells and 3 hour no test compound control wells) to chelate the endogenous autotaxin. The entire contents of these wells are then added to the plate containing the 0 hour no test compound control plasma that had previously been stored at −80° C. (without thawing the 0 hour plasma). The plate is then re-covered with an aluminum foil seal and placed back at −80° C. until extraction for mass spec analysis. On the day of extraction, the plates are thawed on ice and 25 μl of plasma from each well is transferred to a 2 ml TrueTaper™ square 96 deep well plate (Analytical Sales and Products #968820). A 400 μml aliquot of extraction buffer (50% methanol, 49.9% acetonitrile, 0.1% acetic acid) containing LPA internal standards (50 ng/ml D5 deuterium LPA 16:0 and 50 ng/ml D5 deuterium LPA 18:0) is added to each well and the total LPA in each sample is determined by mass spec analysis. Percent reduction of LPA is calculated according to the following formula:

100-(3 hour plasma+test compound−0 hour plasma no test compound control)/(3 hour plasma no test compound control−0 hour plasma no test compound control)×100

IC$_{50}$ values are calculated using 4 parameter curve fitting. Results are expressed as the arithmetic mean+/− standard deviation; n=x. Results of this assay using compounds of this invention show LPA reduction that is dose dependent and statistically significant.

TABLE 2

| Reduction of LPA in Human Plasma | |
| --- | --- |
| Test Compound | IC$_{50}$ (nM) |
| Example 1 and 1a | 10 nM (n = 6) |
| Example 2 and 2a | 2.2 nM (n = 4) |

The data in Table 2 demonstrate that the compounds decrease LPA in the presence of human plasma. The results support that the compounds inhibit autotaxin mediated LPA biosynthesis.

We claim:

1. A compound of the of the Formula I:

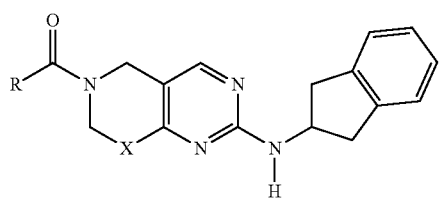

wherein X is a bond or CH$_2$;
R is selected from the group consisting of

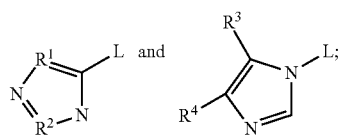

R$^1$ and R$^2$ are each independently selected from the group consisting of CH and N;
R$^3$ is H or CH$_3$;
R$^4$ is H or CH$_3$;
L is selected from the group consisting of —O(CH$_2$)$_3$—, —C(O)NH(CH$_2$)$_2$—, —CH$_2$C(O)NH(CH$_2$)$_2$—, —(CH$_2$)$_3$N(C(O)CH$_3$)CH$_2$—, —(CH$_2$)$_2$N(C(O)CH$_3$) CH$_2$—, —(CH$_2$)$_3$NH—, (CH$_2$)$_2$OCH$_2$—, —(CH$_2$)$_4$—, —(CH$_2$)$_2$NHCH$_2$—, —(CH$_2$)$_3$O—, and —CH$_2$O (CH$_2$)$_2$—;
or a pharmaceutically acceptable salt thereof.

2. A compound or salt according to claim 1 wherein R is

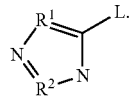

3. A compound or salt according to claim 2 wherein R$^1$ is CH.
4. A compound or salt according to claim 3 wherein R$^2$ is N.
5. A compound or salt according to claim 4 wherein L is selected from the group consisting of —(CH$_2$)$_4$—, —O(CH$_2$)$_3$—, —(CH$_2$)$_2$OCH$_2$—, —(CH$_2$)$_3$O—, and —CH$_2$O(CH$_2$)$_2$—.
6. A compound or salt according to claim 5 wherein L is —(CH$_2$)$_2$OCH$_2$—.
7. A compound or salt according to claim 5 wherein L is —O(CH$_2$)$_3$—.
8. A compound or salt according to claim 3 wherein L is selected from the group consisting of —(CH$_2$)$_2$N(C(O)CH$_3$) CH$_2$—, —(CH$_2$)$_3$N(C(O)CH$_3$)CH$_2$—, and —CH$_2$C(O)NH (CH$_2$)$_2$—.
9. A compound or salt according to claim 1 wherein X is a bond.
10. A compound or salt according to claim 1 wherein X is CH$_2$.
11. A compound or salt according to claim 1 that is 1-[2-(2,3-dihydro-1H-inden-2-ylamino)-7,8-dihydropyrido[4,3-d]pyrimidin-6(5H)-yl]-2-[2-(1H-1,2,3-triazol-4-yl)ethoxy] ethanone

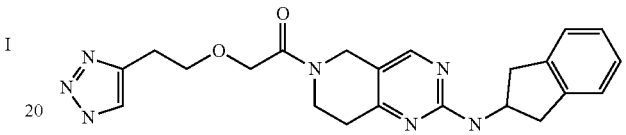

12. A compound or salt according to claim 1 that is that is 1-[2-(2,3-dihydro-1H-inden-2-ylamino)-5,7-dihydro-6H-pyrrolo[3,4-d]pyrimidin-6-yl]-2-[2-(1H-1,2,3-triazol-4-yl) ethoxy]ethanone

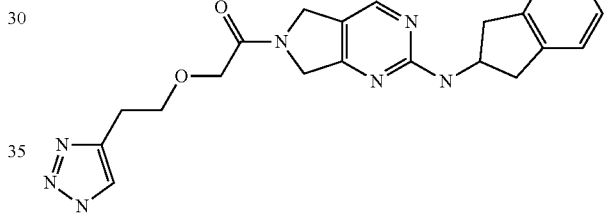

13. A pharmaceutical composition comprising a compound or a pharmaceutically acceptable salt thereof, according to claim 1, in combination with one or more pharmaceutically acceptable carriers, diluents, or excipients.

14. An intermediate compound of the formula:

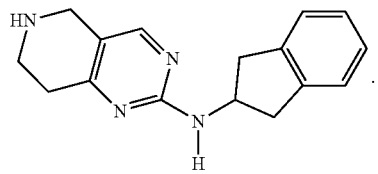 [SMILES: c1ccc2c(c1)CC(Nc1ncc3c(n1)CCNC3)C2]

15. An intermediate compound of the formula:

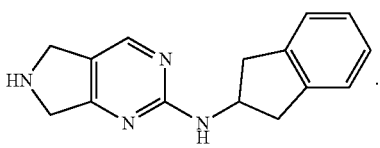 [SMILES: c1ccc2c(c1)CC(Nc1ncc3c(n1)CNC3)C2]

* * * * *

UNITED STATES PATENT AND TRADEMARK OFFICE
CERTIFICATE OF CORRECTION

| | |
|---|---|
| PATENT NO. | : 8,969,555 B2 |
| APPLICATION NO. | : 14/148775 |
| DATED | : March 3, 2015 |
| INVENTOR(S) | : Thomas James Beauchamp et al. |

It is certified that error appears in the above-identified patent and that said Letters Patent is hereby corrected as shown below:

In the Claims,

In column 67, line 14, Claim 1, after "of the" delete "of the".

In column 68, line 23, Claim 12, after "that is" delete "that is".

Signed and Sealed this
Thirtieth Day of June, 2015

Michelle K. Lee
*Director of the United States Patent and Trademark Office*